15 # United States Patent

Reich et al.

(10) Patent No.: US 8,278,319 B2
(45) Date of Patent: Oct. 2, 2012

(54) SUBSTITUTED SPIROAMINE COMPOUNDS

(75) Inventors: Melanie Reich, Aachen (DE); Stefan Oberboersch, Aachen (DE); Stefan Schunk, Aachen (DE); Ruth Jostock, Stolberg (DE); Sabine Hees, Aachen (DE); Michael Engels, Turnhout (DE)

(73) Assignee: Gruenenthal GmbH, Aachen (DE)

( * ) Notice: Subject to any disclaimer, the term of this patent is extended or adjusted under 35 U.S.C. 154(b) by 306 days.

(21) Appl. No.: 12/608,543

(22) Filed: Oct. 29, 2009

(65) Prior Publication Data

US 2010/0113417 A1 May 6, 2010

Related U.S. Application Data

(60) Provisional application No. 61/109,293, filed on Oct. 29, 2008.

(30) Foreign Application Priority Data

Oct. 29, 2008 (EP) .................................. 08018868

(51) Int. Cl.
*A61K 31/44* (2006.01)
*C07D 213/00* (2006.01)
(52) U.S. Cl. ......................................... 514/278; 546/15
(58) Field of Classification Search .................. 514/278; 546/15
See application file for complete search history.

(56) References Cited

U.S. PATENT DOCUMENTS

| 2008/0153843 A1 | 6/2008 | Oberboersch et al. |
| 2008/0249128 A1 | 10/2008 | Oberboersch et al. |

FOREIGN PATENT DOCUMENTS

| WO | WO 2007/101007 A2 | 9/2007 |
| WO | WO 2007/140383 A2 | 12/2007 |
| WO | WO 2008/040492 A1 | 4/2008 |
| WO | WO 2008/046573 A1 | 4/2008 |

OTHER PUBLICATIONS

Ha SN, Hey PJ, Ransom RW, Bock MG, Su DS, Murphy KL, Chang R, Chen TB, Pettibone D, Hess JF. Identification of the critical residues of bradykinin receptor B1 for interaction with the kinins guided by site-directed mutagenesis and molecular modeling. Biochemistry. Dec. 5, 2006;45(48):14355-61.*
J. Fred Hess, et al, "Generation and Characterization of a Humanized bradykinin B1 Receptor Mouse", Biol. Chem., Feb. 2006, pp. 196-201, vol. 387.
R. Hayashi, et al., "Bradykinin Stimulates IL-6 and IL-8 Production by Human Lung Fibroblasts through ERK- and p38 MAPK-dependent Mechanisms", European Respiratory Journal, 2000, pp. 452-458, vol. 16.

Bichoy H. Gabra, et al, "The Kinin System Mediates Hyperalgesia through the Inducible Bradykinin B1 Receptor Subtype: Evidence in Various Experimental Animal Models of Type 1 and Type 2 Diabetic Neuropathy", Biol. Chem., Feb. 2006, pp. 127-143, vol. 387.
Joao B. Calixto, et al., "Kinin B., Receptors: Key G-Protein-Coupled Receptors and Their Role in inflammatory and Painful Processes", British Journal of Pharmacology, 2004, pp. 803-818, vol. 143.
Sara H. Bengtson, et al., "Kinin Receptor Expression During *Staphylococcus aureus* Infection", Blood, 2006, pp. 2055-2063, vol. 108.
Antoni Stadnicki, et al., "Immunolocalization and Expression of Kinin $B_1R$ and $B_2R$ Receptors in Human Inflammatory Bowel Disease", AJP Gastrointest Liver Physiol, Aug. 2005, pp. G361-G366, vol. 289.
A. Prat, et al., "Bradykinin $B_1$ Receptor Expression and Function on T Lymphocytes in Active Multiple Sclerosis", Dec. 10, 1999, pp. 2087-2092, vol. 63, No. 9, American Academy of Neurology.
Joao B. Pesquero, et al., Genetically Altered Animal Models in the Kallikrein-Kinin System, Biol. Chem., Feb. 2006, pp. 119-126, vol. 387.
Joao B. Pesquero, et al., "Hypoalgesia and Altered Inflammatory Responses in Mice Lacking Kinin B1 Receptors", PNAS, Jul. 6, 2000, pp. 8140-8145, vol. 97, No. 14.
Giselle P. Passos, et al., "Kinin $B_1$ Receptor Up-Regulation after Lipopolysaccharide Administration: Role of Proinflammatory Cytokines and Neutrophll Influx[1]", The Journal of Immunology, 2004, pp. 1839-1847, vol. 172.
L. M. Fredrik Leeb-Lundberg, et al., "International Union of Pharmacology. XLV. Classification of the Klnin Receptor Family: from Molecular Mechanisms to Pathophysiological Consequences", Pharmacological Reviews, 2005, pp. 27-77, vol. 57, No. 1.
European Search Report including partial English translation dated Mar. 20, 2009 (Six (6) pages).
English translation of International Search Report dated Jan. 28, 2010 and PCT/ISA/237 Form (Thirteen (13) pages).

* cited by examiner

*Primary Examiner* — Paul Zarek
(74) *Attorney, Agent, or Firm* — Crowell & Moring LLP

(57) ABSTRACT

Substituted spiroamine compounds corresponding to the formula (I)

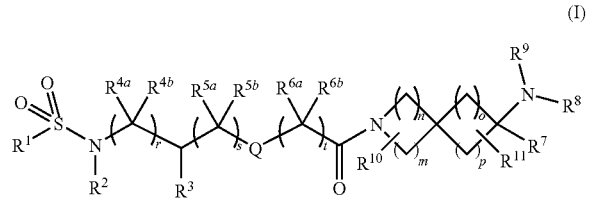

In which m, n, o, p, Q, r, s, t, $R^1$, $R^2$, $R^3$, $R^{4a}$, $R^{4b}$, $R^{5a}$, $R^{5b}$, $R^{6a}$, $R^{6b}$, $R^7$, $R^8$, $R^9$, $R^{10}$ and $R^{11}$ have defined meanings; a process for the preparation of such compounds, pharmaceutical compositions containing such compounds and the use of substituted spiroamines for the treatment or inhibition of pain and/or other conditions mediated by the bradykinin 1 receptor.

19 Claims, No Drawings

SUBSTITUTED SPIROAMINE COMPOUNDS

CROSS REFERENCE TO RELATED APPLICATIONS

This application claims priority from U.S. provisional patent application No. 61/109,293 and European patent application no. EP 08018868.3, both filed Oct. 29, 2008, the entire disclosures of which are incorporated herein by reference.

BACKGROUND OF THE INVENTION

The present invention relates to substituted spiroamines, processes for the preparation thereof, medicaments containing these compounds and the use of substituted spiroamines in pharmaceutical compositions and for the treatment of pain and other conditions mediated by the bradykinin 1 receptor (B1R).

In contrast to the constitutive expression of the bradykinin 2 receptor (B2R), the bradykinin 1 receptor is not expressed or is only weakly expressed in most tissues. Nevertheless, expression of the B1R can be induced on various cells. By way of example, in the course of inflammation reactions a rapid and pronounced induction of the B1R takes place on neuronal cells, but also on various peripheral cells, such as fibroblasts, endothelial cells, granulocytes, macrophages and lymphocytes. Thus, in the course of inflammation reactions a switch from a B2R to a B1R dominance occurs on the cells involved. The cytokines interleukin-1 (IL-1) and tumour necrosis factor alpha (TNFα) are substantially involved in this B1R up-regulation (Passos et al. J. Immunol. 2004, 172, 1839-1847). After activation with specific ligands, B1R-expressing cells can subsequently themselves secrete inflammation-promoting cytokines, such as IL-6 and IL-8 (Hayashi et al., Eur. Respir. J. 2000, 16, 452-458). This leads to inwards migration of further inflammation cells, for example neutrophilic granulocytes (Pesquero et al., PNAS 2000, 97, 8140-8145). The bradykinin B1R system can contribute to the chronification of diseases via these mechanisms. This is demonstrated by a large number of animal studies (overviews in Leeb-Lundberg et al., Pharmacol Rev. 2005, 57, 27-77 and Pesquero et al., Biol. Chem. 2006, 387, 119-126). In humans too, an increased expression of the B1R is seen, for example on enterocytes and macrophages in the affected tissue of patients with inflammatory bowel diseases (Stadnicki et al., Am. J. Physiol. Gastrointest. Liver Physiol. 2005, 289, G361-366) and on T lymphocytes of patients with multiple sclerosis (Prat et al., Neurology. 1999; 53, 2087-2092), or an activation of the bradykinin B2R-B1R system is seen in the course of infections with *Staphylococcus aureus* (Bengtson et al., Blood 2006, 108, 2055-2063). Infections with *Staphylococcus aureus* are responsible for disease profiles such as superficial infections of the skin through to septic shock.

Based on the pathophysiological relationships described, there is great therapeutic potential for the use of B1R antagonists against acute and in particular chronic inflammatory diseases. They include diseases of the respiratory tract (bronchial asthma, allergies, COPD/chronic obstructive pulmonary disease, cystic fibrosis, etc.), inflammatory bowel diseases (ulcerative colitis, CD/Crohn's disease, etc.), neurological diseases (multiple sclerosis, neurodegeneration, etc.), inflammations of the skin (atopic dermatitis, psoriasis, bacterial infections, etc.) and mucous membranes (Behcet's disease, chronic pelvic pain, prostatitis, etc.), rheumatic diseases (rheumatoid arthritis, osteoarthritis, etc.), septic shock and reperfusion syndrome (following heart attack or stroke).

The bradykinin (receptor) system is moreover also involved in the regulation of angiogenesis (potential as an angiogenesis inhibitor in cases of cancer and macula degeneration in the eye), and B1R-knockout mice are protected from the induction of obesity by a particularly high-fat diet (Pesquero et al., Biol. Chem. 2006, 387, 119-126). B1R antagonists are therefore also suitable for the treatment of obesity.

B1R antagonists are particularly suitable for the treatment of pain, in particular inflammatory pain and neuropathic pain (Calixto et al., Br. J. Pharmacol 2004, 1-16), and here in particular diabetic neuropathy (Gabra et al., Biol. Chem. 2006, 387, 127-143). They are also suitable for the treatment of migraine.

In the development of B1R modulators there is the problem, however, that the human and the rat B1R receptor differ so widely that many compounds which are good B1R modulators on the human receptor have only a poor or no affinity for the rat receptor. This makes animal pharmacology studies considerably more difficult, since many studies are usually conducted on the rat. However, if there is no activity on the rat receptor, neither action nor side-effect can be investigated on the rat. This has already meant that transgenic animals with human B1 receptors have been produced for animal pharmacology studies (Hess et al., Biol. Chem. 2006; 387(2):195-201). Working with transgenic animals is, however, more expensive than working with the unmodified animals.

The patent applications WO 2007/140383 and WO 2007/101007 describe compounds which in in-vitro assays exhibit an antagonistic action on the macaque B1 receptor. Experimental data on the activity on the human B1 receptor or the B1 receptor of the rat is not disclosed.

Published US patent application nos. US 2008/153843 (=WO 2008/040492) and US 2008/249128 (=WO 2008/046573) describe compounds which in in-vitro assays exhibit an antagonistic action on both the human and the rat B1 receptors.

However, there remains a need for novel B1R modulators, and particularly for B1R modulators which bind both to the rat receptor and to the human receptor.

SUMMARY OF THE INVENTION

It is therefore an object of the present invention to provide new compounds which exhibit bradykinin 1 receptor activity.

Another object of the invention was to provide compounds which are suitable pharmacological active ingredients in pharmaceutical compositions.

A further object of the invention was to provide compounds which are useful for treating disorders or disease states which are at least partly mediated by B1R receptors.

These and other objects have been achieved in accordance with the present invention by providing the substituted spiroamine compounds disclosed and claimed hereinafter.

The invention therefore provides substituted spiroamines having the general formula (I)

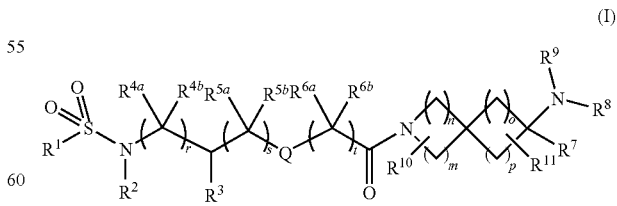

wherein
r, s and t each independently represent 0, 1 or 2;
n and o each independently represent 1 or 2;
m and p each independently represent 1, 2 or 3;
Q denotes a single bond, —O— or —CH$_2$—;

$R^1$ denotes $CH(aryl)_2$, aryl, heteroaryl or an aryl or heteroaryl group bonded via a $C_{1-3}$ alkylene group;

$R^2$ and $R^3$ are as defined under (i) or (ii):

(i) $R^2$ denotes H, $C_{1-6}$ alkyl, $C_{3-8}$ cycloalkyl, bicyclic 8-12-membered carbocyclyl, $CH(aryl)_2$, aryl or heteroaryl, or $R^2$ denotes a $C_{3-8}$ cycloalkyl, bicyclic 8-12-membered carbocyclyl, $CH(aryl)_2$, aryl or heteroaryl group bonded via a $C_{1-6}$ alkylene group or $C_{2-6}$ alkenylene group;

$R^3$ denotes H, F, Cl, Br, I, —$CF_3$, —$OCF_3$, OH, $COOR^{16}$, $CONR^{17}R^{18}$, O—$C_{1-6}$ alkyl, $C_{1-6}$ alkyl, $C_{3-8}$ cycloalkyl, aryl or heteroaryl, or $R^3$ denotes a $C_{3-8}$ cycloalkyl, aryl or heteroaryl group bonded via a $C_{1-6}$ alkylene group or $C_{2-6}$ alkenylene group; or (ii) $R^2$ and $R^3$ together with the —N—$(CR^{4a}R^{4b})_r$—CH— group linking them form a heterocycle which optionally may be substituted at one or more of its carbon ring members with one or more substituents each independently selected from the group consisting of F, Cl, Br, I, —$NH_2$, —$CF_3$, =O, —O—$CF_3$, —OH, —SH, —O—$C_{1-6}$ alkyl, $C_{1-6}$ alkyl, $C_{3-8}$ cycloalkyl, aryl and heteroaryl and/or anellated with at least one optionally substituted aryl or heteroaryl group;

wherein said heterocycle may be saturated or mono- or polyunsaturated, but is not aromatic, is 4-, 5-, 6- or 7-membered, and in addition to the N-heteroatom to which $R^2$ is bound optionally may also contain one or more heteroatoms or heteroatom groups each independently selected from the group consisting of N, $NR^{12}$, O, S, S=O and $S(=O)_2$; wherein $R^{12}$ denotes H, $C_{1-6}$ alkyl, —C(=O)—$R^{13}$, $C_{3-8}$ cycloalkyl, aryl, heteroaryl or a $C_{3-8}$ cycloalkyl, aryl or heteroaryl group bonded via a $C_{1-3}$ alkylene group, and $R^{13}$ denotes $C_{1-6}$ alkyl, $C_{3-8}$ cycloalkyl, aryl, heteroaryl or a $C_{3-8}$ cycloalkyl, aryl or heteroaryl group bonded via a $C_{1-3}$ alkylene group;

$R^{4a}$, $R^{4b}$, $R^{5a}$, $R^{5b}$, $R^{6a}$ and $R^{6b}$ each independently represent H, F, Cl, Br, I, —$CF_3$, —$OCF_3$, OH, SH, O—$C_{1-6}$ alkyl, $C_{1-6}$ alkyl, $C_{3-8}$ cycloalkyl, aryl or heteroaryl; or a $C_{3-8}$ cycloalkyl, aryl or heteroaryl group bonded via a $C_{1-6}$ alkylene group or $C_{2-6}$ alkenylene group;

$R^7$ denotes aryl, heteroaryl or an aryl or heteroaryl group bonded via a $C_{1-3}$ alkylene group;

$R^8$ and $R^9$ are as defined under (iii) or (iv):

(iii) $R^8$ and $R^9$ each independently denote H, $C_{1-6}$ alkyl, $C_{2-6}$ alkenyl, $C_{3-8}$ cycloalkyl, 3- to 8-membered heterocycloalkyl, aryl or heteroaryl or a $C_{3-8}$ cycloalkyl, 3- to 8-membered heterocycloalkyl, aryl or heteroaryl group bonded via a $C_{1-3}$ alkylene group; or (iv) $R^8$ and $R^9$ together with the nitrogen atom linking them form a heterocycle which optionally may be substituted at one or more of its carbon ring members with one or more substituents each independently selected from the group consisting of F, Cl, Br, I, —$NH_2$, —$CF_3$, =O, —O—$CF_3$, —OH, —SH, —O—$C_{1-6}$ alkyl, $C_{1-6}$ alkyl, $C_{3-8}$ cycloalkyl, aryl, heteroaryl, $C_{1-3}$ alkylene-$C_{3-8}$ cycloalkyl, $C_{1-3}$ alkylene-aryl and $C_{1-3}$ alkylene-heteroaryl and/or anellated with a saturated, mono- or polyunsaturated or aromatic ring system which optionally may be substituted at one or more of its carbon ring members with one or more substituents each independently selected from the group consisting of F, Cl, Br, I, —$NH_2$, —$CF_3$, =O, —O—$CF_3$, —OH, —SH, —O—$C_{1-6}$ alkyl, $C_{1-6}$ alkyl, $O_{3-8}$ cycloalkyl, aryl, heteroaryl, $C_{1-3}$ alkylene-$C_{3-8}$-cycloalkyl, $C_{1-3}$ alkylene-aryl and $C_{1-3}$ alkylene-heteroaryl, wherein said heterocycle may be saturated or mono- or polyunsaturated, but not aromatic, is 4-, 5-, 6- or 7-membered, in addition to the N-heteroatom to which $R^8$ and $R^9$ are bound optionally may also contain at least one further heteroatom or a heteroatom group selected from the group consisting of N, $NR^{14}$, O, S, S=O and $S(=O)_2$, the ring system is 4-, 5-, 6- or 7-membered, can contain at least one heteroatom or a heteroatom group selected from the group consisting of N, $NR^{15}$, O, S, S=O and $S(=O)_2$, $R^{14}$ denotes a substituent selected from the group consisting of H, $C_{1-6}$ alkyl, $C_{3-8}$ cycloalkyl, aryl, heteroaryl or for an aryl, heteroaryl or $C_{3-8}$ cycloalkyl bonded via a $C_{1-3}$ alkylene group, and $R^{15}$ denotes a substituent selected from the group consisting of H, $C_{1-6}$ alkyl, $C_{3-8}$ cycloalkyl, aryl, heteroaryl or for an aryl, heteroaryl or $C_{3-8}$ cycloalkyl bonded via a $C_{1-3}$ alkylene group;

$R^{10}$ and $R^{11}$ each independently represent 0 to 4 substituents which are each independently selected from the group consisting of F, OH, $C_{1-6}$ alkyl, $C_{3-8}$ cycloalkyl, aryl, heteroaryl and a $C_{3-8}$ cycloalkyl, aryl or heteroaryl group bonded via a $C_{1-6}$ alkylene group;

$R^{16}$ denotes $C_{1-6}$ alkyl;

$R^{17}$ and $R^{18}$ are as defined under (v) or (vi):

(v) $R^{17}$ and $R^{18}$ each independently denote H or $C_{1-6}$ alkyl; or (vi) $R^{17}$ and $R^{18}$ together with the nitrogen atom linking them form a heterocycle which optionally may be substituted at one or more of its carbon ring members with one or more substituents each independently selected from the group consisting of F, Cl, Br, I, —$NH_2$, —$CF_3$, =O, —O—$CF_3$, —OH, —SH, —O—$C_{1-6}$ alkyl, $C_{1-6}$ alkyl, $C_{3-8}$ cycloalkyl, aryl and heteroaryl and/or anellated with a saturated, mono- or polyunsaturated or aromatic ring system which optionally may be substituted at one or more of its carbon ring members with one or more substituents each independently selected from the group consisting of F, Cl, Br, I, —$NH_2$, —$CF_3$, =O, —O—$CF_3$, —OH, —SH, —O—$C_{1-6}$ alkyl, $C_{1-6}$ alkyl, $C_{3-8}$ cycloalkyl, aryl and heteroaryl, wherein said heterocycle is saturated or mono- or polyunsaturated, but not aromatic, is 4-, 5-, 6- or 7-membered, and in addition to the N-heteroatom to which $R^8$ and $R^9$ are bound optionally may also contain at least one further heteroatom or a heteroatom group selected from the group consisting of N, $NR^{19}$, O, S, S=O and $S(=O)_2$, the ring system is 4-, 5-, 6- or 7-membered, optionally may contain at least one heteroatom or a heteroatom group selected from the group consisting of N, $NR^{20}$, O, S, S=O and $S(=O)_2$, $R^{19}$ denotes a substituent selected from the group consisting of H, $C_{1-6}$ alkyl, $C_{3-8}$ cycloalkyl, aryl, heteroaryl or for an aryl, heteroaryl or $C_{3-8}$ cycloalkyl bonded via a $C_{1-3}$ alkylene group, and $R^{20}$ denotes a substituent selected from the group consisting of H, $C_{1-6}$ alkyl, $C_{3-8}$ cycloalkyl, aryl, heteroaryl or for an aryl, heteroaryl or $C_{3-8}$ cycloalkyl group bonded via a $C_{1-3}$ alkylene group;

wherein the aforementioned $C_{1-6}$ alkyl, $C_{2-6}$ alkenyl, $C_{1-3}$ alkylene, $C_{1-6}$ alkylene, $C_{2-6}$ alkenylene, carbocyclyl, 3- to 8-membered heterocycloalkyl, $C_{3-8}$ cycloalkyl, aryl and heteroaryl groups may each be unsubstituted or mono- or polysubstituted with identical or different substituents, and the aforementioned $C_{1-6}$ alkyl, $C_{2-6}$ alkenyl, $C_{1-3}$ alkylene, $C_{1-6}$ alkylene and $C_{2-6}$ alkenylene groups can each be branched or unbranched;

optionally in the form of a single enantiomer or a single diastereomer, the racemate, the enantiomers, the diastereomers, mixtures of enantiomers and/or diastereomers, and each in the form of their bases and/or physiologically compatible salts.

As used herein the term "isolated" used with respect to a stereoisomer means substantially separated from other stereoisomers but not necessarily from other substances.

Within the meaning of the present invention the term "halogen" preferably denotes F, Cl, Br and I, in particular F and Cl.

Within the meaning of this invention, the expression "$C_{1-6}$ alkyl" includes acyclic saturated hydrocarbon groups having 1, 2, 3, 4, 5 or 6 carbon atoms, which may be branched or straight-chain (unbranched) and unsubstituted or mono- or polysubstituted, for example di-, tri-, tetra- or pentasubstituted, with identical or different substituents. The alkyl groups are preferably selected from the group consisting of methyl, ethyl, n-propyl, isopropyl, n-butyl, isobutyl, sec-butyl, tert-butyl, n-pentyl, isopentyl, neopentyl and hexyl. Particularly preferred alkyl groups include methyl, ethyl, n-propyl, isopropyl, n-butyl, sec-butyl, isobutyl and tert-butyl.

Within the meaning of this invention, the expression "$C_{2-6}$ alkenyl" includes acyclic unsaturated hydrocarbon groups having 2, 3, 4, 5 or 6 carbon atoms, which may be branched or straight-chain (unbranched) and unsubstituted or mono- or polysubstituted, for example di-, tri-, tetra- or pentasubstituted, with identical or different substituents. The alkenyl groups include at least one C=C double bond. Alkenyl groups are preferably selected from the group consisting of vinyl, prop-1-enyl, allyl, 2-methylprop-1-enyl, but-1-enyl, but-2-enyl, but-3-enyl, but-1,3-dienyl, 2-methylprop-1-enyl, but-2-en-2-yl, but-1-en-2-yl, pentenyl and hexenyl. Particularly preferred alkenyl groups include vinyl, prop-1-enyl, allyl, 2-methylprop-1-enyl, but-1-enyl, but-2-enyl, but-3-enyl, but-1,3-dienyl, 2-methylprop-1-enyl, but-2-en-2-yl and but-1-en-2-yl groups.

Within the meaning of this invention, the expression "$C_{3-8}$ cycloalkyl" denotes cyclic saturated hydrocarbons having 3, 4, 5, 6, 7 or 8 carbon atoms, which may be unsubstituted or mono- or polysubstituted, for example di-, tri-, tetra- or pentasubstituted, at one or more ring members with identical or different substituents. $C_{3-8}$ cycloalkyl groups are preferably selected from the group consisting of cyclopropyl, cyclobutyl, cyclopentyl, cyclohexyl, cycloheptyl and cyclooctyl.

The expression "3- to 8-membered heterocycloalkyl" denotes saturated heterocycles which include 1, 2, 3, 4 or 5 independently selected, identical or different heteroatoms as ring members, preferably selected from the group consisting of N, O and S. If the heterocycloalkyl group is bound to a heteroatom, for example N, the binding to the heterocycloalkyl is preferably made via one of the carbon ring members of the heterocycloalkyl group. 3- to 8-membered heterocycloalkyl groups may in particular be 4-, 5- or 6-membered. Examples of 3- to 8-membered heterocycloalkyl groups include azetidinyl, pyrrolidinyl, piperidinyl, piperazinyl, morpholinyl, thiamorpholinyl, tetrahydropyranyl, dioxanyl and dioxolanyl, which optionally may be substituted as described below.

Within the meaning of this invention, the expression "aryl" denotes aromatic hydrocarbons, in particular phenyls and naphthyls. The aryl groups optionally may also be fused with other saturated, (partially) unsaturated or aromatic ring systems. Each aryl group may be present in unsubstituted or mono- or polysubstituted form, for example di-, tri-, tetra- or pentasubstituted, wherein the aryl substituents may be identical or different and can be at any desired and possible position of the aryl group. Aryl can advantageously be selected from the group consisting of phenyl, 1-naphthyl and 2-naphthyl, which may be unsubstituted or mono- or polysubstituted, for example with 2, 3, 4 or 5 substituents.

Within the meaning of the present invention, the expression "heteroaryl" denotes a 5-, 6- or 7-membered cyclic aromatic group containing at least 1, optionally also 2, 3, 4 or 5 heteroatoms, wherein the heteroatoms may be identical or different and the heteroaryl group may be unsubstituted or mono- or polysubstituted, for example di-, tri-, tetra- or pentasubstituted, with identical or different substituents. The substituents can be bound to any desired and possible position of the heteroaryl group. The heterocycle can also be part of a bicyclic or polycyclic ring system, in particular a mono-, bi- or tricyclic ring system, which can then in total be more than 7-membered, for example up to 14-membered. Preferred heteroatoms are selected from the group consisting of N, O and S. Heteroaryl groups are preferably selected from the group consisting of pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, benzooxazolyl, benzoxadiazolyl, imidazothiazolyl, dibenzofuranyl, dibenzothienyl, phthalazinyl, pyrazolyl, imidazolyl, thiazolyl, oxazolyl, oxadiazolyl, triazole, tetrazole, isoxazoyl, pyridinyl (pyridyl), pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, in particular from the group consisting of thienyl (thiophenyl), pyridinyl (pyridyl), pyrimidinyl, thiazolyl, triazolyl, imidazolyl, oxazolyl, quinazolinyl, quinolinyl and isoquinolinyl, wherein the binding to the general structure (I) can be made via any desired and possible ring member of the heteroaryl group. The heteroaryl group is particularly preferably selected from the group consisting of quinolinyl, isoquinolinyl, thienyl, imidazolyl, thiazolyl, triazolyl and pyridinyl.

Within the meaning of the present invention, the expression "bicyclic 8-12-membered carbocyclyl" denotes annular hydrocarbon groups consisting of two fused ring systems, wherein the two ring systems together have 8-12 ring members and no heteroatoms. The two ring systems may have different ring sizes and different degrees of saturation. This means that the two ring systems can each be aromatic, saturated or partially unsaturated. In particular, bicyclic 8-12-membered carbocyclic compounds are understood to be compounds consisting of an aromatic ring system fused with a saturated ring system. The binding to the general structure (I) can be made via any desired and possible ring member of the carbocyclyl ring system, but preferably via a ring member of an unsaturated ring. The bicyclic 8-12-membered carbocyclyl group is particularly preferably selected from the group consisting of 2,3-dihydro-1H-indenyl and 1,2,3,4-tetrahydronaphthyl.

Within the meaning of the present invention, the expression "$C_{1-3}$ alkylene group" or "$C_{1-6}$ alkylene group" includes acyclic saturated hydrocarbon radicals having respectively 1, 2 or 3 or 1, 2, 3, 4, 5 or 6 carbon atoms, which may be branched or straight-chain (unbranched) and unsubstituted or mono- or polysubstituted, for example di-, tri-, tetra- or pentasubstituted, with identical or different substituents and which link a corresponding group to the main structure. The alkylene groups are preferably selected from the group consisting of —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)—, —C(CH$_3$)(CH$_2$CH$_3$)—, —CH$_2$—(CH$_2$)$_3$—CH$_2$—, —CH(CH$_3$)—CH$_2$—CH$_2$—CH$_2$—, —CH$_2$—CH(CH$_3$)—CH$_2$—CH$_2$—, —CH(CH$_3$)—CH$_2$—CH(CH$_3$)—, —CH(CH$_3$)—CH(CH$_3$)—CH$_2$—, —C(CH$_3$)$_2$—CH$_2$—CH$_2$—, —CH$_2$—C(CH$_3$)$_2$—CH$_2$—, —CH(CH$_2$CH$_3$)—CH$_2$—CH$_2$—, —CH$_2$—CH(CH$_2$CH$_3$)—CH$_2$—, —$C(CH_3)_2$— —$CH(CH_3)$—, —$CH(CH_2CH_3)$—$CH(CH_3)$—, —$C(CH_3)(CH_2CH_3)$—$CH_2$—, —$CH(CH_2CH_2CH_3)$—$CH_2$—, —$C(CH_2CH_2CH_3)$—$CH_2$—, —$CH(CH_2CH_2CH_3)$—, —$C(CH_3)(CH_2CH_2CH_3)$—, —$C(CH_2CH_3)_2$— and —$CH_2$—$(CH_2)_4$—$CH_2$—. The alkylene groups are particularly preferably selected from the group consisting of —$CH_2$—, —$CH_2$—$CH_2$— and —$CH_2$—$CH_2$—$CH_2$—.

Within the meaning of the present invention, the expression "$C_{2-6}$ alkenylene group" includes acyclic mono- or polyunsaturated, for example di-, tri- or tetraunsaturated, hydrocarbon groups having 2, 3, 4, 5 or 6 carbon atoms, which may be branched or straight-chain (unbranched) and unsubstituted or mono- or polysubstituted, for example di-, tri-, tetra- or pentasubstituted, with identical or different substituents and which link a corresponding group to the main structure. The alkenylene groups include at least one C=C double bond. The alkenylene groups are preferably selected from the group consisting of —CH=CH—, —CH=CH—$CH_2$—, —$C(CH_3)$=$CH_2$—, —CH=CH—$CH_2$—$CH_2$—, —$CH_2$—CH=CH—$CH_2$—, —CH=CH—CH=CH—, —$C(CH_3)$=CH—$CH_2$—, —CH=$C(CH_3)$—$CH_2$—, —$C(CH_3)$=$C(CH_3)$—, —$C(CH_2CH_3)$=CH—, —CH=CH—$CH_2$—$CH_2$—$CH_2$—, —$CH_2$—CH=$CH_2$—$CH_2$—$CH_2$—, —CH=CH—CH—$CH_2$—$CH_2$— and —CH=$CH_2$—CH—CH=$CH_2$—.

Within the meaning of the present invention, the expression "aryl or heteroaryl group bonded via a $C_{1-3}$ alkylene group, a $C_{1-6}$ alkylene group or $C_{2-6}$ alkenylene group" means that the $C_{1-3}$ alkylene groups, $C_{1-6}$ alkylene groups and $C_{2-6}$ alkenylene groups and aryl or heteroaryl groups have the meanings defined above and the aryl or heteroaryl group is bound to the main structure by a $C_{1-3}$ alkylene group, $C_{1-6}$ alkylene group or $C_{2-6}$ alkenylene group. Examples of such groups include benzyl, phenethyl and phenylpropyl groups.

Within the meaning of the present invention, the expression "$C_{3-8}$ cycloalkyl, carbocyclyl and heterocycloalkyl bonded via a $C_{1-3}$ alkylene group, $C_{1-6}$ alkylene group or $C_{2-6}$ alkenylene group" means that the $C_{1-3}$ alkylene group, $C_{1-6}$ alkylene group, $C_{2-6}$ alkenylene group, $C_{3-8}$ cycloalkyl, carbocyclyl and heterocycloalkyl have the meanings defined above and $C_{3-8}$ cycloalkyl, carbocyclyl or heterocycloalkyl group is bonded to the main structure via a $C_{1-3}$ alkylene group, $C_{1-6}$ alkylene group or $C_{2-6}$ alkenylene group.

In connection with "alkyl", "alkenyl", "alkylene", "alkenylene" and "cycloalkyl", the term "substituted" within the meaning of this invention is understood to mean the replacement of a hydrogen with F, Cl, Br, I, $CF_3$, $OCF_3$, CN, $NH_2$, NH—$C_{1-6}$ alkyl, NH—$C_{1-6}$ alkylene-OH, $C_{1-6}$ alkyl, N($C_{1-6}$ alkyl)$_2$, N($C_{1-6}$ alkylene-OH)$_2$, $NO_2$, SH, S—$C_{1-6}$ alkyl, S-benzyl, O—$C_{1-6}$ alkyl, OH, O—$C_{1-6}$ alkylene-OH, =O, O-benzyl, C(=O)$C_{1-6}$ alkyl, $CO_2H$, $CO_2$—$C_{1-6}$ alkyl, phenyl, phenoxy, benzyl, naphthyl, furyl, thienyl or pyridinyl, wherein polysubstituted groups are understood to mean groups which are substituted multiple times, for example twice or three times, at different or the same atoms, for example substituted three times at the same carbon atom, as in $CF_3$ or —$CH_2CF_3$, or at different sites, as in CH(Cl)—CH=CH—$CHCl_2$. The polysubstitution can occur with identical or different substituents, as for example in CH(OH)—CH=CH—$CHCl_2$. It should be understood in particular to be the replacement of one or more hydrogens with F, Cl, $CF_3$, $NH_2$, OH, phenyl, O—$CF_3$ or O—$C_{1-6}$ alkyl, in particular methoxy.

In connection with "aryl" and "heteroaryl", the term "substituted" within the meaning of this invention is understood to mean the mono- or polysubstitution, for example the di-, tri-, tetra- or pentasubstitution, of one or more hydrogen atoms of the corresponding ring system with F, Cl, Br, I, CN, $NH_2$, NH—$C_{1-6}$ alkyl, NH—$C_{1-6}$ alkylene-OH, N($C_{1-6}$ alkyl)$_2$, N($C_{1-6}$ alkylene-OH)$_2$, NH-aryl$^1$, N(aryl$^1$)$_2$, N($C_{1-6}$ alkyl) aryl$^1$, pyrrolinyl, piperazinyl, morpholinyl, ($C_{1-3}$ alkylene)-azetidinyl, ($C_{1-3}$ alkylene)-pyrrolinyl or ($C_{1-3}$ alkylene)-piperidinyl, $NO_2$, SH, S—$C_{1-6}$ alkyl, OH, O—$C_{1-6}$ alkyl, O—$C_{1-6}$ alkyl-OH, C(=O)$C_{1-6}$ alkyl, $NHSO_2C_{1-6}$ alkyl, $NHCOC_{1-6}$ alkyl, $CO_2H$, $CH_2SO_2$ phenyl, $CO_2$—$C_{1-6}$ alkyl, $OCF_3$, $CF_3$, —O—$CH_2$—O—, —O—$CH_2$—$CH_2$—O—, —O—$C(CH_3)_2$—$CH_2$—, unsubstituted $C_{1-6}$ alkyl, pyrrolidinyl, imidazolyl, piperidinyl, benzyloxy, phenoxy, phenyl, naphthyl, pyridinyl, —$C_{1-3}$ alkylene-aryl$^1$, benzyl, thienyl, furyl, wherein aryl$^1$ denotes phenyl, furyl, thienyl or pyridinyl, at one or different atoms, wherein the aforementioned substituents—unless otherwise specified—can themselves be substituted with the cited substituents. The polysubstitution of aryl and heteroaryl can occur with identical or different substituents. Preferred substituents for aryl and heteroaryl are selected from the group consisting of —O—$C_{1-3}$ alkyl, unsubstituted $C_{1-6}$ alkyl, F, Cl, Br, I, CN, $CF_3$, $OCF_3$, OH, SH, —$CH_2$ azetidinyl, phenyl, naphthyl, furyl, thienyl and pyridinyl, in particular from the group consisting of F, Cl, Br, CN, $CF_3$, $CH_3$; $OCH_3$ and $OCF_3$.

In connection with "3- to 8-membered heterocycloalkyl", the term "substituted" is understood to mean the replacement of a hydrogen at one or more ring members with F, Cl, Br, I, —CN, $NH_2$, NH—$C_{1-6}$ alkyl, NH—$C_{1-6}$ alkylene-OH, $C_{1-6}$ alkyl, N($C_{1-6}$ alkyl)$_2$, N($C_{1-6}$ alkylene-OH)$_2$, pyrrolinyl, piperazinyl, morpholinyl, $NO_2$, SH, S—$C_{1-6}$ alkyl, S-benzyl, O—$C_{1-6}$ alkyl, OH, O—$C_{1-6}$ alkylene-OH, =O, O-benzyl, C(=O)$C_{1-6}$ alkyl, $CO_2H$, $CO_2$—$C_{1-6}$ alkyl or benzyl. The polysubstitution can occur with identical or different substituents. A hydrogen bound to an N ring member can be replaced by a $C_{1-6}$ alkyl, $C_{3-8}$ cycloalkyl, aryl, heteroaryl or a $C_{3-8}$ cycloalkyl, aryl or heteroaryl group bonded via a $C_{1-3}$ alkylene group, wherein these alkyl, cycloalkyl, alkylene and aryl and heteroaryl groups can be unsubstituted or substituted as defined above. Examples of substituted 3- to 8-membered heterocycloalkyl groups include 1-methylpiperidin-4-yl, 1-phenylpiperidin-4-yl, 1-benzylpiperidin-4-yl, 1-methylpyrrolidin-3-yl, 1-phenylpyrrolidin-3-yl, 1-benzylpyrrolin-3-yl, 1-methylazetidin-3-yl, 1-phenyl-azetidin-3-yl and 1-benzylazetidin-3-yl groups.

In connection with "bicyclic 8-12-membered carbocyclyl", the term "substituted" within the meaning of this invention is understood to mean the mono- or polysubstitution of hydrogen atoms of the corresponding ring systems of the bicyclic carbocyclyl systems. The substituents, which are bound to a saturated or partially unsaturated ring of the carbocyclyl system, are each independently selected from the group of substituents defined above for cycloalkyl, in other words from the group consisting of F, Cl, Br, I, $CF_3$, $OCF_3$, CN, $NH_2$, NH—$C_{1-6}$ alkyl, NH—$C_{1-6}$ alkylene-OH, $C_{1-6}$ alkyl, N($C_{1-6}$ alkyl)$_2$, N($C_{1-6}$ alkylene-OH)$_2$, $NO_2$, SH, S—$C_{1-6}$ alkyl, S-benzyl, O—$C_{1-6}$ alkyl, OH, O—$C_{1-6}$ alkylene-OH, =O, O-benzyl, C(=O)$C_{1-6}$ alkyl, $CO_2H$, $CO_2$—$C_{1-6}$ alkyl, phenyl, phenoxy, benzyl, naphthyl, furyl, thienyl and pyridinyl, wherein in the case of a polysubstitution, multiple hydrogen atoms of one ring member and/or one hydrogen atom at multiple ring members can be replaced. Substituents which are bound to an aromatic ring of the carbocyclyl system are each independently selected from the group of substituents defined above for aryl or heteroaryl, in other words from the group consisting of F, Cl, Br, I, CN, $NH_2$, NH—$C_{1-6}$ alkyl, NH—$C_{1-6}$ alkylene-OH, N($C_{1-6}$ alkyl)$_2$, N($C_{1-6}$ alkylene-OH)$_2$, NH aryl$^1$, N(aryl$^1$)$_2$, N($C_{1-6}$ alkyl)

aryl¹, pyrrolinyl, piperazinyl, morpholinyl, ($C_{1-3}$ alkylene)-azetidinyl, -pyrrolinyl or -piperidinyl, $NO_2$, SH, S—$C_{1-6}$ alkyl, OH, O—$C_{1-6}$ alkyl, O—$C_{1-6}$ alkyl-OH, C(=O)$C_{1-6}$ alkyl, $NHSO_2C_{1-6}$ alkyl, $NHCOC_{1-6}$ alkyl, $CO_2H$, $CH_2SO_2$ phenyl, $CO_2$—$C_{1-6}$ alkyl, $OCF_3$, $CF_3$, —O—$CH_2$—O—, —O—$CH_2$—$CH_2$—O—, —O—C($CH_3$)$_2$—$CH_2$—, unsubstituted $C_{1-6}$ alkyl, pyrrolidinyl, imidazolyl, piperidinyl, benzyloxy, phenoxy, phenyl, naphthyl, pyridinyl, —$C_{1-3}$ alkylene-aryl¹, benzyl, thienyl, furyl, wherein aryl¹ denotes phenyl, furyl, thienyl and pyridinyl, wherein the aforementioned substituents—unless otherwise specified—can themselves be substituted with the cited substituents. The polysubstitution can be performed with identical or different substituents. Preferred substituents are selected from the group consisting of —O—$C_{1-3}$ alkyl, unsubstituted $C_{1-6}$ alkyl, F, Cl, Br, I, CN, $CF_3$, $OCF_3$, OH, SH, —$CH_2$ azetidinyl, phenyl, naphthyl, furyl, thienyl and pyridinyl, in particular from the group consisting of F, Cl, Br, CN, $CF_3$, $CH_3$; $OCH_3$, $OCF_3$ and —$CH_2$-azetidinyl.

In the chemical structural formulas which are used here to describe the compounds according to the invention, the symbol

is also used to describe one or more substitution models, wherein unlike the representation of a binding to a specific atom, this group is not bound to a specific atom within the chemical structural formula ($R^a$ stands by way of example here for a substituent R having a number represented by the variable "a"). This can be explained by way of example by reference to the group

from the general formula (I) shown above: The definition for $R^{10}$ indicates that $R^{10}$ can stand for 0 to 4 substituents. Thus $R^{10}$ can be absent, or 1, 2, 3 or 4 of the C-bound hydrogen atoms within the substructure represented by the general formula (I) can be replaced by one of the substituents listed in the definition of $R^{10}$, wherein each of the substituents can be selected independently, in other words they can have different meanings, and C-bound hydrogen atoms can be replaced at one or more C atoms. As indicated in the definition of $R^{200}$, for example, two of the $R^{200}$ substituents can together represent an anellated aryl or heteroaryl ring (also referred to as a fused aryl or heteroaryl or anellated/fused aryl or heteroaryl group).

In the context of the present invention, the symbol

used in formulas represents a linking of a corresponding radical to the main structure. The person skilled in the art understands that identical radicals used for the definition of different substituents are mutually independent.

If two substituent groups form a (hetero)cyclic ring with an atom or group linking them, which ring can be substituted at one or more of its carbon ring members with one or more substituents, this polysubstitution can take place for example at 2, 3 or 4 ring members, in particular with 2, 3, 4 or 5 substituents.

Within the meaning of this invention the term "physiologically compatible salt" is understood to mean preferably salts of the compounds according to the invention with inorganic or organic acids, which are physiologically compatible, particularly when used in humans and/or mammals. Examples of suitable acids include hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro-1$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric acid and/or aspartic acid. The salts of hydrochloric acid (hydrochlorides) and of citric acid (citrates) are particularly preferred.

In the compounds according to the invention $R^1$ preferably denotes phenyl, naphthyl, indolyl, benzofuranyl, benzothiophenyl (benzothienyl); benzooxazolyl, benzoxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl (dibenzothienyl), quinolinyl, isoquinolinyl, CH(phenyl)$_2$ or a phenyl or naphthyl group bonded via a $C_{1-3}$ alkylene group, particularly preferably for phenyl, naphthyl, benzothiophenyl (benzothienyl), benzoxadiazolyl, quinolinyl, isoquinolinyl, thienyl or a phenyl group bonded via a $C_{1-3}$ alkylene group, most particularly preferably for phenyl, naphthyl, benzothiophenyl (benzothienyl) or a phenyl group bonded via a $C_{1\ or\ 2}$ alkylene group, wherein the aforementioned aryl or heteroaryl groups are each unsubstituted or mono- or polysubstituted, equally or differently, wherein the substituents are each selected independently from the group consisting of —O—$C_{1-3}$ alkyl, $C_{1-6}$ alkyl, $C_{3-6}$ cycloalkyl, F, Cl, Br, $CF_3$, $OCF_3$, OH, phenyl, phenoxy, naphthyl, thiazolyl, thienyl and pyridinyl.

$R^1$ can stand in particular for phenyl or naphthyl, wherein the phenyl or naphthyl is unsubstituted or mono- or polysubstituted, for example di-, tri-, tetra- or pentasubstituted, with identical or different substituents selected from methyl, methoxy, $CF_3$, $OCF_3$, F, and Cl.

In likewise preferred embodiments of the compounds according to the invention $R^1$ is selected from 4-methoxy-2,3,6-trimethylphenyl, 4-methoxy-2,6-dimethylphenyl, 2,4,6-trimethylphenyl, 2,6-dichloro-4-(trifluoromethyl)phenyl, 2-chloro-6-methylphenyl, 2,4,6-trichlorophenyl, 2,6-dichloro-4-methoxyphenyl, 2,6-dichlorophenyl, 2,6-dichloro-3-methylphenyl, 6-methoxy-2-naphthyl, 2-methyl-1-naphthyl, 2-chloro-1-naphthyl, 2-fluoro-1-naphthyl, 2-chloro-4-(trifluoromethoxy)phenyl, 4-chloro-2,5-dimethylphenyl, 2,3-dichlorophenyl, 3,4-dichlorophenyl, 2,4-dichlorophenyl, 2-(trifluoromethyl)phenyl, 3-(trifluoromethyl)phenyl, 4-(trifluoromethyl)phenyl, 4-fluoro-1-naphthyl, 4-methoxy-1-naphthyl, 1-naphthyl and 2-naphthyl; in particular 4-methoxy-2,6-dimethylphenyl and 2-chloro-6-methylphenyl.

In likewise preferred embodiments of the compounds according to the invention according to the general formula (I), the substructure (Ac I) illustrated below (Ac I)

represents a group according to the general formula (Ac I.a)

(Ac I.a.)

wherein r denotes 0, 1 or 2;

r1 denotes 0, 1, 2 or 3;

r2 denotes 0, 1 or 2;

q denotes 0 or 1;

with the proviso that $r+r1+r2+q \geq 2$;

A denotes $CH_2$, $NR^{12}$, O, S, S=O or $S(=O)_2$, and $R^{200}$ denotes 0 to 4 substituents each independently selected from the group consisting of F, Cl, $-CF_3$, =O, $-O-CF_3$, $-OH$, $-O-C_{1-6}$ alkyl or $C_{1-6}$ alkyl, in particular F or $CF_3$, or two $R^{200}$ groups together represent an anellated, optionally substituted aryl or heteroaryl group, in particular an optionally substituted benzo group.

If the structure of the N-containing heterocycle allows it, $R^{200}$ can thus also stand for two aryl groups, in particular benzo groups, anellated to the heterocycle. In certain embodiments $R^{200}$ denotes 0 substituents and is therefore absent.

The substructure Ac I can in particular stand for one of the following groups:

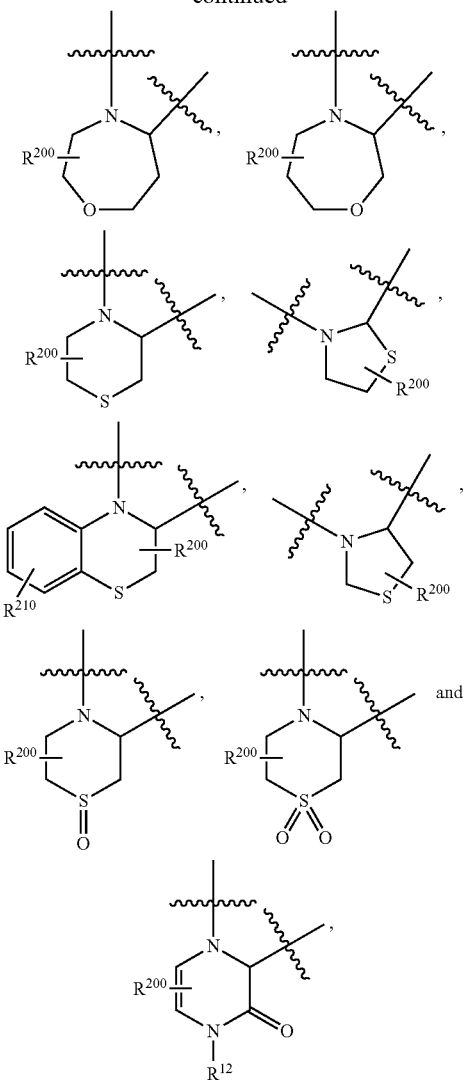

wherein

R²⁰⁰ denotes 0 to 4 substituents each independently selected from the group consisting of F, Cl, —CF₃, =O, —O—CF₃, —OH, —O—C₁₋₆ alkyl and C₁₋₆ alkyl, in particular F or CF₃, and/or two adjacent R²⁰⁰ groups together form an anellated aryl or heteroaryl group, in particular a benzo group;

R²¹⁰ denotes 0 to 4 substituents each independently selected from the group consisting of —O—C₁₋₃ alkyl, C₁₋₆ alkyl, F, Cl, Br, I, CF₃, OCF₃, OH, SH, phenyl, naphthyl, furyl, thienyl and pyridinyl, in particular methyl, methoxy, CF₃, OCF₃, F, Cl or Br;

R¹² denotes H, C₁₋₆ alkyl, —C(=O)—R¹³, C₃₋₈ cycloalkyl, aryl, heteroaryl or a C₃₋₈ cycloalkyl, aryl or heteroaryl group bonded via a C₁₋₃ alkylene group, and R¹³ denotes C₁₋₆ alkyl, C₃₋₈ cycloalkyl, aryl, heteroaryl or a C₃₋₈ cycloalkyl, aryl or heteroaryl group bonded via a C₁₋₃ alkylene group.

In certain embodiments of the compounds according to the invention R²⁰⁰ and/or R²¹⁰ stand for 0 substituents and are therefore absent.

The substructure Ac I can in particular stand for one of the following groups:

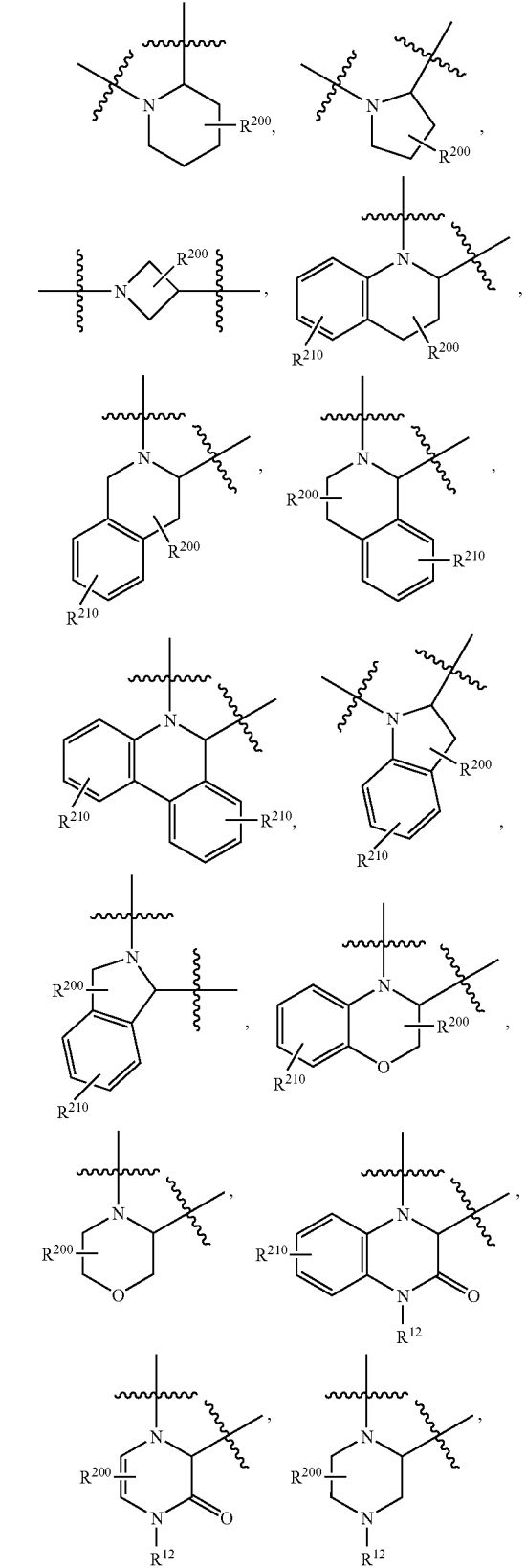

-continued

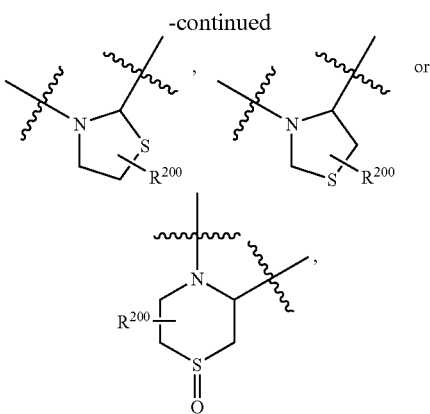

wherein $R^{200}$, $R^{210}$ and $R^{12}$ preferably have the meanings described above.

In a likewise preferred embodiment of the compounds according to the invention $R^2$ denotes H, $C_{1-6}$ alkyl, $C_{3-6}$ cycloalkyl, aryl, heteroaryl or a $C_{3-6}$ cycloalkyl, aryl or heteroaryl group bonded via a $C_{1-3}$ alkylene group, in each case unsubstituted or mono- or polysubstituted with identical or different substituents. In particular $R^2$ may denote H, methyl, ethyl, n-propyl, isopropyl, n-butyl, isobutyl, sec-butyl, tert-butyl, cyclopropyl, phenyl, pyridinyl or a phenyl or pyridinyl group bonded via a $C_{1-3}$ alkylene group, in each case unsubstituted or mono- or polysubstituted with identical or different substituents.

In a likewise preferred embodiment of the compounds according to the invention $R^3$ denotes H, F, Cl, —$CF_3$, —OH, —O—$C_{1-6}$ alkyl, $C_{1-6}$ alkyl, aryl or heteroaryl or an aryl or heteroaryl group bonded via a $C_{1-3}$ alkylene group, in each case unsubstituted or mono- or polysubstituted with identical or different substituents. In particular $R^3$ may denote H, methyl, ethyl, n-propyl, isopropyl, n-butyl, isobutyl, sec-butyl, tert-butyl, phenyl or pyridinyl.

In a further preferred embodiment of the compounds according to the invention the following substructure in formula (I)

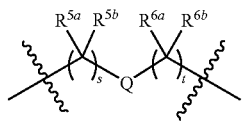

denotes a —$CH_2$—, —$(CH_2)_2$—, —$(CH_2)_3$—, —$(CH_2)_4$— or —$CH_2$—O—$CH_2$— group.

Also preferred are embodiments of the compounds according to the invention in which $R^{4a}$, $R^{4b}$, $R^{5a}$, $R^{5b}$, $R^{6a}$ and $R^{6b}$ are each independently selected from the group consisting of H, F, Cl, —$CF_3$, OH, $OCF_3$ and O—$C_{1-6}$ alkyl, preferably from the group consisting of H, F, Cl, $CF_3$, OH, $OCF_3$ and $OCH_3$. In particular these groups each independently represent H or F. These groups most particularly preferably denote H.

Also preferred are embodiments of the compounds according to the invention in which $R^7$ denotes phenyl, naphthyl, thienyl, thiazolyl, pyridinyl or benzyl, wherein the phenyl, naphthyl, thienyl, thiazolyl, pyridinyl or benzyl may be unsubstituted or mono- or polysubstituted with substituents independently selected from the group consisting of $C_{1-4}$ alkyl, O—$C_{1-4}$ alkyl, F, Cl, $CF_3$, $OCF_3$ and —CN.

Likewise preferred embodiments of the compounds according to the invention are those in which $R^8$ and $R^9$ each independently denote H, or unsubstituted or mono- or polysubstituted $C_{1-6}$ alkyl, in particular a group selected from the group consisting of H, methyl, ethyl, n-propyl, isopropyl, n-butyl, isobutyl, sec-butyl and tert-butyl. The two groups $R^8$ and $R^9$ most particularly preferably denote H or methyl.

Also preferred are embodiments of the compounds according to the invention in which $R^8$ and $R^9$ together with the nitrogen atom linking them form a heterocycle corresponding to the formula (II)

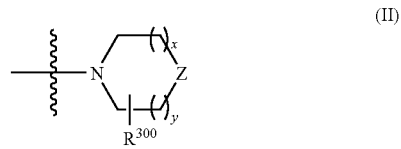

(II)

wherein

Z denotes O, S $NR^{15a}$, $CH_2$ or C(halogen)$_2$, wherein
  $R^{15a}$ denotes H; $C_{1-6}$ alkyl; aryl, preferably phenyl or naphthyl; or heteroaryl, preferably a 5- to 6-membered heteroaryl having 1 or 2 N heteroatoms, in particular pyridinyl; or
  $R^{15a}$ denotes an aryl, preferably phenyl or naphthyl, bonded via a $C_{1-3}$ alkylene group; or for a heteroaryl, preferably a 5- to 6-membered heteroaryl having 1 or 2 N heteroatoms, in particular pyridinyl, bonded via a $C_{1-3}$ alkylene group, x and y, each independently represent 0, 1 or 2, with the proviso that x+y=0, 1, 2 or 3, and $R^{300}$ denotes 0 to 4 substituents each independently selected from the group consisting of $C_{1-6}$ alkyl, —O—$C_{1-6}$ alkyl, OH, $CF_3$, F, aryl, heteroaryl, $C_{1-3}$ alkylene-aryl and $C_{1-3}$ alkylene-heteroaryl, wherein the aforementioned $C_{1-6}$ alkyl, $C_{1-3}$ alkylene, aryl and heteroaryl groups may be unsubstituted or mono- or polysubstituted with identical or different substituents.

Further preferred embodiments of the compounds according to the invention are those in which $R^8$ and $R^9$ are defined as described in (iii) or (iv):

(iii) $R^8$ and $R^9$ each independently represent a group selected from the group consisting of H, methyl, ethyl, n-propyl, isopropyl, n-butyl, isobutyl, sec-butyl and tert-butyl, in particular both $R^8$ and $R^9$ denote methyl, or (iv) $R^8$ and $R^9$ together with the nitrogen atom linking them form a heterocycle corresponding to formula (II)

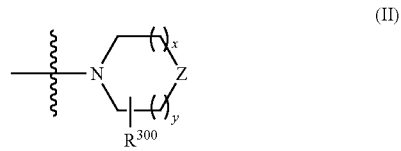

(II)

wherein

Z denotes O, S $NR^{15a}$, $CH_2$ or $CF_2$, wherein
  $R^{15a}$ denotes H; methyl, ethyl, n-propyl, isopropyl, n-butyl, isobutyl, sec-butyl, tert-butyl, phenyl, naphthyl or pyridinyl or
  $R^{15a}$ represents a phenyl, naphthyl or pyridinyl group bonded via a $C_{1-3}$ alkylene group;

x and y each independently represent 0, 1 or 2, with the proviso that x+y=0, 1, 2 or 3; and $R^{300}$ denotes 0 to 4 substituents each independently selected from the group consisting of $C_{1-6}$ alkyl, —O—$C_{1-6}$ alkyl, OH, $CF_3$, F, aryl, heteroaryl, $C_{1-3}$ alkylene-aryl and $C_{1-3}$ alkylene-heteroaryl.

In certain embodiments of the compounds according to the invention $R^{300}$ in the heterocycles corresponding to formula (II) denotes 0 substituents and is therefore absent, or denotes methyl.

In likewise preferred embodiments of the compounds according to the invention $R^{10}$ and $R^{11}$ each independently represent 0 to 4 substituents which are each independently selected from the group consisting of $C_{1-6}$ alkyl, —O—$C_{1-6}$ alkyl, OH, $CF_3$, F, aryl, heteroaryl, $C_{1-3}$ alkylene-aryl and $C_{1-3}$ alkylene-heteroaryl. In particular $R^{10}$ and $R^{11}$ can be absent or can stand for methyl.

Also preferred are embodiments of the compounds according to the invention in which the following substructure

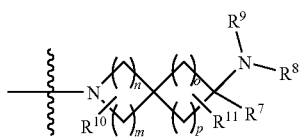

denotes one of the following groups:

A1
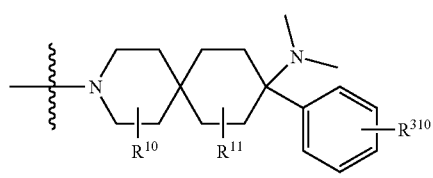

A2
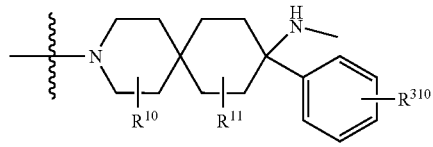

A3
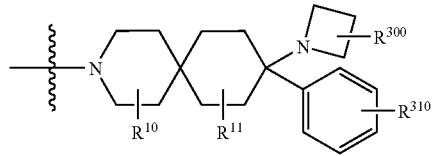

A4
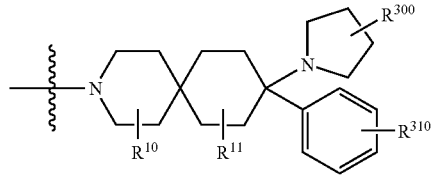

A5
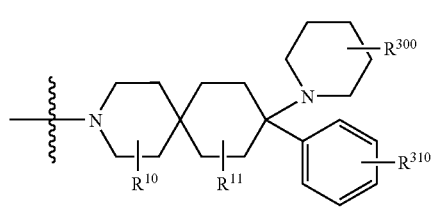

A6
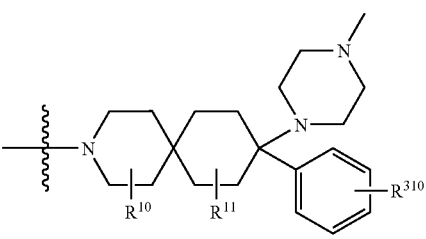

A7
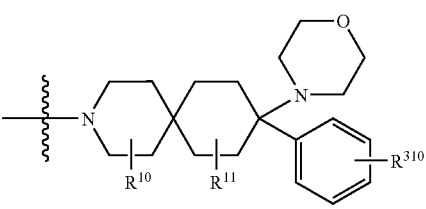

A8
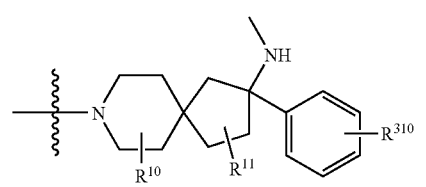

A9
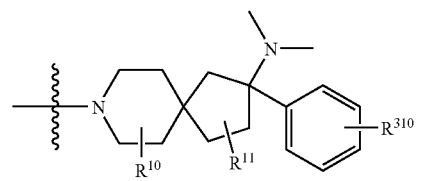

A10
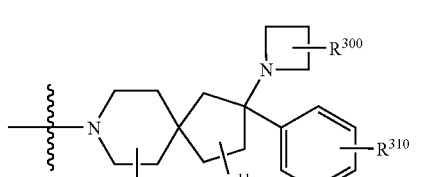

A11
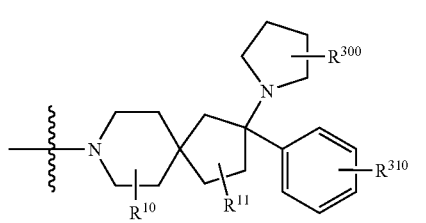

A12
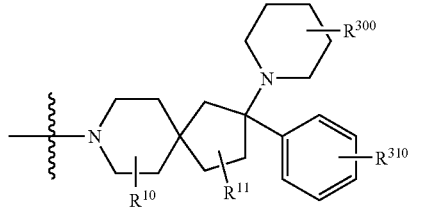

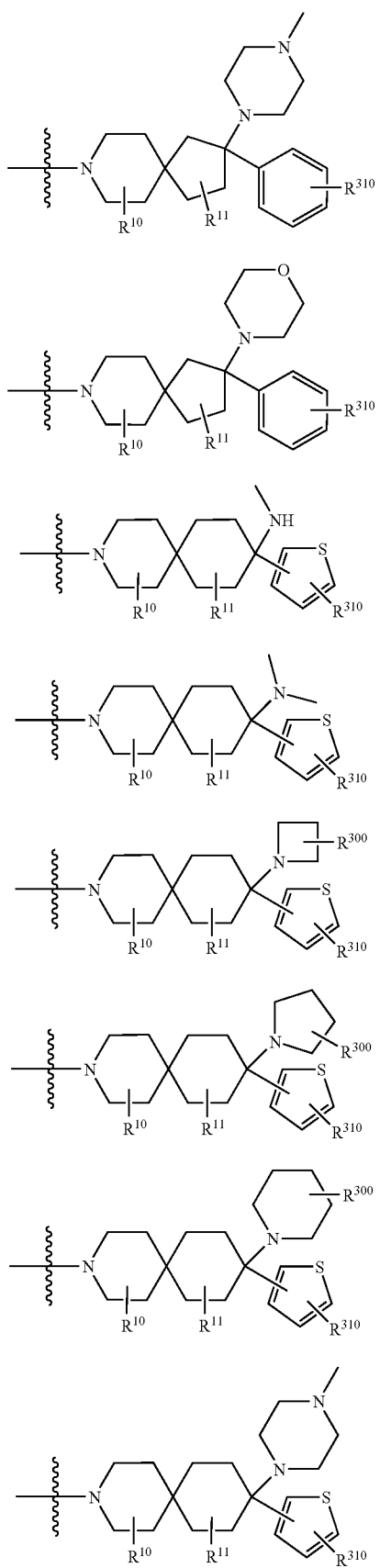
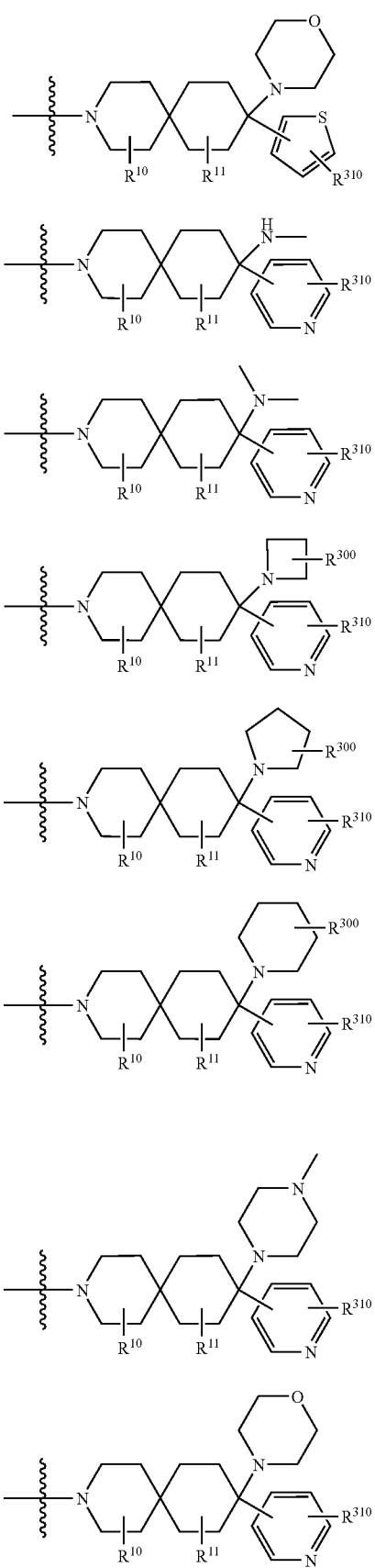

-continued

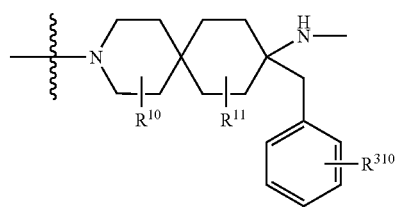
A29

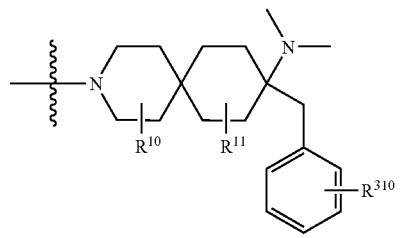
A30

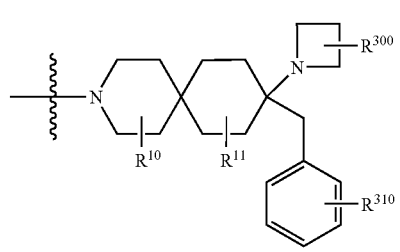
A31

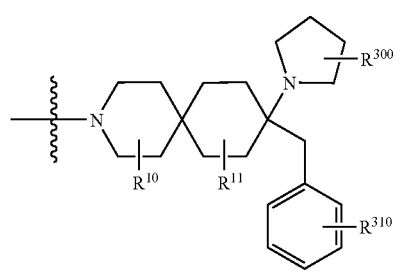
A32

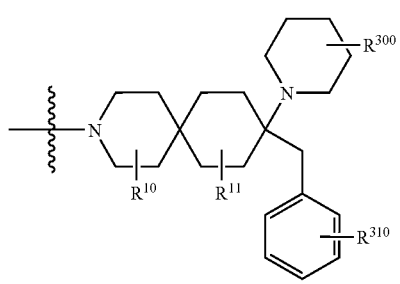
A33

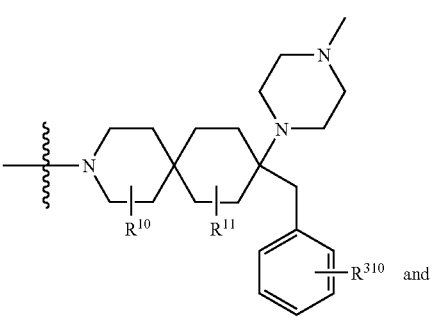
A34 and

-continued

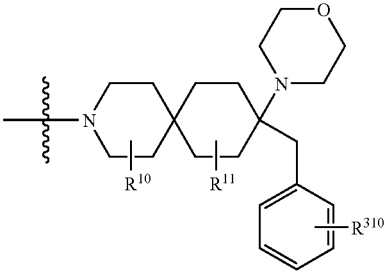
A35 wherein $R^{10}$ and $R^{11}$ each independently represent 0 to 4 substituents each independently selected from the group consisting of $C_{1-6}$ alkyl, —O—$C_{1-6}$ alkyl, OH, $CF_3$, F, aryl, heteroaryl, $C_{1-3}$ alkylene-aryl and $C_{1-3}$ alkylene-heteroaryl;

$R^{300}$ denotes 0 to 4 substituents each independently selected from the group consisting of $C_{1-6}$ alkyl, —O—$C_{1-6}$ alkyl, OH, $CF_3$, F, aryl, heteroaryl, $C_{1-3}$ alkylene-aryl and $C_{1-3}$ alkylene-heteroaryl; and $R^{310}$ denotes 0 to 4 substituents each independently selected from the group consisting of F, Cl, Br, $C_{1-6}$ alkyl, O—$C_{1-6}$ alkyl, $CF_3$, $OCF_3$ and CN.

Particularly preferred embodiments of the compounds according to the invention are those corresponding to formula (Ia)

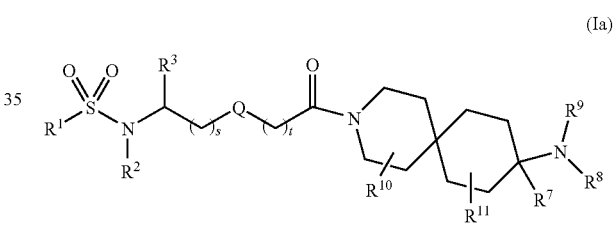
(Ia)

wherein s and t each independently represent 0, 1 or 2;

Q denotes a single bond, —O— or —$CH_2$—;

$R^1$ denotes phenyl or naphthyl, which may be unsubstituted or mono- or polysubstituted, identically or differently, with substituents independently selected from the group consisting of —O—$C_{1-3}$ alkyl, $C_{1-6}$ alkyl, F, Cl, Br, $CF_3$, $OCF_3$ and OH;

$R^2$ and $R^3$ are as defined under (i) or (ii):

(i) $R^2$ denotes H, methyl, ethyl, n-propyl, isopropyl, n-butyl, isobutyl, sec-butyl, tert-butyl, cyclopropyl, aryl, heteroaryl or $R^2$ denotes an aryl or heteroaryl group bonded via a $C_{1-3}$ alkylene group, and $R^3$ denotes H or phenyl, wherein the phenyl is unsubstituted or mono- or polysubstituted with substituents selected from the group consisting of F, Cl, —$CF_3$, —$OCF_3$, OH, methyl and methoxy, or (ii) $R^2$ and $R^3$ together with the —N—CH— group linking them form a heterocycle which optionally may be substituted at one or more of its carbon ring members with one or more substituents each independently selected from the group consisting of F, Cl, Br, I, —$NH_2$, —$CF_3$, =O, —O—$CF_3$, —OH, —SH, —O—$C_{1-6}$ alkyl, $C_{1-6}$ alkyl, $C_{3-8}$ cycloalkyl, aryl and heteroaryl and/or anellated with at least one optionally substituted aryl or heteroaryl group, wherein said heterocycle may be saturated or mono- or polyunsaturated, but is not aromatic, is 4-, 5-, 6- or 7-membered, and in addition to the N-heteroatom to which $R^2$ is bound optionally may also contain one or more heteroatoms or heteroatom groups each independently selected from the group consisting of N, $NR^{12}$, O, S, S=O and $S(=O)_2$; wherein
$R^{12}$ denotes H, $C_{1-6}$ alkyl, $-C(=O)-R^{13}$, $C_{3-8}$ cycloalkyl, aryl, heteroaryl or a $C_{3-8}$ cycloalkyl, aryl or heteroaryl group bonded via a $C_{1-3}$ alkylene group, and
$R^{13}$ denotes $C_{1-6}$ alkyl, $C_{3-8}$ cycloalkyl, aryl, heteroaryl or a $C_{3-8}$ cycloalkyl, aryl or heteroaryl group bonded via a $C_{1-3}$ alkylene group;
$R^7$ denotes phenyl, naphthyl, thienyl, thiazolyl, pyridinyl or benzyl, wherein the phenyl, naphthyl, thienyl, thiazolyl, pyridinyl or benzyl group may be unsubstituted or mono- or polysubstituted with substituents each independently selected from the group consisting of $C_{1-4}$ alkyl, $O-C_{1-4}$ alkyl, F, Cl, $CF_3$, $OCF_3$ and $-CN$,
$R^8$ and $R^9$ are as defined under (iii) or (iv):
(iii) $R^8$ and $R^9$ are each independently selected from the group consisting of H, methyl, ethyl, n-propyl, isopropyl, n-butyl, isobutyl, sec-butyl and tert-butyl, and preferably denote H or methyl, or (iv) $R^8$ and $R^9$ together with the nitrogen atom linking them form a heterocycle corresponding to formula (II)

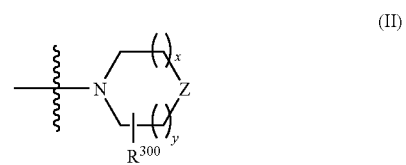

(II)

wherein
Z denotes O, S $NR^{15a}$, $CH_2$ or $CF_2$, wherein
$R^{15a}$ denotes H; methyl, ethyl, n-propyl, isopropyl, n-butyl, isobutyl, sec-butyl, tert-butyl, phenyl, naphthyl or pyridinyl, or
$R^{15a}$ represents a phenyl, naphthyl or pyridinyl group bonded via a $C_{1-3}$ alkylene group;
x and y each independently represent 0, 1 or 2, with the proviso that x+y=0, 1, 2 or 3, and
$R^{300}$ denotes 0 to 4 substituents which are each independently selected from the group consisting of F, methyl and ethyl.

Likewise preferred embodiments of the compounds according to the invention are compounds selected from the group consisting of:

| | | |
|---|---|---|
| 1 | 2-((1-(4-Methoxy-2,6-dimethylphenylsulfonyl)piperidin-2-yl)methoxy)-1-(9-phenyl-9-(pyrrolidin-1-yl)-3-azaspiro[5.5]undecan-3-yl)ethanone | 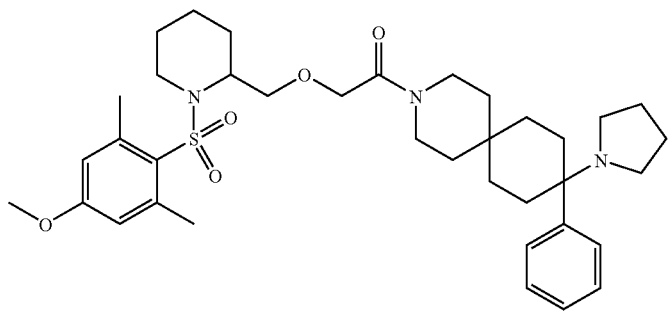 |
| 2 | 1-(9-(Dimethylamino)-9-phenyl-3-azaspiro[5.5]undecan-3-yl)-2-(((S)-1-(4-methoxy-2,6-dimethylphenylsulfonyl)piperidin-2-yl)methoxy)ethanone | 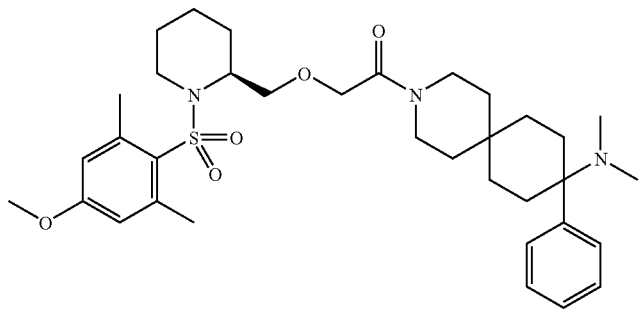 |
| 3 | N-Cyclopropyl-N-(2-(2-(9-(dimethylamino)-9-phenyl-3-azaspiro[5.5]undecan-3-yl)-2-oxoethoxy)ethyl)-4-methoxy-2,6-dimethylbenzenesulfonamide | 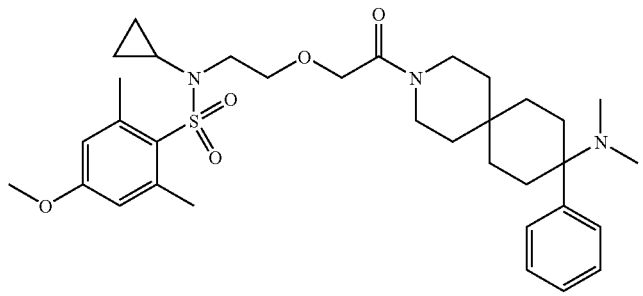 |

-continued

| | | |
|---|---|---|
| 4 | 1-(9-(Dimethylamino)-9-phenyl-3-azaspiro[5.5]undecan-3-yl)-2-(((S)-1-(4-methoxy-2,6-dimethylphenylsulfonyl)indolin-2-yl)methoxy)ethanone | 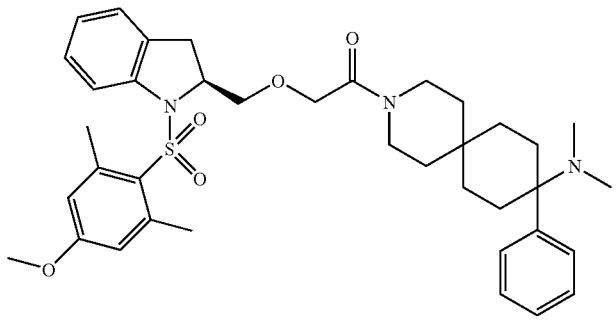 |
| 5 | N-((1R)-3-(9-(Dimethylamino)-9-phenyl-3-azaspiro[5.5]undecan-3-yl)-3-oxo-1-phenylpropyl)naphthalene-2-sulfonamide | 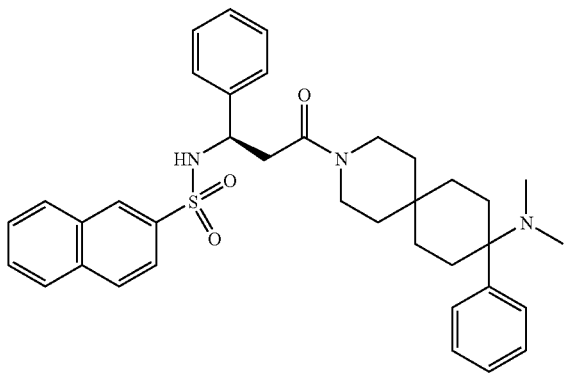 |
| 6 | 2-(((S)-1-(2-Chloro-6-methylphenylsulfonyl)piperidin-2-yl)methoxy)-1-(9-(dimethylamino)-9-phenyl-3-azaspiro[5.5]undecan-3-yl)ethanone | 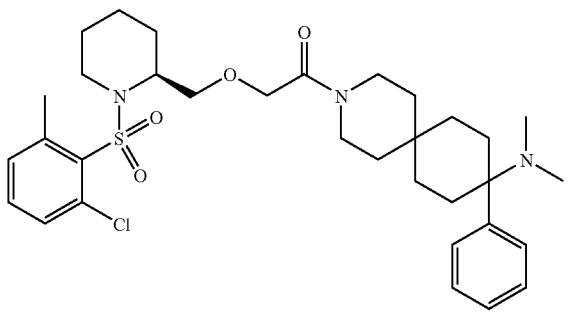 |
| 7 | 3-(1-(4-Chloro-2,5-dimethylphenylsulfonyl)piperidin-2-yl)-1-(9-(dimethylamino)-9-phenyl-3-azaspiro[5.5]undecan-3-yl)propan-1-one | 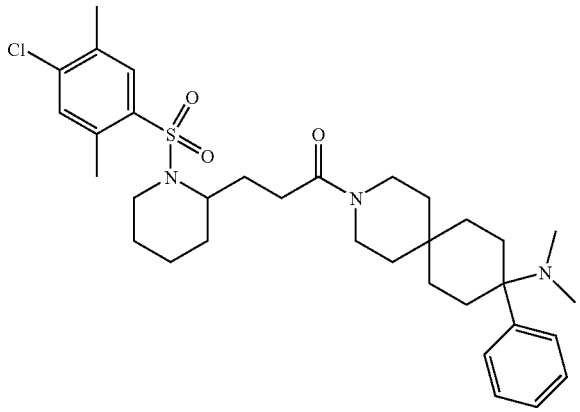 |

| | | |
|---|---|---|
| 8 | 1-(9-(Dimethylamino)-9-phenyl-3-azaspiro[5.5]undecan-3-yl)-4-(1-(4-methoxy-2,6-dimethylphenylsulfonyl)piperidin-2-yl)butan-1-one | 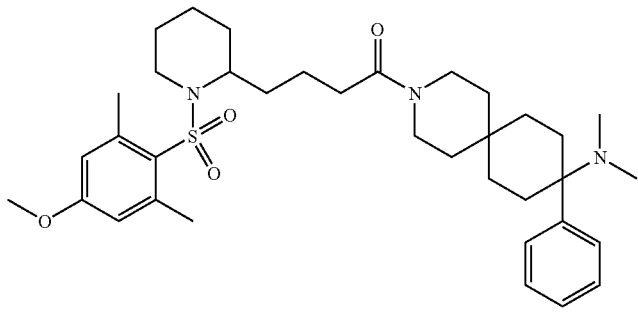 |
| 9 | 1-(9-(Dimethylamino)-9-phenyl-3-azaspiro[5.5]undecan-3-yl)-2-(1-(3-(trifluoromethyl)phenylsulfonyl)piperidin-2-yl)ethan-1-one | 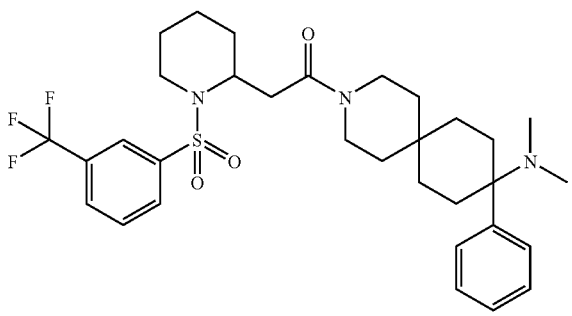 |
| 10 | (3R)-3-(2-(9-(Dimethylamino)-9-phenyl-3-azaspiro[5.5]undecan-3-yl)-2-oxoethyl)-4-(4-methoxy-2,6-dimethylphenylsulfonyl)-3,4-dihydropyrazin-2(1H)-one | 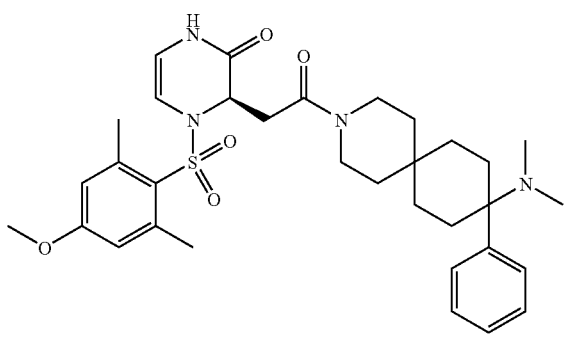 |
| 11 | 1-(9-(Dimethylamino)-9-(3-fluorophenyl)-3-azaspiro[5.5]undecan-3-yl)-2-(((S)-1-(4-methoxy-2,6-dimethylphenylsulfonyl)piperidin-2-yl)methoxy)ethanone | 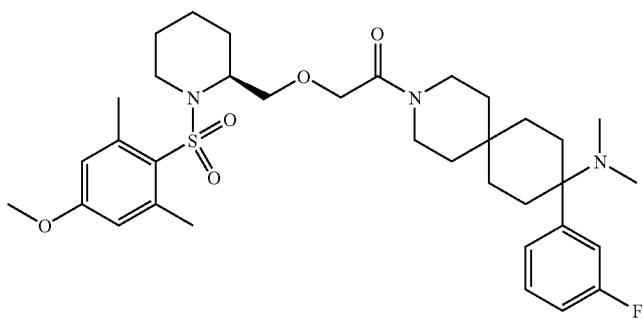 |
| 12 | 1-(9-(Azetidin-1-yl)-9-phenyl-3-azaspiro[5.5]undecan-3-yl)-2-(((S)-1-(4-methoxy-2,6-dimethylphenylsulfonyl)piperidin-2-yl)methoxy)ethanone | 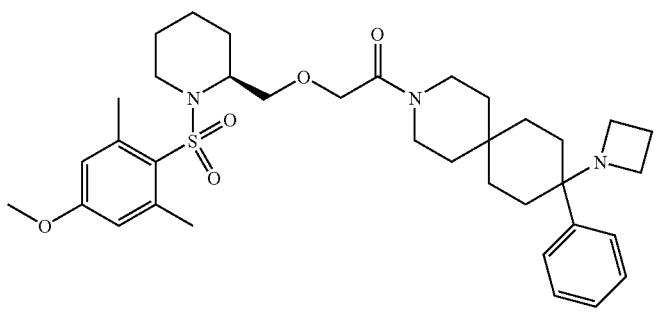 |

| | | |
|---|---|---|
| 13 | 1-(9-(3,3-Difluoroazetidin-1-yl)-9-phenyl-3-azaspiro[5.5]undecan-3-yl)-2-(((S)-1-(4-methoxy-2,6-dimethylphenylsulfonyl)piperidin-2-yl)methoxy)ethanone | 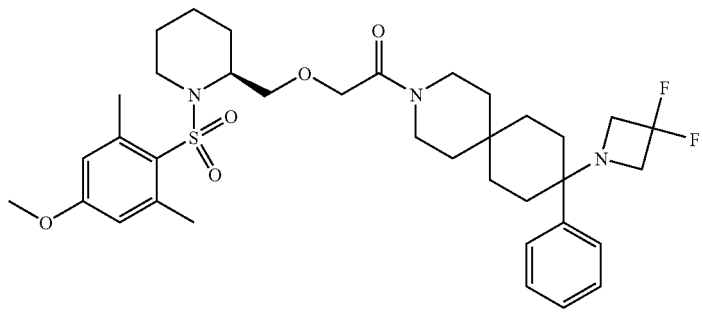 |
| CC-01 | 1-[3-(3-Fluorophenyl)-3-pyrrolidin-1-yl-9-azaspiro[5.5]undecan-9-yl]-2-[1-[[3-(trifluoromethyl)phenyl]sulfonyl]-piperidin-2-yl]-ethanone | 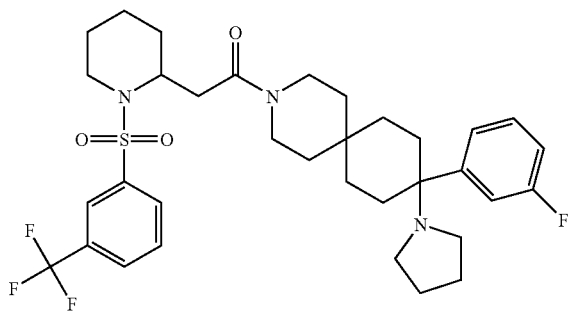 |
| CC-02 | 1-[3-(3-Fluorophenyl)-3-pyrrolidin-1-yl-9-azaspiro[5.5]undecan-9-yl]-4-[1-[(4-methoxy-2,6-dimethyl-phenyl)sulfonyl]-pipereridin-2-yl]-butan-1-one | 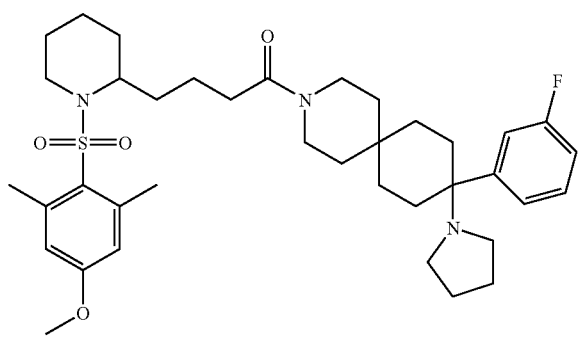 |
| CC-03 | 1-[3-(3-Fluorophenyl)-3-pyrrolidin-1-yl-9-azaspiro[5.5]undecan-9-yl]-2-[[1-[(4-methoxy-2,6-dimethyl-phenyl)sulfonyl]-piperidin-2-yl]-methoxy]-ethanone | 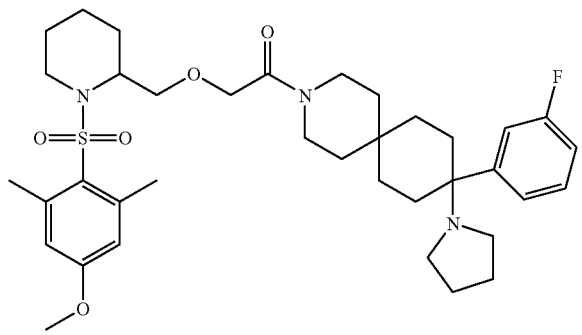 |
| CC-04 | N-Cyclopropyl-N-[2-[2-[3-(3-fluorophenyl)-3-pyrrolidin-1-yl-9-azaspiro[5.5]undecan-9-yl]-2-oxo-ethoxy]-ethyl]-4-methoxy-2,6-dimethyl-benzenesulfonic acid amide | 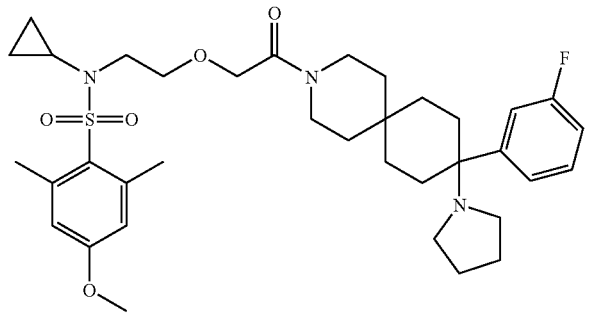 |

| | | |
|---|---|---|
| CC-05 | 2-[[1-[(2-Chloro-6-methyl-phenyl)sulfonyl]-piperidin-2-yl]-methoxy]-1-[3-(3-fluorophenyl)-3-pyrrolidin-1-yl-9-azaspiro[5.5]undecan-9-yl]-ethanone | 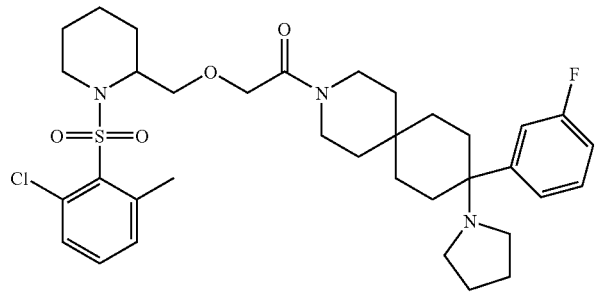 |
| CC-06 | 2-Chloro-N-cyclopropyl-N-[2-[2-[3-(3-fluorophenyl)-3-pyrrolidin-1-yl-9-azaspiro[5.5]undecan-9-yl]-2-oxo-ethoxy]-ethyl]-6-methyl-benzenesulfonic acid amide | 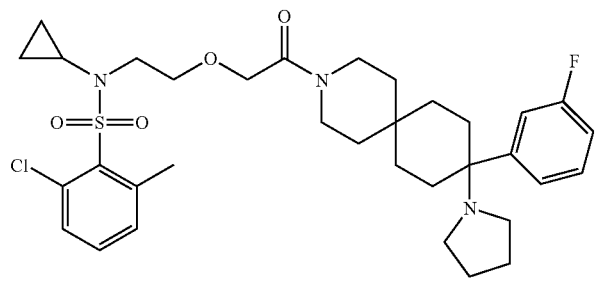 |
| CC-07 | 3-[1-[(4-Chloro-2,5-dimethyl-phenyl)sulfonyl]-piperidin-2-yl]-1-[3-(3-fluorophenyl)-3-pyrrolidin-1-yl-9-azaspiro[5.5]undecan-9-yl]-propan-1-one | 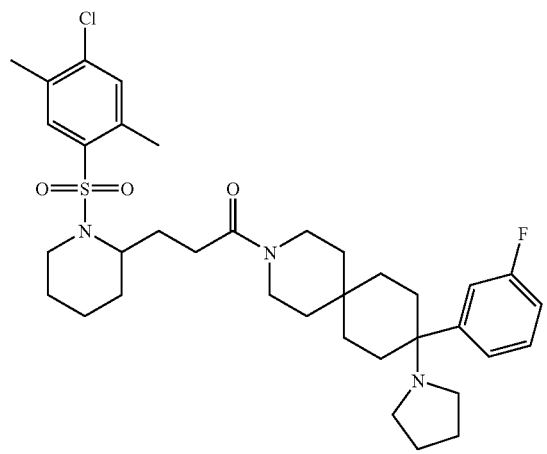 |
| CC-08 | N-[3-[3-(3-Fluorophenyl)-3-pyrrolidin-1-yl-9-azaspiro[5.5]undecan-9-yl]-3-oxo-1-phenyl-propyl]-naphthalene-2-sulfonic acid amide | 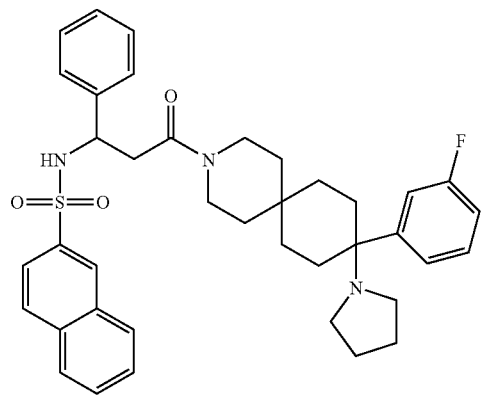 |

| | | |
|---|---|---|
| CC-09 | 2-Chloro-N-cyclopropyl-N-[2-[2-(3-dimethylamino-3-thiophen-2-yl-9-azaspiro[5.5]undecan-9-yl)-2-oxo-ethoxy]-ethyl]-6-methyl-benzenesulfonic acid amide | 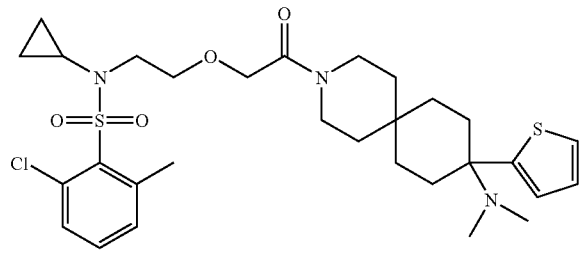 |
| CC-10 | 1-(3-Dimethylamino-3-thiophen-2-yl-9-azaspiro[5.5]undecan-9-yl)-2-[1-[[3-(trifluoromethyl)phenyl]sulfonyl]-piperidin-2-yl]-ethanone | 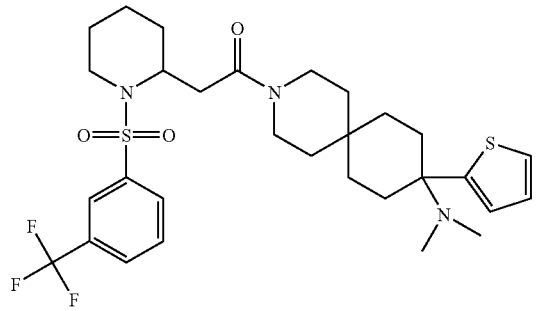 |
| CC-11 | 1-(3-Dimethylamino-3-thiophen-2-yl-9-azaspiro[5.5]undecan-9-yl)-2-[[1-[(4-methoxy-2,6-dimethyl-phenyl)sulfonyl]-piperidin-2-yl]-methoxy]-ethanone | 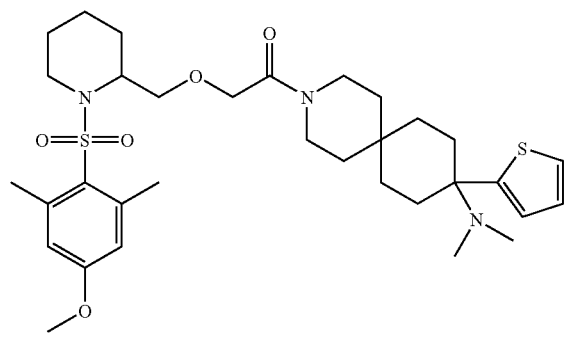 |
| CC-12 | N-Cyclopropyl-N-[2-[2-(3-dimethylamino-3-thiophen-2-yl-9-azaspiro[5.5]undecan-9-yl)-2-oxo-ethoxy]-ethyl]-4-methoxy-2,6-dimethyl-benzenesulfonic acid amide | 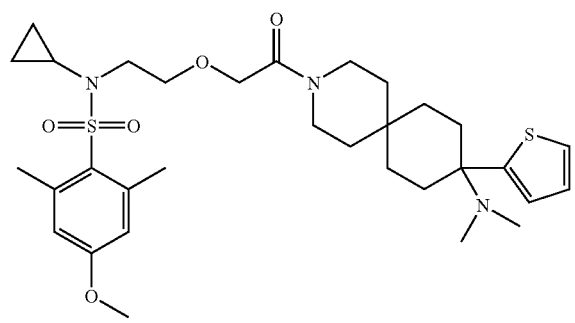 |
| CC-13 | 2-[[1-[(2-Chloro-6-methyl-phenyl)sulfonyl]-piperidin-2-yl]-methoxy]-1-(3-dimethylamino-3-thiophen-2-yl-9-azaspiro[5.5]undecan-9-yl)-ethanone | 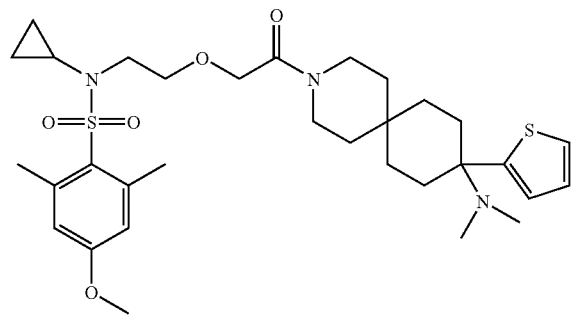 |

| | | |
|---|---|---|
| CC-14 | 3-[1-[(4-Chloro-2,5-dimethyl-phenyl)sulfonyl]-piperidin-2-yl]-1-(3-dimethylamino-3-thiophen-2-yl-9-azaspiro[5.5]undecan-9-yl)-propan-1-one | 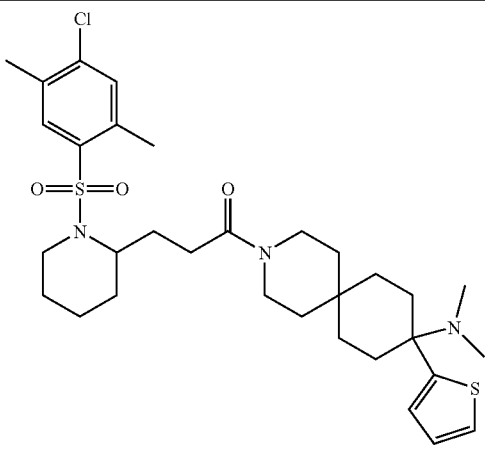 |
| CC-15 | N-[3-(3-Dimethylamino-3-thiophen-2-yl-9-azaspiro[5.5]undecan-9-yl)-3-oxo-1-phenyl-propyl]-naphthalene-2-sulfonic acid amide | 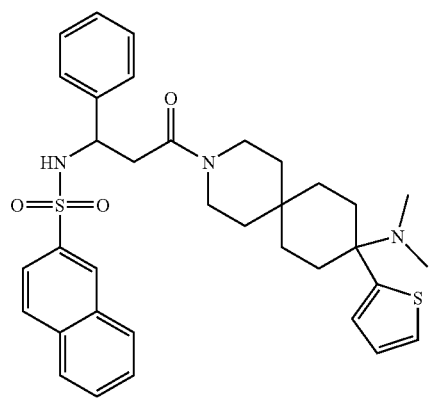 |
| CC-16 | 1-(3-Dimethylamino-3-thiophen-2-yl-9-azaspiro[5.5]undecan-9-yl)-4-[1-[(4-methoxy-2,6-dimethyl-phenyl)sulfonyl]-piperidin-2-yl]-butan-1-one | 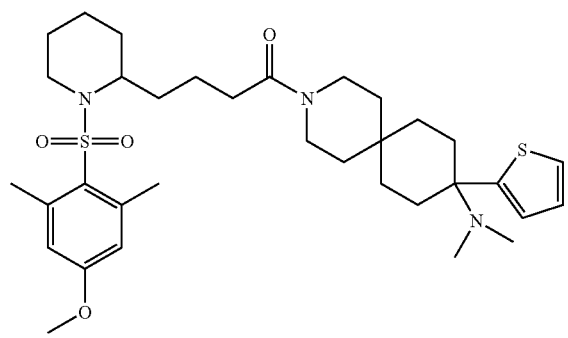 | optionally in the form of an isolated enantiomer or an isolated diastereomer, the racemate, the enantiomers, the diastereomers, mixtures of enantiomers and/or diastereomers, and each in the form of their bases and/or physiologically compatible salts.

The numbering of the individual embodiments of the compounds according to the invention used above is retained in the following explanations of the present invention, particularly in the description of the examples.

According to one aspect of the present invention the compounds according to the invention have an antagonistic action on the human B1R receptor or the B1R receptor of the rat. In a preferred embodiment of the invention the compounds according to the invention have an antagonistic action on both the human B1R receptor (hB1R) and on the B1R receptor of the rat (rB1R).

In a preferred embodiment of the present invention the compounds according to the invention exhibit at least 15%, 25%, 50%, 70%, 80% or 90% inhibition on the human B1R receptor and/or on the B1R receptor of the rat in the FLIPR assay at a concentration of 10 μM. Most particularly preferred are compounds which at a concentration of 10 μM exhibit at least 70%, in particular at least 80% and particularly preferably at least 90% inhibition on both the human and rat B1R receptors.

The agonistic or antagonistic action of substances can be quantified on the bradykinin receptor 1 (B1R) of the human and rat species with ectopically expressing cell lines (CHO K1 cells) and with the aid of a $Ca^{2+}$-sensitive dye (Fluo-4) using a fluorescent imaging plate reader (FLIPR). The indication in % activation is based on the $Ca^{2+}$ signal after addition of Lys-Des-Arg$^9$ bradykinin (0.5 nM) or Des-Arg$^9$ bradykinin (100 nM). Antagonists lead to a suppression of the $Ca^{2+}$ influx following administration of the agonist. The % inhibition in comparison with the maximum achievable inhibition is indicated.

The substances according to the invention preferably act for example on the B1R of relevance in connection with various diseases, such that they are suitable as a pharmaceutical active ingredient in medicaments. The invention therefore also provides medicaments containing at least one spiroamine according to the invention, optionally along with suitable additives and/or auxiliary substances and/or optionally further active ingredients.

The pharmaceutical compositions according to the invention are suitable for combating pain, in particular pain selected from the group consisting of acute pain, neuropathic pain, visceral pain, chronic pain and inflammatory pain; or for the treatment of migraine; diabetes; diseases of the respiratory tract; inflammatory bowel diseases; neurological diseases; septic shock; reperfusion syndrome; obesity, and as an angiogenesis inhibitor.

In addition to at least one substituted spiroamine according to the invention, the pharmaceutical compositions according to the invention optionally contain suitable additives and/or auxiliary substances, including carrier materials, fillers, solvents, diluents, dyes and/or binders, and can be administered as liquid dosage forms in the form of injection solutions, drops or juices, as semi-solid dosage forms in the form of granules, tablets, pellets, patches, capsules, plasters/spray plasters or aerosols. The choice of auxiliary substances, etc., and the amount thereof to use depend on whether the medicament is to be administered by oral, peroral, parenteral, intravenous, intraperitoneal, intradermal, intramuscular, nasal, buccal, rectal or topical means, for example on the skin, mucous membranes or in the eyes. Preparations in the form of tablets, pastilles, capsules, granules, drops, juices and syrups are suitable for oral administration; solutions, suspensions, easily reconstitutable dry preparations and sprays are suitable for parenteral, topical and inhalative administration. Substituted spiroamines according to the invention in a depot formulation, in dissolved form or in a plaster, optionally with addition of agents promoting skin penetration, are suitable preparations for percutaneous administration. Preparation forms suitable for oral or percutaneous administration can deliver the substituted spiroamines according to the invention on a delayed release basis. The substituted spiroamines according to the invention can also be used in parenteral long-term depot forms, such as implants or implanted pumps, for example. Other additional active ingredients known to the person skilled in the art can be added in principle to the pharmaceutical compositions according to the invention.

The amount of active ingredient to be administered to the patient varies depending on the weight of the patient, the manner of administration, the indication and the severity of the illness. From 0.00005 to 50 mg/kg, preferably 0.01 to 5 mg/kg, of at least one substituted spiroamine according to the invention is conventionally administered. A preferred form of the pharmaceutical composition according to the invention contains a substituted spiroamine according to the invention as an isolated diastereomer and/or enantiomer, as a racemate or as a non-equimolar or equimolar mixture of diastereomers and/or enantiomers.

B1R is involved in particular in the pain mechanism. Accordingly, the substituted spiroamines of the invention can be used for the treatment of pain, in particular acute, visceral, neuropathic or chronic pain.

The invention therefore also provides for the use of a substituted spiroamine according to the invention to prepare a medicament for the treatment of pain, in particular acute, visceral, neuropathic or chronic pain. A particular embodiment of the present invention is the use of at least one of the substituted spiroamines according to the invention to prepare a medicament for the treatment of inflammatory pain.

The invention also provides the use of a substituted spiroamine according to the invention to prepare a medicament for the treatment of diabetes, diseases of the respiratory tract, for example bronchial asthma, allergies, COPD/chronic obstructive pulmonary disease or cystic fibrosis; inflammatory bowel diseases, for example ulcerative colitis or CD/Crohn's disease; neurological diseases, for example multiple sclerosis or neurodegeneration; inflammations of the skin, for example atopic dermatitis, psoriasis or bacterial infections; rheumatic diseases, for example rheumatoid arthritis or osteoarthritis; septic shock; reperfusion syndrome, for example following heart attack or stroke; obesity; and as an angiogenesis inhibitor.

In either or both of the above uses it may be advantageous to use a substituted spiroamine in the form of a pure diastereomer and/or enantiomer, a racemate or a non-equimolar or equimolar mixture of diastereomers and/or enantiomers.

The invention also provides a process for the treatment, in particular of one of the aforementioned indications in a human or in a non-human mammal requiring treatment, by administration of a therapeutically effective dose of a substituted spiroamine according to the invention or of a medicament according to the invention.

The present invention also provides a process for preparing the substituted spiroamines according to the invention, in particular as described in the following description and examples. The process according to the invention is represented in the following scheme 1:

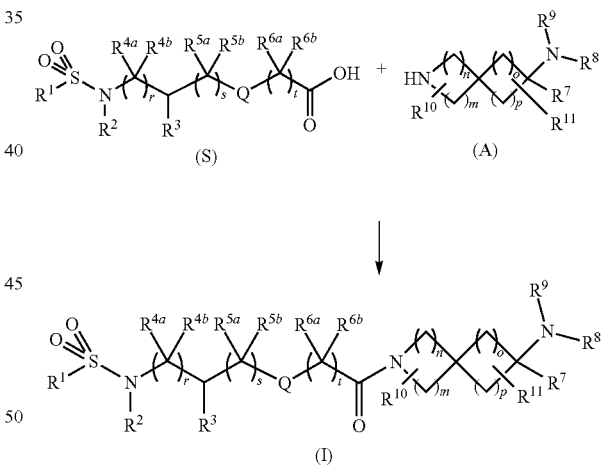

The amines (A) are preferably reacted in an amide formation using acids (S) in the presence of dehydrating agents such as sodium or magnesium sulfate, phosphorus oxide or reagents such as, for example, CDI, DCC (optionally polymer-bound), TBTU, HATU, EDCl, PyBOP or PFPTFA, also in the presence of HOAt or HOBt and an organic base, for example DIPEA, triethylamine or pyridine, in an organic solvent such as THF, dichloromethane, diethyl ether, dioxane, DMF or acetonitrile, to form the compounds of to the invention corresponding to formula (I). The amide formation can also take place, however, by converting the relevant acid (S) into the corresponding acid chloride or acid anhydride and then reacting it with the relevant amine (A). The acid chloride can be prepared by reaction with $SOCl_2$, $PCl_3$, $PCl_5$ or 1-chloro-N,N,2-trimethyl-1-propenylamine, optionally in a solvent such as THF, dichloromethane, diethyl ether, dioxane, DMF or acetonitrile, at a temperature of between −78° C. and 100° C.

General Synthesis Methods:

The following abbreviations are used below:
9-BBN=9-borabicyclo[3,3,1]nonane
BOP=1-benzotriazolyloxy-tris-(dimethylamino)-phosphonium hexafluorophosphate
CDI=1,1'-carbonyldiimidazole
d=days
dba=dibenzylidene acetone
DBU=1,8-diazabicyclo(5.4.0)undec-7-ene
DCC=dicyclohexylcarbodiimide
DCM=dichloromethane
DIPEA=N,N—N,N-diisopropylethylamine
DMAP=4-dimethylaminopyridine
DMF=N,N-dimethyl formamide
DMS=dimethylsulfide
EDCI=N-(3-dimethylaminopropyl)-N'-ethylcarbodiimide hydrochloride
eq=equivalents
Et=ethyl
h=hours
HATU=N-[(dimethylamino)-1H-1,2,3-triazolo[4,5-b]pyridino-1-ylmethylenemethane aminium hexafluorophosphate N-oxide
HBTU=O-(benzotriazol-1-yl)-N,N,N',N'-tetramethyluronium hexafluorophosphate
HOAt=1-hydroxy-7-azabenzotriazole
HOBt=1-hydroxybenzotriazole
LHMDS=lithium hexamethyl disilazide
MEK=methyl ethyl ketone
min=minutes
Ms=mesyl
NMP=N-methylpyrrolidone
Oxone®=2 $KHSO_5 \cdot KHSO_4 \cdot K_2SO_4$
PFPTFA=pentafluorophenyl trifluoroacetate
PFP=pentafluorophenol
PTSA=p-toluenesulfonic acid
PyBOP=benzotriazol-1-yl-oxy-tris-pyrrolidino-phosphonium hexafluorophosphate
TBTU=O-(benzotriazol-1-yl)-N,N,N',N'-tetramethyluronium tetrafluoroborate
TFA=trifluoroacetic acid
THF=tetrahydrofuran, and
TMSCl=trimethylsilylchloride.

It will be apparent to persons skilled in the art that the sequence of some reaction steps can optionally be varied.

Suitable protective groups can be introduced and removed using methods known to those skilled in the art from the literature, as described, for example, in (a) Philip J. Kocienski, Protecting Groups, 3rd Edition, Georg Thieme Verlag, 2005 (ISBN 3-13-135603-0) and (b) Peter G. M. Wuts, Theodora W. Greene, Greene's Protective Groups in Organic Synthesis, 4th Edition, Wiley-Interscience, 2007 (ISBN-13: 978-0-471-69754-1).

The separation of diastereomers and/or enantiomers is performed by methods known to persons skilled in the art, for example by recrystallisation, chromatography or in particular HPLC chromatography or crystallisation with an optionally chiral acid or base and separation of the salts, or chiral HPLC chromatography (Fogassy et al., Optical resolution methods, Org. Biomol. Chem. 2006, 4, 3011-3030).

The acid structural units used, compounds having the general formula (S), which are divided into acyclic acid structural units D and cyclic acid structural units J, are known from β-amino acids, for example, from the literature—Tetrahedron Report Number 617: M. Liu, M. P. Sibi, *Tetrahedron*, 58, (2002), 7991-8053, or can be prepared as described below.

General Synthesis Method for the Preparation of Acyclic Acid Structural Units D

Scheme 2

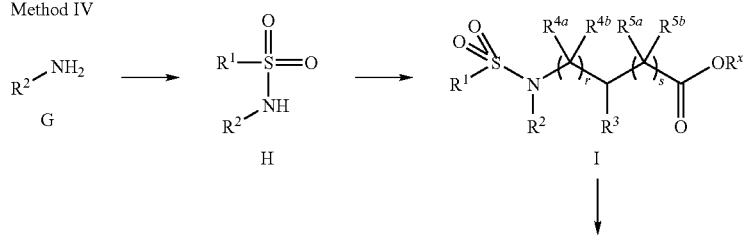

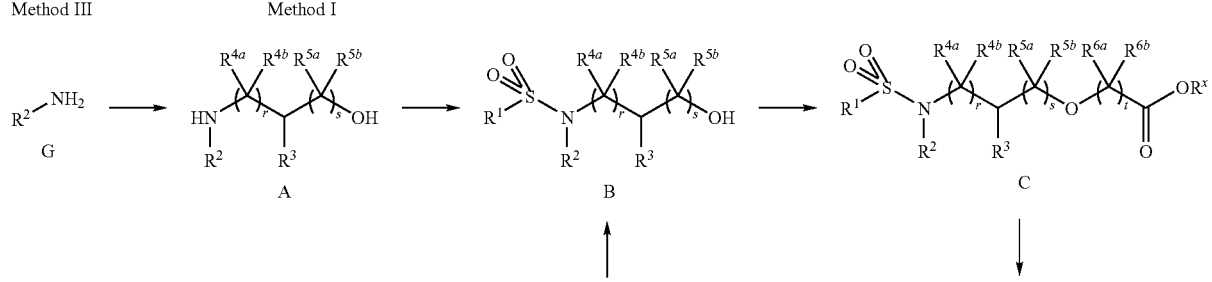

Method II

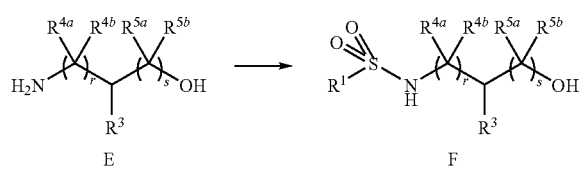 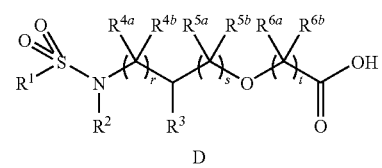

$R^x$ = preferably methyl, ethyl or tert-butyl

In Method I the racemic (R- and S-configuration) or enantiopure (R- or S-configuration) amino alcohols A are converted into the sulfonylated amino alcohols B in a sulfonylation with sulfonyl chlorides, bromides or pentafluorophenolate $R^1SO_2X$ (X=Cl, Br, OPFP) optionally in the presence of an organic or inorganic base, for example potassium carbonate, sodium carbonate, sodium hydrogen carbonate, diisopropylethylamine, triethylamine, pyridine, dimethylaminopyridine, diethylamine or DBU, preferably in an organic solvent, for example, tetrahydrofuran, dichloromethane, acetonitrile or acetone, and at a temperature of preferably 0° C. to reflux temperature.

In Method II the racemic (R- and S-configuration) or enantiopure (R- or S-configuration) amino alcohols E are converted into the sulfonylated amino alcohols F in a sulfonylation with sulfonyl chlorides, bromides or pentafluorophenolate $R^1SO_2X$ (X=Cl, Br, OPFP) optionally in the presence of an organic or inorganic base, for example potassium carbonate, sodium hydrogen carbonate, diisopropylethylamine, triethylamine, pyridine, dimethylaminopyridine, diethylamine or DBU, preferably in an organic solvent, for example acetone, acetonitrile, dichloromethane or tetrahydrofuran, and at a temperature of preferably 0° C. to reflux temperature. The sulfonylated amino alcohols F are then converted into the sulfonylated amino alcohols B in an alkylation reaction with alkyl halides (RX, X=I, Br, Cl), mesylates or alternative alkylation reagents, optionally in the presence of an organic or inorganic base, for example sodium hydride, potassium carbonate, caesium carbonate, DBU or DIPEA, preferably in an organic solvent, for example dimethyl formamide, acetone, THF, acetonitrile, dioxane or these solvents as blends, at a temperature of preferably 0° C. to reflux temperature.

In Method III commercial amines G or amines G available to the person skilled in the art are converted into amino alcohols A in an alkylation reaction with hydroxy alkyl halides in organic solvents such as ethanol, methanol, diethyl ether, THF or dichloromethane, at a temperature of preferably 0° C. to reflux temperature, for up to 20 hours. The conversion of the amino alcohols A into sulfonylated amino alcohols B proceeds in an analogous manner to Method I.

In Method IV amines G are converted into the sulfonylated derivatives H in a sulfonylation with sulfonyl chlorides, bromides or pentafluorophenolate $R^1SO_2X$ (X=Cl, Br, OPFP) optionally in the presence of an organic or inorganic base, for example potassium carbonate, sodium carbonate, sodium hydrogen carbonate, diisopropylethylamine, triethylamine, pyridine, dimethylaminopyridine, diethylamine or DBU, preferably in an organic solvent, for example dichloromethane, tetrahydrofuran, acetone or acetonitrile, and at a temperature of preferably 0° C. to reflux temperature. The sulfonylated amines H are then converted into the sulfonylated amino esters I in an alkylation reaction with halogenated alkyl esters, optionally in the presence of an organic or inorganic base, for example sodium hydride, potassium carbonate, caesium carbonate, DBU or DIPEA, preferably in an organic solvent, for example dimethyl formamide, acetone, THF, acetonitrile, dioxane or these solvents as blends. The sulfonylated amino esters I are converted into sulfonylated amino alcohols B in a reduction reaction, using as reducing agents metal hydrides such as, for example, $LiAlH_4$, $BH_3 \times DMS$ or $NaBH_4$, in an organic solvent such as THF or diethyl ether.

In Methods I-IV the sulfonylated amino alcohols B are converted into products having the general structure C in an alkylation reaction with halogenated ester derivatives using tetrabutylammonium chloride or bromide or tetrabutylammonium hydrogen sulfate, in a phase transfer reaction using an organic solvent such as THF, toluene, benzene or xylene and an inorganic base such as potassium hydroxide, sodium hydroxide, sodium carbonate, sodium hydrogen carbonate, potassium carbonate or in the presence of an organic or inorganic base, conventional inorganic bases being metal alcoholates such as sodium methanolate, sodium ethanolate, potassium tert-butylate, lithium or sodium bases such as lithium diisopropylamide, butyl lithium, tert-butyl lithium, sodium methylate or metal hydrides such as potassium hydride, lithium hydride, sodium hydride, conventional organic bases being diisopropylethylamine, triethylamine, in an organic solvent such as dichloromethane, THF or diethyl ether, preferably at 0° C. to reflux temperature. The ester derivatives C are converted into the acid stages having the general formula D in an ester cleavage using organic acids such as trifluoroacetic acid or aqueous inorganic acids such as hydrochloric acid or using aqueous inorganic bases such as lithium hydroxide, potassium hydroxide, sodium hydroxide, sodium carbonate, sodium hydrogen carbonate, potassium carbonate, in organic solvents such as methanol, dioxane, dichloromethane, THF, diethyl ether or these solvents as blends, preferably at 0° C. to room temperature.

General Synthesis Method for the Preparation of Cyclic Acid Structural Units J

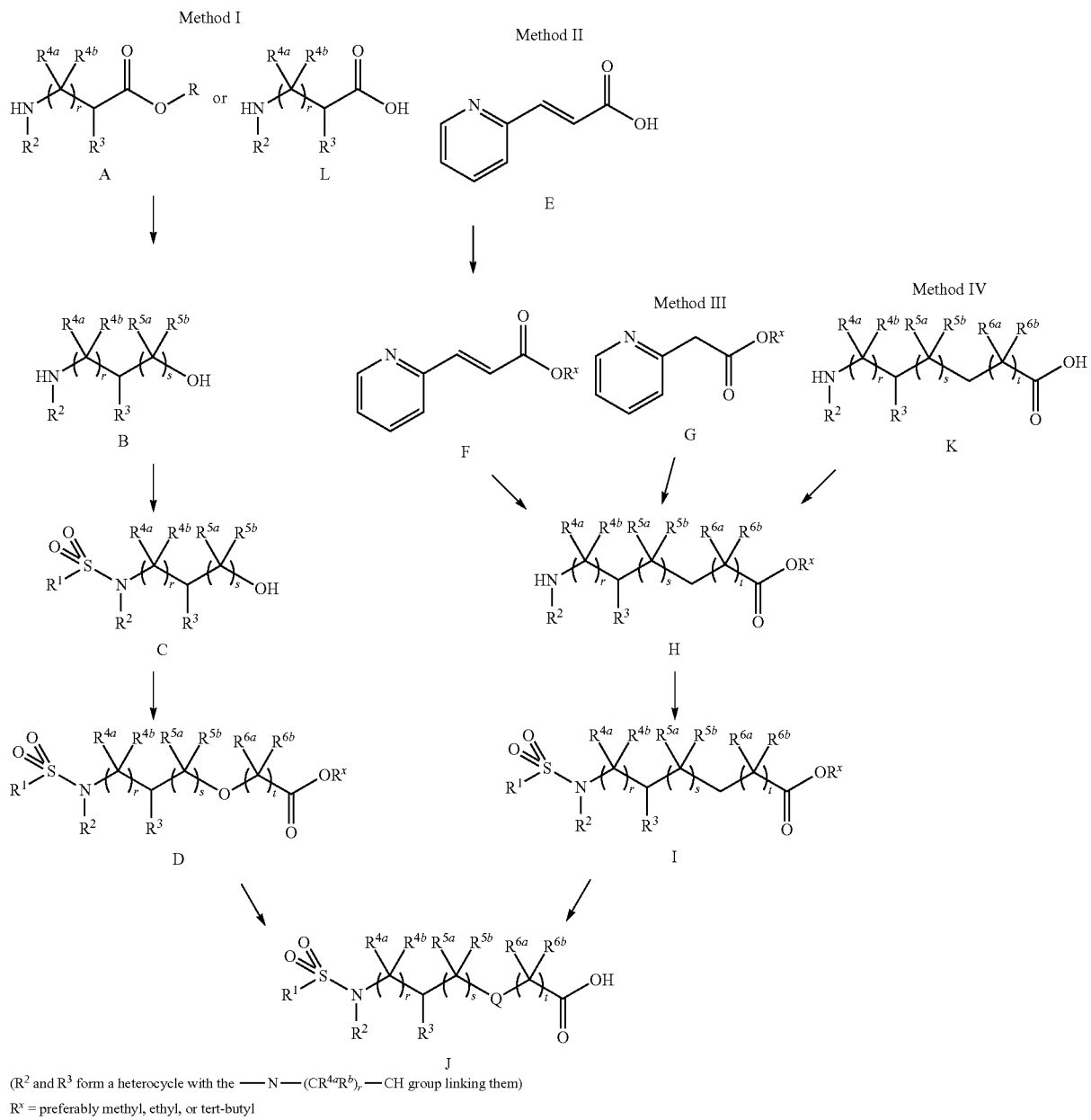

Scheme 3

($R^2$ and $R^3$ form a heterocycle with the —N—$(CR^{4a}R^b)_r$—CH group linking them)
$R^x$ = preferably methyl, ethyl, or tert-butyl In Method I the racemic (R- and S-configuration) or enantiopure (R- or S-configuration) amino acid esters A or amino acids L are converted into an amino alcohol B by means of a reduction, using as reducing agents metal hydrides such as, for example, $LiAlH_4$, $BF_3$ etherate, $BH_3 \times DMS$ or $NaBH_4$, in an organic solvent such as THF or diethyl ether, at temperatures of preferably 0° C. to reflux temperature. The amino alcohols B are further converted into the sulfonylated amino alcohols C in a sulfonylation with sulfonyl chlorides, bromides or pentafluorophenolate $R^1SO_2X$ (X=Cl, Br, OPFP) optionally in the presence of an organic or inorganic base, for example potassium carbonate, sodium hydrogen carbonate, diisopropylethylamine, triethylamine, pyridine, dimethylaminopyridine, diethylamine or DBU, preferably in an organic solvent, for example acetone, acetonitrile, dichloromethane or tetrahydrofuran, and at a temperature of preferably 0° C. to reflux temperature. The sulfonylated amino alcohols C are converted into products having the general structure D in an alkylation reaction with halogenated ester derivatives using tetrabutylammonium chloride or bromide or tetrabutylammonium hydrogen sulfate, in a phase transfer reaction using an organic solvent such as THF, toluene, benzene or xylene and an inorganic base such as potassium hydroxide, sodium hydroxide, sodium carbonate, sodium hydrogen carbonate, potassium carbonate or in the presence of an organic or inorganic base, conventional inorganic bases being metal alcoholates such as sodium methanolate, sodium ethanolate, potassium tert-butylate, lithium or sodium bases such as lithium diisopropylamide, butyl lithium, tert-butyl lithium, sodium methylate or metal hydrides such as potassium hydride, lithium hydride, sodium hydride, conventional organic bases being diisopropylethylamine, triethylamine, in an organic solvent such as dichloromethane, THF or diethyl ether, at 0° C. to reflux temperature.

In Method II 3-(pyridin-2-yl)acrylic acid E is esterified to stage F using dehydrating reagents, for example inorganic acids such as $H_2SO_4$ or phosphorus oxides, or organic reagents such as thionyl chloride, in organic solvents such as THF, diethyl ether, methanol, ethanol or dichloromethane, at temperatures of preferably room temperature to reflux temperature.

In Methods II and III the ester stages F and G are hydrogenated to the intermediates H in a hydrogenation under conditions known to the person skilled in the art, in organic solvents such THF, chloroform and in the presence of catalysts such as platinum oxides, with hydrogen under normal pressure or excess pressure.

In Method IV the racemic (R- and S-configuration) or enantiopure (R- or S-configuration) amino acids K are esterified to the amino esters H using dehydrating reagents, for example inorganic acids such as $H_2SO_4$ or phosphorus oxides or organic reagents such as thionyl chloride, in organic solvents such as THF, diethyl ether, methanol, ethanol or dichloromethane.

In Methods II to IV the amino esters H are converted further into the sulfonylated amino esters I in a sulfonylation with sulfonyl chlorides, bromides or pentafluorophenolate $R^1SO_2X$ (X=Cl, Br, OPFP) optionally in the presence of an organic or inorganic base, for example potassium carbonate, sodium hydrogen carbonate, diisopropylethylamine, triethylamine, pyridine, diethylamine or DBU, preferably in an organic solvent, for example acetonitrile, dichloromethane or tetrahydrofuran, and at a temperature of preferably 0° C. to reflux temperature.

In Methods I to IV the ester derivatives D and I are converted into the acid stages having the general formula J in an ester cleavage using organic acids such as trifluoroacetic acid or aqueous inorganic acids such as hydrochloric acid or using aqueous inorganic bases such as lithium hydroxide, potassium hydroxide, sodium hydroxide, sodium carbonate, sodium hydrogen carbonate, potassium carbonate, in organic solvents such as methanol, dioxane, dichloromethane, THF, diethyl ether or these solvents as blends, at 0° C. to room temperature.

The amine structural units used, compounds having the general formula (A), can be prepared as described below.

General Method for the Synthesis of Amine Structural Units (A)

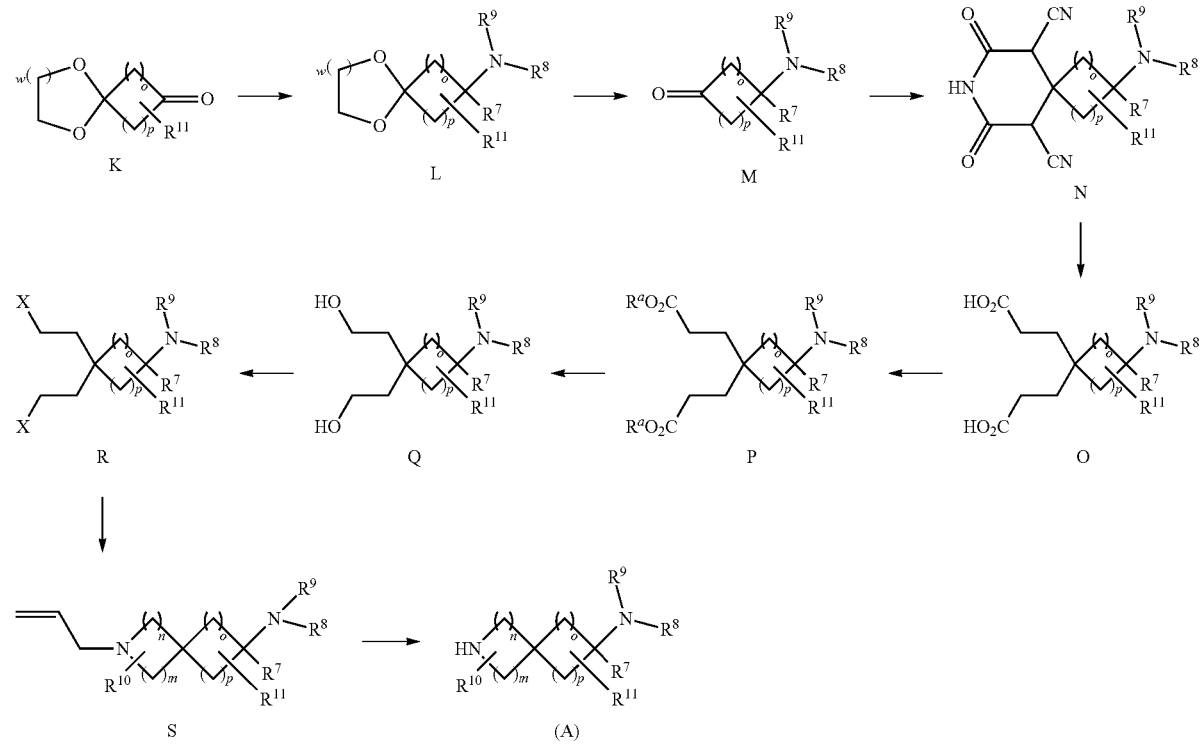

Scheme 4

Method 1

$w = 1, 2$
$R^a$ = methyl, ethyl
X = halogen (Cl, Br, I), OMs or another suitable leaving group
$n = m = 2$
$p = 2$
$o = 1, 2$
$R^{10}$ = H Compounds having the general formula K are converted by means of Method A or Method B into compounds having the general formula L.

Method A

Compounds having the general formula K are converted into benzotriazole aminal in an aminal formation reaction by reaction with an amine and 1H-benzotriazole, the person skilled in the art being aware that the benzotriazole aminal can be present both in equilibrium and in the 1H and 2H form. Benzene, toluene, ethanol, diethyl ether or THF, for example, are suitable as solvents. The use of a Dean-Stark water separator, molecular sieve or other dehydrating agent may be necessary. The reaction time at a reaction temperature from +20° C. to +110° C. can be between 1 and 20 h. The benzotriazole aminal obtained as intermediate is then converted into compounds having the general formula L with metal organyls such as magnesium, zinc or lithium organyls in organic solvents, for example diethyl ether, dioxane or THF.

Method B

Compounds having the general formula K are converted into nitrilamines by adding an amine and a cyanide source. This reaction can take place in one or two stages. In the two-stage variant a nitrile alcohol is first formed and isolated. Formation of the nitrile alcohol can take place by reacting compounds having the general formula K with HCN, KCN or NaCN as the cyanide source, wherein if NaCN and KCN are used, the necessary cyanide is released by the addition of sodium hydrogen sulfite, sulfuric acid, acetic acid or hydrochloric acid, for example. Preferred solvents are water, methanol, ethanol, THF, piperidine, diethyl ether or a blend of these solvents. Trimethyl silyl cyanide, for example, is likewise suitable as the cyanide source; the cyanide can be released by means of boron trifluoride etherate, $InF_3$ or HCl, for example. Preferred solvents are water or toluene. Another suitable cyanide source is (cyano-C)diethyl aluminium, for example. THF, toluene or a blend of the two solvents can be used as solvent. The reaction temperature for all variants is preferably between −78° C. and +25° C. For the reaction of the nitrile alcohol with the amine to form nitrilamines, alcohols such as methanol or ethanol are particularly suitable as solvent. The reaction temperature can be between 0° C. and +25° C. In the single-stage variant the primarily formed nitrile alcohol is formed in situ and reacted with the amine to form nitrilamines. The nitrilamine obtained as intermediate is then reacted with metal organyls such as magnesium, zinc or lithium organyls in organic solvents, for example diethyl ether, dioxane or THF, to form substituted spiroamines having the general formula L.

Compounds having the general formula M are obtained by eliminating a suitable ketone protective group from compounds having the general formula L using methods known to the person skilled in the art.

The preferred O-acetal protective group can be eliminated as follows. The ketone is obtained in an acetal cleavage reaction under acid conditions. Suitable acids are both inorganic Brønsted or Lewis acids, such as hydrochloric acid, sulfuric acid, ammonium chloride or hydrogen sulfate or $AlI_3$, and organic acids, such as e.g. p-toluenesulfonic acid, acetic acid, oxalic acid, trifluoromethanesulfonic acid, formic acid, trifluoroacetic acid or citric acid. The reaction can be carried out various solvents, such as toluene, THF, chloroform, DCM, xylene, acetonitrile, water, dioxane, acetone, diethyl ether or ethyl acetate, at temperatures from −10° C. to room temperature.

Compounds having the general formula M are reacted with ethyl cyanoacetate in the presence of ammonia in a suitable solvent, for example methanol or ethanol, at temperatures of preferably −50° C. to 100° C. to obtain compounds of formula N.

Compounds having the general formula N are reacted in the presence of a suitable acid, for example sulfuric acid or HCl, in a suitable solvent, preferably water, at temperatures of preferably −20° C. to 200° C., to form compounds of formula O.

Compounds having the general formula O are reacted in at least one solvent, preferably selected from the group consisting of methanol, ethanol, propanol, isopropanol, dioxane, diethyl ether, tetrahydrofuran, dichloromethane, dimethyl formamide and dimethyl sulfoxide, with an alcohol, using at least one acid chloride or acid anhydride or acid, preferably from the group consisting of thionyl chloride, acetyl chloride, acetic anhydride, sulfuric acid and hydrochloric acid, at temperatures of preferably 0° C. to 120° C., to form compounds having the general formula P.

Compounds having the general formula P can alternatively also be prepared in one stage directly from compounds having the general formula O in the presence of, for example, sulfuric acid in ethanol at a reaction temperature of 0° C. to 200° C.

Compounds having the general formula P are reacted in at least one solvent, preferably selected from the group consisting of THF, diethyl ether, toluene or DCM, with at least one reducing agent, preferably selected from the group consisting of diisobutyl aluminium hydride, lithium aluminium hydride, lithium-tri-tert-butoxyaluminium hydride, sodium-bis(2-methoxyethoxy)aluminium hydride, sodium boron hydride, aluminium hydride, $BH_3 \times DMS$, at temperatures of preferably −78° C. to 200° C., to form compounds having the general formula Q.

Compounds having the general formula Q are obtained by introducing a suitable leaving group, such as for example halogen or mesylate, from compounds having the general formula R.

Compounds having the general formula Q are reacted in at least one solvent, preferably selected from the group consisting of dichloromethane, dioxane, diethyl ether, tetrahydrofuran, acetonitrile and dimethyl formamide, with a sulfonyl chloride, preferably selected from the group consisting of tolylsulfonyl chloride, methylsulfonyl chloride, trifluoromethylsulfonyl chloride, and at least one base, preferably selected from the group consisting of caesium carbonate, calcium carbonate, potassium carbonate, triethylamine, diisopropyl ethylamine and pyridine, at temperatures of preferably 0° C. to 80° C., to form compounds of formula R (preferably X=OMs).

Compounds having the general formula R, optionally in a solvent or blend of solvents, preferably selected from the group consisting of dichloromethane, dioxane, diethyl ether, tetrahydrofuran, acetonitrile, toluene and dimethyl formamide, are reacted with a suitable amine, preferably allylamine, optionally in the presence of a suitable base, preferably selected from the group consisting of caesium carbonate, calcium carbonate, potassium carbonate, potassium hydrogen carbonate, sodium hydrogen carbonate, triethylamine, diisopropyl ethylamine and pyridine, at temperatures of preferably 0° C. to 200° C., to form compounds of formula S.

Amines of formula (A) are obtained by eliminating the amine protective group from compounds corresponding to formula S using methods known to persons skilled in the art.

Preferred protective groups, in particular allyl, can be eliminated as follows. Allyl protective groups can be eliminated in at least one solvent, preferably selected from the group consisting of toluene, acetonitrile, water and/or THF, in the presence of a suitable catalyst, for example Grubb's catalyst, Wilkinson's catalyst ([Ph$_3$P]$_3$RhCl), a suitable Pd(0) catalyst, for example Pd(dba)$_2$ or Pd[PPh$_3$]$_4$, or Pd/C, optionally in the presence of 2-mercaptobenzoic acid, N,N-dimethylbarbituric acid or methanesulfonic acid, at temperatures of preferably 0° C. to 200° C.

Compounds having the general formula (A) can alternatively also be prepared in two stages from compounds having the general formula N.

preferably −20° C. to 200° C. The intermediates are reacted in at least one solvent, preferably selected from the group consisting of THF, diethyl ether, toluene or DCM, with at least one reducing agent, preferably selected from the group consisting of diisobutyl aluminium hydride, lithium aluminium hydride, lithium-tri-tert-butoxyaluminium hydride, sodium-bis(2-methoxyethoxy)aluminium hydride, sodium boron hydride, aluminium hydride, BH$_3$×DMS, at temperatures of preferably −78° C. to 200° C., to form compounds having the general formula (A).

Scheme 6

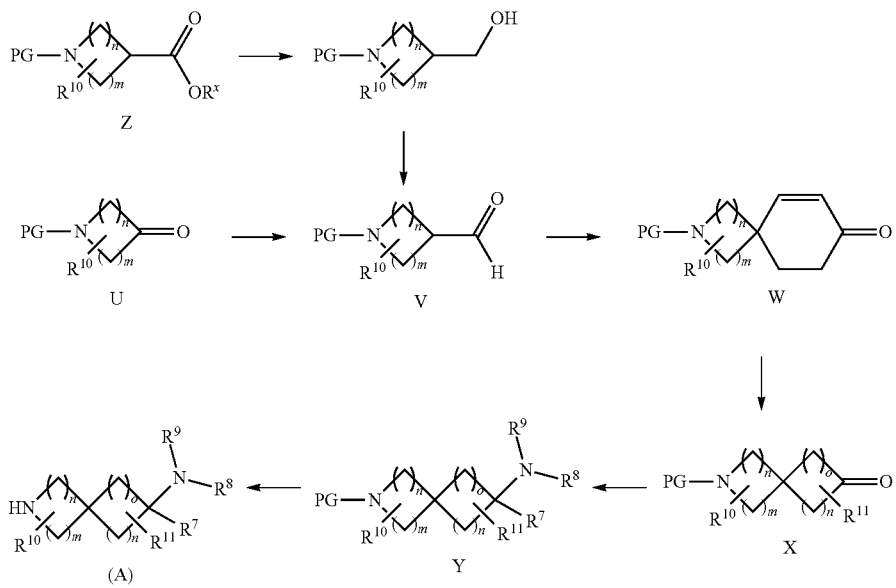

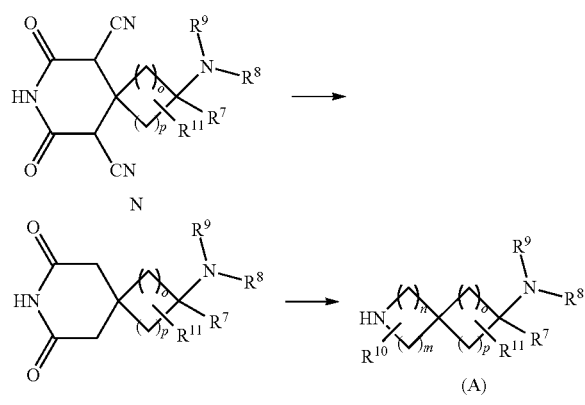

Scheme 5

Compounds having the general formula N are reacted in the presence of a suitable acid, for example sulfuric acid or HCl, in a suitable solvent, preferably water, at temperatures of Compounds having the general formula V are obtained from compounds having the general formula U in a Wittig reaction using a corresponding phosphonium compound, for example (methoxymethyl)triphenyl phosphonium chloride, and a strong base, for example potassium tert-butylate, n-butyl lithium, s-butyl lithium, phenyl lithium, lithium diisopropylamide, sodium bis(trimethylsilyl)amide or lithium hexamethyl disilazide, in organic solvents, such as THF, diethyl ether, cyclohexane, toluene or a blend of these solvents, at a temperature of between −78° C. and +30° C., after acid processing, for example under the influence of HCl in a suitable reaction medium, for example water, THF, acetone or corresponding blends, at a temperature of between −20° C. and +100° C.

Alternatively compounds having the general formula V may also be obtained in either a 1 or a 2 step process starting from compounds having the general formula Z. Conversion to the aldehyde function in 1 step to give compounds of the general formula V is carried out by reaction of the compounds having the general formula Z with a suitable reducing agent. In this context, diisobutyl aluminium hydride, lithium aluminium hydride, lithium tri-tert-butoxyaluminium hydride, sodium bis(2-methoxyethoxy)aluminium hydride or bis(cyclopentadienyl)zirconium hydridochloride (Schwartz's reagent) in solvents, such as THF, diethyl ether, toluene or DCM, at reaction temperatures of preferably between −78° C. and 50° C., can be employed. For the 2 step process carboxylic acid derivatives of the general formula Z are first reduced to the corresponding alcohols with a suitable reducing agent, preferably selected from the group consisting of diisobutyl aluminium hydride, lithium aluminium hydride, lithium-tri-tert-butoxyaluminium hydride, sodium-bis(2-methoxyethoxy)-aluminium hydride, sodium boron hydride, aluminium hydride, $BH_3 \times DMS$ and lithium borohydride, in a suitable solvent, such as THF, diethyl ether, toluene or DCM, at temperatures of preferably −78° C. to 200° C. In a second step the alcohol is oxidized by a suitable oxidising agent, such as TEMPO/NaOCl, manganese(IV) oxide, pyridinium dichromate, pyridinium chlorochromate, Swern oxidation conditions [$(COCl)_2$/DMSO/triethylamine] or Dess-Martin periodinone, where necessary in the presence of acetic acid or sodium acetate, in a suitable solvent such as dichloromethane, chloroform, diethylether or mixtures thereof, at temperatures of preferably −78° C. to 200° C., to yield aldehydes having the general formula V.

Compounds having the general formula V are then reacted with methyl vinyl ketone in the presence of a suitable base, for example potassium hydroxide, sodium hydroxide or lithium hydroxide, or a suitable acid, for example HCl or sulfuric acid, in a suitable solvent, for example i-propanol, ethanol, methanol, toluene, benzene or corresponding blends, at a reaction temperature of 0° C. to +200° C., optionally under Dean-Stark conditions, to form compounds having the general formula W.

The conversion of compounds of formula V into compounds having the general formula X is known from the literature, for example from (a) Bioorg. Med. Chem. Lett., 2001, 11, 1293-1296, (b) WO 2008109178 or (c) WO 2008109181.

Compounds having the general formula W are reduced by hydrogenolysis with homogeneous or heterogeneous catalysts or by reaction with reducing agents to form compounds having the general formula X. A suitable homogeneous catalyst is, for example, tris(triphenylphosphane)rhodium chloride in solvents such as e.g. benzene or toluene. Suitable heterogeneous catalysts are, for example, Pt on carbon, palladium on carbon, Raney nickel or $Pt_2O$ in solvents such as, for example, acetic acid, methanol, ethanol, ethyl acetate, hexane, chloroform, water or blends of these solvents. Acids such as sulfuric acid or hydrochloric acid, for example, or bases such as e.g. potassium carbonate, can optionally be added. A suitable reducing agent is, for example, L-selectride in THF.

If the protective group is to be eliminated at the same time under these conditions, this or another suitable protective group, for example CBz, Boc, benzyl or p-methoxybenzyl, is reintroduced by methods known to the person skilled in the art to obtain compounds having the general formula X. Alternatively in this case the hydrogenolysis can take place in the presence of di-tert-butyl dicarbonate in order to achieve the reintroduction of a suitable protective group in one stage.

Compounds having the general formula X are converted by means of Method A or Method B into compounds having the general formula Y.

Method A

Compounds having the general formula T are converted into benzotriazole aminal in an aminal formation reaction by reaction with an amine and 1H-benzotriazole, persons skilled in the art being aware that the benzotriazole aminal can be present both in equilibrium and in the 1H and 2H form. Benzene, toluene, ethanol, diethyl ether or THF, for example, are suitable as solvents. The use of a Dean-Stark water separator, molecular sieve or other dehydrating agent may be necessary. The reaction time at a reaction temperature from +20° C. to +110° C. can be between 1 and 20 h. The benzotriazole aminal obtained as intermediate is then converted into compounds having the general formula Y with metal organyls such as magnesium, zinc or lithium organyls in organic solvents, for example diethyl ether, dioxane or THF.

Method B

Compounds having the general formula T are converted into nitrilamines by adding an amine and a cyanide source. This reaction can take place in one or two stages. In the two-stage variant a nitrile alcohol is first formed and isolated. Formation of the nitrile alcohol can take place by reacting compounds having the general formula T with HCN, KCN or NaCN as the cyanide source, wherein if NaCN and KCN are used, the necessary cyanide is released by the addition of sodium hydrogen sulfite, sulfuric acid, acetic acid or hydrochloric acid, for example. Preferred solvents are water, methanol, ethanol, THF, piperidine, diethyl ether or a blend of these solvents. Trimethyl silyl cyanide, for example, is likewise suitable as the cyanide source; the cyanide can be released by means of boron trifluoride etherate, $InF_3$ or HCl, for example. Preferred solvents are water or toluene. Another suitable cyanide source is (cyano-C)diethyl aluminium, for example. THF, toluene or a blend of the two solvents can be used as solvent. The reaction temperature for all variants is preferably between −78° C. and +25° C. For the reaction of the nitrile alcohol with the amine to form nitrilamines, alcohols such as methanol or ethanol are particularly suitable as solvent. The reaction temperature can be between 0° C. and +25° C. In the single-stage variant the nitrile alcohol primary product is formed in situ and reacted with the amine to form nitrilamines. The nitrilamine obtained as intermediate is then reacted with metal organyls such as magnesium, zinc or lithium organyls in organic solvents, e.g., diethyl ether, dioxane or THF, to form compounds corresponding to formula Y.

Amines having the general formula (A) are obtained by eliminating the amine protective group from compounds corresponding to formula Y using methods known to persons skilled in the art.

Preferred protective groups, in particular Boc and Cbz, can be eliminated as follows. BOC protective groups can be eliminated in at least one solvent, preferably selected from the group consisting of acetonitrile, diethyl ether, tetrahydrofuran, methanol, ethanol, dichloromethane, dioxane and dimethyl formamide, with an acid, preferably selected from the group consisting of trifluoroacetic acid, hydrochloric acid, methanesulfonic acid and sulfuric acid, at temperatures of preferably 0° C. to 110° C. Cbz protective groups can be removed under acid conditions. This acid elimination can be performed, for example, by reaction with an HBr/glacial acetic acid blend, a blend of TFA in dioxane/water or HCl in methanol or ethanol. Also suitable, however, are reagents such as, for example, $Me_3SiI$ in solvents such as, for example, DCM, chloroform or acetonitrile, $BF_3$ etherate with addition of ethanethiol or $Me_2S$ in solvents such as, for example, DCM, a blend of aluminium chloride/anisol in a blend of DCM and nitromethane or triethylsilane/$PdCl_2$ in methanol with addition of triethylamine. A further method is the hydrogenolytic elimination of the protective group under elevated pressure or without the use of pressure, with the aid of catalysts such as, for example, Pd on carbon, $Pd(OH)_2$, $PdCl_2$, Raney nickel or $PtO_2$ in solvents such as, for example, methanol, ethanol, 2-propanol, THF, acetic acid, ethyl acetate, chloroform, optionally with the addition of HCl, formic acid or TFA.

Pharmacological Methods
1. Functional Investigation on the Bradykinin Receptor 1 (B1R)

The agonistic or antagonistic action of substances can be determined on the bradykinin 1 receptor (B1R) of the human and rat species with the following assay. According to this assay, the $Ca^{2+}$ inflow through the channel is quantified with the aid of a $Ca^{2+}$-sensitive dye (Fluo-4 type, Molecular Probes Europe BV, Leiden, The Netherlands) in a fluorescent imaging plate reader (FLIPR, Molecular Devices, Sunnyvale, USA).

2. Method:

Chinese hamster ovary cells (CHO K1 cells) which are stably transfected with the human B1R gene (hB1R cells) or the B1R gene of the rat (rB1R cells) are used. For functional investigations, these cells are plated-out onto black 96-well plates with a clear base (BD Biosciences, Heidelberg, Germany or Greiner, Frickenhausen, Germany) in a density of 20,000-35,000 cells/well. Overnight, the cells are incubated at 37° C. and 5% $CO_2$ in culture medium (hB1R cells: Nutrient Mixture Ham's F12, Gibco Invitrogen GmbH, Karlsruhe, Germany or DMEM, Sigma-Aldrich, Taufkirchen, Germany; rB1R cells: D-MEM/F12, Gibco Invitrogen, Karlsruhe, Germany) with 10 vol. % FBS (foetal bovine serum, Gibco Invitrogen GmbH, Karlsruhe, Germany or PAN Biotech GmbH, Aidenbach, Germany). On the following day the cells are loaded with 2.13 µM Fluo-4 (Molecular Probes Europe BV, Leiden, The Netherlands) in HBSS buffer (Hank's buffered saline solution, Gibco Invitrogen GmbH, Karlsruhe, Germany) with 2.5 mM probenecid (Sigma-Aldrich, Taufkirchen, Germany) and 10 mM HEPES (Sigma-Aldrich, Taufkirchen, Germany) for 60 min at 37° C. The plates are the washed twice with HBSS buffer, and HBSS buffer which additionally contains 0.1% BSA (bovine serum albumin; Sigma-Aldrich, Taufkirchen, Germany), 5.6 mM glucose and 0.05% gelatine (Merck KGaA, Darmstadt, Germany) is added. After a further incubation of 20 minutes at room temperature, the plates are inserted into the FLIPR for $Ca^{2+}$ measurement. Alternatively they are washed with buffer A (15 mM HEPES, 80 mM NaCl, 5 mM KCl, 1.2 mM $CaCl_2$, 0.7 mM $MgSO_4$, 2 g/l glucose, 2.5 mM probenecid) and loaded with buffer A with added 2.5 µM Fluo-4 and 0.025% Pluronic F127 (Sigma-Aldrich, Taufkirchen, Germany). The cells are then washed twice with buffer A and incubated for 30 minutes with buffer A, which additionally contains 0.05% BSA and 0.05% gelatine, at room temperature and then used for $Ca^{2+}$ measurement in the FLIPR.

The $Ca^{2+}$-dependent fluorescence is measured here before and after addition of substances ($\lambda_{ex}$=488 nm, $\lambda_{em}$=540 nm). The quantification is performed by measuring the highest fluorescence intensity (FC, fluorescence counts) over time.

3. FLIPR Assay:

The FLIPR protocol comprises two additions of substance. Test substances (10 µM) are first pipetted onto the cells and the $Ca^{2+}$ inflow is compared with the control (hB1R: Lys-Des-$Arg^9$ bradykinin>=50 nM; rB1R: Des-$Arg^9$ bradykinin 10 µM). The value in % activation based on the $Ca^{2+}$ signal after addition of Lys-Des-$Arg^9$ bradykinin (>=50 nM) or Des-$Arg^9$ bradykinin (10 µM) is obtained therefrom. After incubation for 10-20 minutes, Lys-Des-$Arg^9$ bradykinin (hB1R) or Des-$Arg^9$ bradykinin (rB1R) is applied in the $EC_{80}$ concentration and the inflow of $Ca^{2+}$ is likewise determined. Antagonists lead to a suppression of the $Ca^{2+}$ inflow. The % inhibition in comparison with the maximum achievable inhibition is calculated. The substances are added in varying concentrations in order to determine the $IC_{50}$ value. Double or triple determinations (n=2 or n=3) are performed and these are repeated in at least one further independent experiment (N>=2). The compounds preferably exhibit a B1R antagonistic action on the human receptor and/or on the rat receptor. The following data is provided in the table below by way of example: ("% Inh. (rat B1R) 10 µM" denotes "% inhibition rat B1R at 10 µM" and "% Inh. (hum. B1R) 10 µM" denotes "% inhibition human B1R at 10 µM").

4. Method for Determining the Affinity to the Human µ-Opiate Receptor

The receptor affinity to the human µ-opiate receptor is determined in a homogeneous batch in microtitre plates. To this end, dilution series of the substances to be tested are incubated for 90 minutes at room temperature with a receptor membrane preparation (15-40 µg protein/250 µl incubation batch) of CHO-K1 cells, which express the human µ-opiate receptor (RB-HOM receptor membrane preparation from PerkinElmer Life Sciences, Zaventem, Belgium), in the presence of 1 nmol/l of the radioactive ligand [$^3$H] naloxone (NET719, PerkinElmer Life Sciences, Zaventem, Belgium) and 1 mg of WGA-SPA beads (wheat germ agglutinin SPA beads from Amersham/Pharmacia, Freiburg, Germany) in a total volume of 250 µl. 50 mmol/l of tris-HCl supplemented with 0.06% bovine serum albumin are used as the incubation buffer. In order to determine the non-specific binding, 100 µmol/l of naloxone are also added. At the end of the ninety-minute incubation period the microtitre plates are centrifuged for 20 minutes at 1000 g and the radioactivity is measured in a β counter (Microbeta-Trilux, PerkinElmer Wallac, Freiburg, Germany). The percentage displacement of the radioactive ligand from its binding to the human µ-opiate receptor is determined at a test substance concentration of 1 µmol/l and stated as the percentage inhibition of the specific binding. Starting from the percentage displacement due to differing concentrations of the test substances, $IC_{50}$ inhibition concentrations are calculated which bring about a 50-percent displacement of the radioactive ligand. $K_i$ values for the test substances are obtained by extrapolation using the Cheng-Prusoff equation.

The invention is described in further detail below with reference to illustrative examples. These explanations are provided merely as examples and do not limit the overall scope of the invention.

EXAMPLES

The chemicals and solvents used were obtained commercially from the usual suppliers (Acros, Aldrich, Fluka, Lancaster, Maybridge, TCI, Fluorochem, Tyger, ABCR, Fulcrum, FrontierScientific, Milestone, etc.). The yields of the compounds produced are not optimized. The blending ratios of solvents are always given in the volume/volume ratio. Equivalent quantities of the reagents used, as well as the solvent quantities, reaction temperatures and times may vary slightly in different reactions performed using the same method. Processing and purification methods were adapted according to the characteristic properties of the compounds. If not stated otherwise silica gel was employed as the stationary phase for purification by column chromatography. The individual compounds were analyzed by high performance liquid chromatography—mass spectroscopy (HPLC-MS) and/or nuclear magnetic resonance (NMR):

NMR: Bruker 440 MHz or 600 MHz instrument

Materials and methods for LC-MS analysis: HPLC: Waters Alliance 2795 with PDA Waters 2998; MS: Micromass Quattro Micro™ API; column: Waters Atlantis® T3, 3 µm, 100 Å, 2.1×30 mm; column temperature: 40° C., Eluent A: water+ 0.1% formic acid; Eluent B: acetonitrile+0.1% formic acid;

gradient: 0% B to 100% B in 8.8 min, 100% B for 0.4 min, 100% B to 0% B in 0.01 min, 0% B for 0.8 min; flow rate: 1.0 ml/min; ionisation: ES+, 25 V; make-up: 100 µl/min 70% methanol+0.2% formic acid; UV: 200-400 nm A) Single Compound Syntheses 1.) Synthesis of the Acid Structural Units (S)

Synthesis of 2-((1-(4-methoxy-2,6-dimethylphenyl-sulfonyl)piperidin-2-yl)methoxy)acetic acid (S1)

Stage 1: (1-(4-Methoxy-2,6-dimethylphenylsulfonyl)piperidin-2-yl)methanol

Piperidin-2-ylmethanol (1.1 eq) was dissolved in dichloromethane (4 ml/mmol), cooled, and triethylamine (2.5 eq) was added. A solution of 4-methoxy-2,6-dimethylbenzenesulfonyl chloride (1 eq) in dichloromethane (2 ml/mmol) was added dropwise at 0° C., then the mixture was stirred for 90 min at room temperature. Hydrogen chloride solution (eq, 0.5 mol/l, 2 ml/mmol) was added, the mixture stirred for 15 min and the phases separated. The organic phase was washed with water, dried over sodium sulfate and concentrated to small volume under vacuum. The crude product was used in the next stage with no further purification. Yield: 20%

Stage 2: tert-Butyl 2-((1-(4-methoxy-2,6-dimethylphenylsulfonyl)piperidin-2-yl)methoxy)acetate tetra-n-Butylammonium chloride (0.33 eq) and sodium hydroxide solution (5 ml/mmol, 35%) were added to a cooled solution of (1-(4-methoxy-2,6-dimethylphenylsulfonyl)piperidin-2-yl)methanol (1 eq) in toluene (5 ml/mmol) at 0° C. tert-Butylbromoacetate (1.5 eq) was then slowly added dropwise at 0° C. After stirring the mixture at room temperature for 90 min the phases were separated, the organic phase was washed with water to a neutral pH, dried over sodium sulfate and concentrated to small volume under vacuum. The crude product was used in the next stage with no further purification. Yield: 64%

Stage 3: 2-((1-(4-Methoxy-2,6-dimethylphenylsulfonyl)piperidin-2-yl)methoxy)acetic acid (S1)

tert-Butyl 2-((1-(4-methoxy-2,6-dimethylphenylsulfonyl)piperidin-2-yl)methoxy)acetate (1 eq) was dissolved in dichloromethane (10 ml/mmol), cooled, and trifluoroacetic acid (13 eq) was added slowly at room temperature. After stirring for 2 h at room temperature, the reaction mixture was concentrated to small volume under vacuum and dried. The crude product was used in the next stage with no further purification. Yield: quantitative Synthesis of (S)-2-((1-(4-methoxy-2,6-dimethylphenylsulfonyl)piperidin-2-yl)methoxy)acetic acid (S2)

Stage 1: (S)-Piperidin-2-ylmethanol (S)-Piperidine-2-carboxylic acid (2 g, 15.5 mmol) was introduced into tetrahydrofuran (20 ml), boron trifluoride etherate (2.1 ml, 117.1 mmol) was added, followed by boron dimethyl sulfide in tetrahydrofuran (dropwise, 3 ml, 30.9 mmol). The reaction mixture was then refluxed for 16 h. The mixture was quenched with ice-cold methanol (10 ml), hydrogen chloride solution was added dropwise (conc. eq, 3 ml), and the mixture was refluxed for 30 min. After cooling, the mixture was alkalised with dilute sodium hydroxide solution (4%) and extracted with dichloromethane (3×50 ml). The combined organic phases were dried over sodium sulfate and concentrated to small volume under vacuum. The crude product was used in the next stage with no further purification. Yield: 44%

Stage 2: (S)-(1-(4-Methoxy-2,6-dimethylphenylsulfonyl)piperidin-2-yl)methanol

The reaction was performed starting from (S)-piperidin-2-ylmethanol in an analogous manner to stage 2 acid (S1). Yield: 20%

Stage 3: (S)-tert-Butyl 2-((1-(4-methoxy-2,6-dimethylphenylsulfonyl)piperidin-2-yl)methoxy)acetate The reaction was performed starting from (S)-(1-(4-methoxy-2,6-dimethylphenylsulfonyl)piperidin-2-yl)methanol in an analogous manner to stage 3 acid (S1). Yield: 64%

Stage 4: (S)-2-((1-(4-Methoxy-2,6-dimethylphenylsulfonyl)piperidin-2-yl)methoxy)acetic acid (S2)

The reaction was performed starting from (S)-tert-butyl 2-((1-(4-methoxy-2,6-dimethylphenylsulfonyl)piperidin-2-yl)methoxy)acetate in an analogous manner to stage 4 acid (S1). Yield: quantitative Synthesis of 2-(2-(N-cyclopropyl-4-methoxy-2,6-dimethylphenylsulfonamido)ethoxy)acetic acid (S3)

Stage 1: 2-(Cyclopropylamino)ethanol

A solution of cyclopropylamine (20 mmol) and bromoethanol (8 mmol) in ethanol (20 ml) was heated for 16 h at 50° C. The solvent was removed and the residue co-evaporated with toluene (2×10 ml). After drying under high vacuum the crude product was used directly in the next stage with no further processing. Yield: 65%

Stage 2: N-Cyclopropyl-N-(2-hydroxyethyl)-4-methoxy-2,6-dimethylphenylsulfonamide A solution of 4-methoxy-2,6-dimethylbenzenesulfonyl chloride (7 mmol) in dichloromethane (12 ml) was slowly added dropwise to a solution of 2-(cyclopropylamino)ethanol (8 mmol) in dichloromethane (24 ml) and triethylamine (2.5 eq), cooled to 0° C. On completion of the addition the mixture was stirred for 90 min at 25° C. until the reaction was complete. The mixture was diluted with dichloromethane (200 ml) and washed with water and saturated NaCl solution. The organic phase was dried over MgSO$_4$, filtered and concentrated completely to obtain the desired product. Yield: 20%

Stage 3: tert-Butyl 2-(2-(N-cyclopropyl-4-methoxy-2,6-dimethylphenylsulfonamido)ethoxy)acetate tetra-n-Butylammonium chloride (0.33 eq) and 35% sodium hydroxide solution (18 ml) were added to a solution of N-cyclopropyl-N-(2-hydroxyethyl)-4-methoxy-2,6-dimethylphenylsulfonamide (3.3 mmol) in toluene (18 ml), cooled to 0° C. tert-Butylbromoacetate (1.5 eq) was added slowly to this mixture at 0° C. On completion of the addition the mixture was stirred for 90 min at 25° C. until the reaction was complete. The organic phase was separated off, washed with water until a neutral pH was measured, dried over MgSO$_4$, filtered and concentrated completely to obtain the desired product. Yield: 90%

Stage 4: 2-(2-(N-Cyclopropyl-4-methoxy-2,6-dimethylphenylsulfonamido)ethoxy)acetic acid (S3)

Trifluoroacetic acid (13 eq) was added dropwise to a solution of tert-butyl 2-(2-(N-cyclopropyl-4-methoxy-2,6-dimethylphenylsulfonamido)ethoxy)acetate in dichloromethane (10 ml/mmol) at 0° C. and the resulting solution was stirred for 2 h at 25° C. The mixture was concentrated completely and traces of trifluoroacetic acid removed under high vacuum. The crude product was used directly in the next stage with no further processing.

Synthesis of (S)-2-((1-(4-methoxy-2,6-dimethylphenylsulfonyl)indolin-2-yl)methoxy)acetic acid (S4)

Stage 1: (S)-Indolin-2-ylmethanol

BH$_3$-DMS solution (18.4 mmol, 2 eq) was added dropwise to a solution of (S)-indoline-2-carboxylic acid (9.2 mmol, 1.0 eq) in THF (18 ml) and the mixture was refluxed for 12 h. Methanol (7.5 ml) and concentrated HCl (2.5 ml) were added to the reaction mixture with cooling, then refluxing was continued for a further 2 hours. The solvent was removed under vacuum and the residue made alkaline with 40% NaOH solution and extracted with DCM. The organic phase was washed with saturated sodium chloride solution, dried (Na$_2$SO$_4$) and concentrated to small volume under vacuum. The crude product was processed by column chromatography. Yield: 87%

Stage 2: (S)-(1-(4-Methoxy-2,6-dimethylphenylsulfonyl)indolin-2-yl)methanol

4-Methoxy-2,6-dimethylbenzenesulfonic acid chloride (3.83 mmol, 1.0 eq) in DCM (5 ml) was added dropwise to a cooled (0° C.) solution of (S)-indolin-2-ylmethanol (4.60 mmol, 1.2 eq) and triethylamine (2.5 eq) in DCM (20 ml) and the mixture was stirred for 2 h at room temperature. The reaction mixture was diluted with DCM and washed with water and saturated sodium chloride solution. It was dried over sodium sulfate and concentrated to small volume under vacuum. The crude product was processed by column chromatography. Yield: 72%

Stage 3: (S)-tert-Butyl 2-((1-(4-methoxy-2,6-dimethylphenylsulfonyl)indolin-2-yl)methoxy)acetate 35% sodium hydroxide solution (10 ml) was added to a cooled (0° C.) solution of (S)-(1-(4-methoxy-2,6-dimethylphenylsulfonyl)indolin-2-yl)methanol (3.3 mmol, 1.0 eq) and tetra-n-butylammonium chloride (1.1 mmol, 0.33 eq) in toluene (20 ml). tert-Butylbromoacetate (1.5 eq) was added slowly to this mixture and the mixture was stirred for 2 h at room temperature. The organic phase was separated off and the aqueous phase extracted with ethyl acetate. The combined organic phases were washed with water and saturated sodium chloride solution, dried over Na$_2$SO$_4$ and concentrated to small volume under vacuum. The crude product was processed by column chromatography. Yield: 50%

Stage 4: (S)-2-((1-(4-Methoxy-2,6-dimethylphenylsulfonyl)indolin-2-yl)methoxy)acetic acid (S4)

TFA (1.5 ml) was added to a cooled (0° C.) solution of (S)-tert-butyl 2-((1-(4-methoxy-2,6-dimethylphenylsulfonyl)indolin-2-yl)methoxy)acetate (0.5 mmol) in DCM (6 ml) and the mixture was stirred for 2 h at room temperature. The solvent was removed under vacuum and the residue used in the subsequent stage.

Synthesis of (3R)-(naphthyl-2-sulfonamido)-3-phenylpropionic acid (S5)

Stage 1: (R)-3-Amino-3-phenylpropionic acid methyl ester hydrochloride

Thionyl chloride (9 mmol) was added to a solution of R-β-phenylalanine (6 mmol) in methanol (50 ml) at 25° C. while stirring. The reaction mixture was then refluxed for 16 h and the complete conversion confirmed by analysis by thin-layer chromatography. The solvent was removed under vacuum to obtain the hydrochloride. Yield: quantitative Stage 2: (R)-3-(Naphthyl-2-sulfonamido)-3-phenylpropionic acid methyl ester (R)-3-Amino-3-phenylpropionic acid methyl ester hydrochloride (1.1 eq) was dissolved in dichloromethane (4 ml/mmol), cooled, and triethylamine (2.5 eq) was added. A solution of 2-naphthylsulfonyl chloride (1 eq) in dichloromethane (2 ml/mmol) was added dropwise at 0° C., then the mixture was stirred for 90 min at room temperature. Hydrogen chloride solution (eq, 0.5 mol/l, 2 ml/mmol) was added, the mixture stirred for 15 min and the phases separated. The organic phase was washed with water, dried over sodium sulfate and concentrated to small volume under vacuum. The crude product was used in the next stage with no further purification. Yield: 70%

Stage 3: (R)-3-(Naphthyl-2-sulfonamido)-3-phenylpropionic acid (S5)

Lithium hydroxide monohydrate (5 eq) was added to a suspension of (R)-3-(naphthyl-2-sulfonamido)-3-phenylpropionic acid methyl ester (1 eq) in methanol (7.5 ml/mmol) and water (2.5 ml/mmol) and the reaction mixture was stirred for 72 h at 25° C. The methanol was removed under vacuum and the aqueous phase acidified with 1(N)HCl and filtered. The solid was taken up in a mixture of acetone (30 ml/mmol) and methanol (4 ml/mmol) and stirred for 1 h. Then the solid was filtered off and dried under vacuum. Yield: 70%

Synthesis of (S)-2-((1-(2-chloro-6-methylphenylsulfonyl)piperidin-2-yl)methoxy)acetic acid (S6)

The synthesis was performed starting from (S)-piperidin-2-ylmethanol (see stage 1 acid (S2)) in an analogous manner to the synthesis of acid (S1):

Stage 1: (S)-(1-(2-Chloro-6-methylphenylsulfonyl)piperidin-2-yl)methanol

The reaction was performed starting from (S)-piperidin-2-ylmethanol in an analogous manner to stage 2 acid (S1). Yield: 30%

Stage 2: (S)-tert-Butyl 2-((1-(2-chloro-6-methylphenylsulfonyl)piperidin-2-yl)methoxy)acetate The reaction was performed starting from (S)-(1-(2-chloro-6-methylphenylsulfonyl)-piperidin-2-yl)methanol in an analogous manner to stage 3 acid (S1). Yield: 60%

Stage 3: (S)-2-((1-(2-chloro-6-methylphenylsulfonyl)piperidin-2-yl)methoxy)acetic acid (S6)

The reaction was performed starting from (S)-tert-butyl 2-((1-(2-chloro-6-methylphenylsulfonyl)piperidin-2-yl)methoxy)acetate in an analogous manner to stage 4 acid (S1). Yield: quantitative

Synthesis of 3-(1-(4-chloro-2,5-dimethylphenylsulfonyl)piperidin-2-yl)propionic acid (S7)

Stage 1: Ethyl 3-(piperidin-2-yl)propionic acid ethyl ester hydrochloride

Hydrogen chloride in ethanol (saturated, 40 ml) was added to 3-piperidin-2-yl-propionic acid hydrochloride (1 g, 5 mmol) at 0° C. and the mixture was stirred for 16 h at 25° C. (analysis by thin-layer chromatography). The solvent was removed under vacuum and the crude product used in the next stage without purification. Yield: quantitative

Stage 2: 3-(1-(4-Chloro-2,5-dimethylphenylsulfonyl)piperidin-2-yl)propionic acid ethyl ester 4-Chloro-2,5-dimethyl-benzenesulfonyl chloride (1 g, 3.8 mmol) was added to a solution of ethyl 3-(piperidin-2-yl)propionic acid ethyl ester hydrochloride (1.1 g, 4.6 mmol) in dichloromethane (15 ml) while stirring, the mixture was cooled to 0° C., and triethylamine (1.6 ml, 11.5 mmol) was added dropwise over 15 min. The mixture was stirred for 4 h at 0° C., then diluted with dichloromethane, washed with water and saturated sodium chloride solution, dried over sodium sulfate and concentrated to small volume under vacuum. The crude product was purified with ethyl acetate/hexane (9:1) by column chromatography. Yield: 50%

Stage 3: 3-(1-(4-Chloro-2,5-dimethylphenylsulfonyl)piperidin-2-yl)propionic acid (S7)

Methanol/$H_2O$ (3:1, 90 ml) was added to 3-(1-(4-chloro-2,5-dimethylphenylsulfonyl)piperidin-2-yl)propionic acid ethyl ester (3.48 g, 9 mmol) at 25° C., the mixture was cooled to 0° C., lithium hydroxide (0.75 g, 18 mmol) was added, and the mixture was stirred for 16 h at 25° C. The solvent was removed under vacuum, the residue taken up in water and washed with dichloromethane. The aqueous phase was carefully acidified with hydrogen chloride solution (1 mol/l) and extracted with ethyl acetate. This organic phase was washed with water and saturated sodium chloride solution, dried over sodium sulfate and concentrated to small volume under vacuum. Yield: 89%

Synthesis of 4-(1-(4-methoxy-2,6-dimethylphenylsulfonyl)piperidin-2-yl)butanoic acid (S8)

Stage 1: Methyl 4-(piperidin-2-yl)butanoic acid methyl ester hydrochloride

Hydrogen chloride in methanol 1.25 mol/l (58 ml, 72.43 mmol) was added to 4-piperidin-2-ylbutanoic acid hydrochloride (1.5 g, 7.243 mmol), the mixture was refluxed for 6 h, cooled to room temperature and stirred for 3 d. Analysis by thin-layer chromatography showed that reactant was still present. Additional hydrogen chloride in methanol was added (4 ml) and the mixture refluxed for 3 h. The reaction mixture was concentrated to small volume under vacuum and taken up in ethanol/diethyl ether (1:1) (5 ml). The solution was dropped slowly into ice-cold diethyl ether (300 ml), the resulting suspension stirred for 1 h in an ice bath, the solid siphoned off, washed with diethyl ether and dried under vacuum. Yield: 1.21 g (75%)

Stage 2: Methyl 4-(1-(4-methoxy-2,6-dimethylphenylsulfonyl)piperidin-2-yl)butanoic acid methyl ester Methyl 4-(piperidin-2-yl)butanoic acid methyl ester hydrochloride (1.26 g, 5.683 mmol) was dissolved in dichloromethane (25 ml) and triethylamine (4 ml, 28.417 mmol) and a solution of 4-methoxy-2,6-dimethylbenzenesulfonic acid chloride (2.67 g, 11.37 mmol) in dichloromethane (10 ml) was added. The mixture was stirred overnight at room temperature. 1 mol/l HCl solution (10 ml) was added to the reaction mixture, followed by phase separation and extraction of the aqueous phase with dichloromethane (2×20 ml). The combined organic phases were washed with saturated sodium chloride solution (20 ml), dried over sodium sulfate and concentrated to small volume under vacuum. The crude product was purified by column chromatography (silica gel) with hexane/dichloromethane/diethyl ether (400:100:50). Yield: 1.65 g (75%)

Stage 3: 4-(1-(4-Methoxy-2,6-dimethylphenylsulfonyl)piperidin-2-yl)butanoic acid (S8)

Methyl 4-(1-(4-methoxy-2,6-dimethylphenylsulfonyl)piperidin-2-yl)butanoic acid methyl ester (1.65 g, 4.3 mmol) was dissolved in water (10 ml) and methanol (35 ml) and lithium hydroxide (0.3 g, 12.9 mmol) was added. The mixture was stirred for 3 d at room temperature, then methanol was distilled off under vacuum and ethyl acetate (50 ml) and HCl solution (1 mol/l, 10 ml) added to the residue. Phase separation, extraction with ethyl acetate (2×50 ml), the combined organic phases were dried over sodium sulfate and concentrated to small volume under vacuum. Yield: 1.56 g (98%)

Synthesis of 2-(1-(3-(trifluoromethyl)phenylsulfonyl)piperidin-2-yl)acetic acid (S9)

Stage 1: Methyl 2-(piperidin-2-yl)acetate hydrochloride

Thionyl chloride (5.5 ml, 75 mmol) was added to a solution of 2-carboxymethylpiperidine-1-carboxylic acid tert-butyl ester (6 g, 25 mmol) in methanol (60 ml) while stirring and the mixture was then refluxed for 16 h. The solvent was removed under vacuum and the crude product used in the next stage without purification. Yield: 90%

Stage 2: Methyl 2-(1-(3-(trifluoromethyl)phenylsulfonyl)piperidin-2-yl)acetate A solution of 3-(trifluoromethyl)benzenesulfonyl chloride (1 eq) in dichloromethane (1.6 ml/mmol) was added dropwise to a cooled solution (0° C.) of methyl 2-(piperidin-2-yl)acetate hydrochloride (1.1 eq) in dichloromethane (40 ml/mmol) and triethylamine (2.5 eq). The mixture was stirred for 90 min at 25° C., after which the reaction was completed (thin-layer chromatographic analysis). Hydrogen chloride solution (0.5 mol/l, 2 ml/mmol) was added and the mixture was stirred for 15 min. The organic phase was separated off, washed with water, dried over sodium sulfate and concentrated to small volume under vacuum. Yield: 80%

Stage 3: 2-(1-(3-(Trifluoromethyl)phenylsulfonyl) piperidin-2-yl)acetic acid (S9)

A solution of lithium hydroxide (1 g, 22 mmol) in water (44 ml) was added dropwise to a solution of methyl 2-(1-(3-(trifluoromethyl)phenylsulfonyl)piperidin-2-yl)acetate (4.38 g, 12 mmol) in tetrahydrofuran (176 ml) while stirring at 0° C. The mixture was stirred for 16 h at 25° C. The solvent was removed under vacuum, the residue dissolved in water and washed with diethyl ether. The aqueous phase was carefully acidified with citric acid solution (10%) and extracted with ethyl acetate. This organic phase was washed with water and saturated sodium chloride solution, dried over sodium sulfate, filtered and concentrated to small volume under vacuum. The crude product was used in the next stage with no further purification. Yield: 90%

Synthesis of (R)-2-(1-(4-methoxy-2,6-dimethylphenylsulfonyl)-3-oxo-1,2,3,4-tetrahydropyrazin-2-yl) acetic acid (S10)

Stage 1: (S)-4-tert-Butoxy-2-(4-methoxy-2,6-dimethylphenylsulfonamido)-4-oxobutyric acid Sodium bicarbonate (1.5 eq) was added to a suspension of (S)-2-amino-4-tert-butoxy-4-oxobutanoic acid (5.1 mmol, 1.2 eq) in dioxane/water (1:1, 20 ml) and the mixture was stirred for 30 min at room temperature. A solution of 4-methoxy-2,6-dimethylbenzenesulfonic acid chloride (4.3 mmol, 1.0 eq) in dioxane (10 ml) was added and the reaction mixture stirred for 16 h at room temperature. On completion of the reaction the organic solvent was removed under vacuum and the aqueous phase acidified with 10% HCl (eq). Extraction was then performed with DCM and the organic phase was washed with saturated sodium chloride solution, dried ($Na_2SO_4$) and concentrated to small volume under vacuum. Yield: 45%.

Stage 2: (S)-tert-Butyl 4-(2,2-dimethoxyethylamino)-3-(4-methoxy-2,6-dimethylphenylsulfonamido)-4-oxobutanoate Diisopropylethylamine (2.5 eq) followed by HOBT (1.0 eq) and EDCI (1.5 eq) was added to a solution of (S)-4-tert-butoxy-2-(4-methoxy-2,6-dimethylphenyl-sulfonamido)-4-oxobutyric acid (1.91 mmol, 1.0 eq) in DCM (10 ml/mmol) at 0° C. The resulting solution was stirred for 15 min at 25° C., cooled to 0° C. again and 2,2-dimethoxyethanamine (1.2 eq) was added. The reaction mixture was stirred for 16 h at 15° C. It was then diluted with DCM and extracted with saturated ammonium chloride solution, saturated sodium chloride solution, saturated sodium bicarbonate solution and finally saturated sodium chloride solution. The organic phase was dried ($Na_2SO_4$) and concentrated to low volume under vacuum. The crude product was processed by column chromatography. Yield: 70%

Stage 3: (S)-tert-Butyl 2-(1-(4-methoxy-2,6-dimethylphenylsulfonyl)-3-oxo-1,2,3,4-tetrahydropyrazin-2-yl)acetate PTSA (0.62 eq) was added to a solution of (S)-tert-butyl 4-(2,2-dimethoxyethylamino)-3-(4-methoxy-2,6-dimethylphenylsulfonamido)-4-oxobutanoate (1.26 mmol) in dioxane (12 ml) and the mixture was stirred for 16 h at room temperature. The solvent was removed under vacuum and the residue taken up in ethyl acetate. The organic phase was extracted with water and saturated sodium chloride solution, dried ($Na_2SO_4$) and concentrated to small volume under vacuum. The crude product was processed by column chromatography. Yield: 35%

Stage 4: (S)-2-(1-(4-methoxy-2,6-dimethylphenylsulfonyl)-3-oxo-1,2,3,4-tetrahydropyrazin-2-yl)acetic acid (S10)

TFA (1.5 ml) was added to a cooled (0° C.) solution of (S)-tert-butyl 2-(1-(4-methoxy-2,6-dimethylphenylsulfonyl)-3-oxo-1,2,3,4-tetrahydropyrazin-2-yl)acetate (210 mg, 1 eq) in DCM (6 ml) and the mixture was stirred for 2 h at room temperature. The solvent was removed under vacuum and the residue used in the subsequent stage.

Synthesis of Sulfonyl Chloride

4-Methoxy-2,6-dimethylphenylsulfonic acid chloride

Chlorosulfuric acid (2.3 eq) in dichloromethane (0.5 ml/mmol) was slowly added dropwise over 10 min to a solution of 3,5-dimethylanisol (1 eq) in dichloromethane (1 ml/mmol) cooled to 0° C. The reaction mixture was stirred for a further 10 min and then slowly dropped into iced water (5 eq relative to chlorosulfuric acid). The phases were separated and the aqueous phase extracted with dichloromethane (repeatedly, UV analysis). The combined organic phases were dried ($Na_2SO_4$) and concentrated to small volume under vacuum. Yield: 82%

2.) Synthesis of the Amine Structural Units (A)

Synthesis of N,N-dimethyl-9-phenyl-3-azaspiro[5.5] undecan-9-amine (A1)

Stage 1: N,N-Dimethyl-8-phenyl-1,4-dioxaspiro[4.5] decan-8-amine

Acetic acid (30 ml) was added to a solution of 1,4-dioxaspiro[4.5]decan-8-one (128 mmol) in methanol (50 ml). The reaction mixture was cooled to 0° C. and dimethylamine solution (200 ml, 40% eq) was added dropwise. Potassium cyanide (2 eq) was added at the same temperature, then the cooling bath was removed and the reaction mixture stirred for 15 h at room temperature. It was hydrolysed with ammonium hydroxide solution (50% eq, 800 ml) and stirred for 1 h, then diluted with ethyl acetate. After phase separation the organic phase was washed with water, saturated sodium chloride solution and saturated iron sulfate solution and concentrated to small volume under vacuum. The crude dimethylaminonitrile intermediate (16 g) was dissolved in tetrahydrofuran (200 ml), cooled, and phenyl magnesium chloride solution (760 ml, 1 mol/l in hexane) was added dropwise. The cooling bath was removed and the reaction mixture stirred overnight at room temperature. It was hydrolysed with saturated ammonium chloride solution and diluted with ethyl acetate. After phase separation the organic phase was washed with water and saturated sodium chloride solution, dried over sodium sulfate and concentrated to small volume under vacuum. The crude product was purified by column chromatography (silica gel) with methanol/DCM. Yield: 59%

Stage 2: 4-(Dimethylamino)-4-phenylcyclohexanone

Hydrogen chloride solution (50 ml, 6 mol/l) was added dropwise over 10 min to N,N-dimethyl-8-phenyl-1,4-dioxaspiro[4.5]decan-8-amine (4 g, 14 mmol) at 0° C. The cooling bath was removed and the solution stirred for 16 h at 25° C. Extraction was performed with ethyl acetate (3×50 ml), the aqueous phase was rendered alkaline with sodium hydroxide solution (6 mol/l) (pH=14) and extracted with dichloromethane (4×100 ml). The combined dichloromethane phases were washed with saturated sodium chloride solution, dried over sodium sulfate, filtered and concentrated to small volume under vacuum. The crude product was purified by column chromatography (silica gel) with 5% methanol in dichloromethane. Yield: 67%

Stage 3: 9-(Dimethylamino)-2,4-dioxo-9-phenyl-3-azaspiro[5.5]undecane-1,5-dicarbonitrile Ethanolic ammonia solution (30 ml) was added at 0° C. to 4-(dimethylamino)-4-phenylcyclohexanone (3 g, 12.3 mmol) and stirred at this temperature for 24 h. The sediment was filtered off and washed with diethyl ether. The residue was dried under vacuum and used in the next stage with no further purification. Yield: 23%

Stage 4: 2,2'-(4-(Dimethylamino)-4-phenylcyclohexane-1,1-diyl)diacetic acid

Sulfuric acid (0.5 ml) was added dropwise to 9-(dimethylamino)-2,4-dioxo-9-phenyl-3-azaspiro[5.5]undecane-1,5-dicarbonitrile (0.12 g) at 0° C., the cooling bath was removed and the solution was stirred for 16 h at 25° C. After adding water (0.5 ml), the solution was refluxed for 24 h. The black sediment was filtered out, the filtrate was concentrated to small volume under vacuum, and the crude product was used in the next stage with no further purification.

Stage 5: Diethyl 3,3'-(4-(dimethylamino)-4-phenyl-cyclohexane-1,1-diyl)dipropanoate Sulfuric acid (0.25 ml) was added to a solution of 2,2'-(4-(dimethylamino)-4-phenylcyclohexane-1,1-diyl)diacetic acid in ethanol (2 ml), then the mixture was refluxed for 20 h. The reaction mixture was cooled to 25° C. and concentrated to small volume under vacuum. The residue was neutralised with sodium carbonate solution, extracted with ethyl acetate, washed with saturated sodium chloride solution, dried over sodium sulfate and concentrated to small volume under vacuum. The crude product was purified by column chromatography (silica gel) with 2% methanol in dichloromethane. Yield: 66% (after 2 stages)

Stage 6: 2,2'-(4-(Dimethylamino)-4-phenylcyclohexane-1,1-diyl)diethanol

A solution of diethyl 3,3'-(4-(dimethylamino)-4-phenylcyclohexane-1,1-diyl)dipropanoate (0.42 g, 1.22 mmol) in dry tetrahydrofuran (4 ml) was added dropwise to a suspension of lithium aluminium hydride (0.093 g, 2.43 mmol) in dry tetrahydrofuran (4 ml) at 0° C. and the mixture was then heated to 25° C. and stirred for 3 h. The reaction mixture was hydrolysed with saturated sodium sulfate solution at 0° C., filtered, and the residue washed with ethyl acetate. The combined organic phases were concentrated to small volume under vacuum and dried and used in the next stage with no further purification. Yield: 95%

Stage 7: 2,2'-(4-(Dimethylamino)-4-phenylcyclohexane-1,1-diyl)bis(ethane-2,1-diyl)dimethanesulfonate Triethylamine (0.16 ml, 1.18 mmol) was first added to an ice-cold solution of 2,2'-(4-(dimethylamino)-4-phenylcyclohexane-1,1-diyl)diethanol (0.15 g, 0.47 mmol) in dichloromethane (5 ml), followed by the dropwise addition of methanesulfonyl chloride (0.054 ml, 0.71 mmol). The cooling bath was removed and the mixture stirred for 1 h at 25° C. The reaction mixture was extracted with dichloromethane, the organic phase was washed with water and saturated sodium chloride solution, dried over sodium sulfate and concentrated to small volume under vacuum. The crude product was used in the next stage with no further purification. Yield: quantitative Stage 8: 3-Allyl-N,N-dimethyl-9-phenyl-3-azaspiro[5.5]undecan-9-amine A solution of 2,2'-(4-(dimethylamino)-4-phenylcyclohexane-1,1-diyl)bis(ethane-2,1-diyl) dimethanesulfonate (0.16 g, 0.338 mmol) in allylamine (5 ml, 66.44 mmol) was stirred for 16 h at 25° C. Allylamine was removed under vacuum, the residue taken up in ethyl acetate and washed with water and saturated sodium chloride solution, dried over sodium sulfate, filtered and concentrated to small volume under vacuum. The crude product was purified by column chromatography (Alox neutral) with 1% methanol in dichloromethane. Yield: 90%

Stage 9: N,N-dimethyl-9-phenyl-3-azaspiro[5.5]undecan-9-amine (A1)

Grubb's catalyst (0.012 g, 0.013 mmol) was added to a solution of 3-allyl-N,N-dimethyl-9-phenyl-3-azaspiro[5.5]undecan-9-amine (0.09 g, 0.266 mmol) in dry toluene (5 ml) at room temperature and the mixture was refluxed for 2 h. The sediment was filtered off over celite and rewashed with ethyl acetate. The filtrate was concentrated to small volume under vacuum and the crude product used in the next stage without further purification. Yield: quantitative Synthesis of 9-phenyl-9-(pyrrolidin-1-yl)-3-azaspiro[5.5]undecane (A2)

Stage 1: 1-(8-Phenyl-1,4-dioxaspiro[4.5]decan-8-yl)pyrrolidine

A mixture of 1,4-dioxaspiro[4.5]decan-8-one (10 g, 64 mmol), benzotriazole (7.62 g, 64 mmol) and pyrrolidine (5.26 ml, 64 mmol) in dry benzene (300 ml) was refluxed under an argon atmosphere in a water separator for 18 h. The reaction mixture was cooled to 25° C. and concentrated to small volume under vacuum and dried (aerated with argon). The crude product was taken up in dry tetrahydrofuran (50 ml) and cooled to 0° C. Phenyl magnesium bromide solution (650 ml, 1 mol/l in tetrahydrofuran) was added dropwise under protective gas. The cooling bath was removed and the mixture stirred for 18 h at 25° C. The reaction mixture was cooled to 0° C. again, hydrolysed with saturated ammonium chloride solution and extracted with ethyl acetate (3×300 ml). The combined organic phases were washed with saturated sodium chloride solution, dried over sodium sulfate, filtered and concentrated to small volume under vacuum. The crude product was purified by column chromatography (silica gel) with 5% methanol in dichloromethane. Yield: 13%

Stage 2: 4-Phenyl-4-(pyrrolidin-1-yl)cyclohexanone

The reaction was performed starting from 1-(8-phenyl-1,4-dioxaspiro[4.5]decan-8-yl)pyrrolidine in an analogous manner to stage 2 amine (A1). Yield: 80%

Stage 3: 2,4-Dioxo-9-phenyl-9-(pyrrolidin-1-yl)-3-azaspiro[5.5]undecane-1,5-dicarbonitrile The reaction was performed starting from 4-phenyl-4-(pyrrolidin-1-yl)cyclohexanone in an analogous manner to stage 3 amine (A1). Yield: 29%

Stage 4: 2,2'-(4-Phenyl-4-(pyrrolidin-1-yl)cyclohexane-1,1-diyl)diacetic acid

The reaction was performed starting from 2,4-dioxo-9-phenyl-9-(pyrrolidin-1-yl)-3-azaspiro[5.5]undecane-1,5-dicarbonitrile in an analogous manner to stage 4 amine (A1).

Stage 5: Diethyl 3,3'-(4-phenyl-4-(pyrrolidin-1-yl)cyclohexane-1,1-diyl)dipropanoate The reaction was performed starting from 2,2'-(4-phenyl-4-(pyrrolidin-1-yl)cyclohexane-1,1-diyl)diacetic acid in an analogous manner to stage 5 amine (A1). Yield: 53% (after 2 stages)

Stage 6: 2,2'-(4-Phenyl-4-(pyrrolidin-1-yl)cyclohexane-1,1-diyl)diethanol

The reaction was performed starting from diethyl 3,3'-(4-phenyl-4-(pyrrolidin-1-yl)cyclohexane-1,1-diyl)dipropanoate in an analogous manner to stage 6 amine (A1). Yield: quantitative Stage 7: 2,2'-(4-Phenyl-4-(pyrrolidin-1-yl)cyclohexane-1,1-diyl)bis(ethane-2,1-diyl)dimethanesulfonate The reaction was performed starting from 2,2'-(4-phenyl-4-(pyrrolidin-1-yl)cyclohexane-1,1-diyl)diethanol in an analogous manner to stage 7 amine (A1). Yield: 71%

Stage 8: 3-Allyl-9-phenyl-9-(pyrrolidin-1-yl)-3-azaspiro[5.5]undecane

The reaction was performed starting from 2,2'-(4-phenyl-4-(pyrrolidin-1-yl)cyclohexane-1,1-diyl)bis(ethane-2,1-diyl) dimethanesulfonate in an analogous manner to stage 8 amine (A1). Yield: 60%

Stage 9: 9-Phenyl-9-(pyrrolidin-1-yl)-3-azaspiro[5.5]undecane (A2)

The reaction was performed starting from 3-allyl-9-phenyl-9-(pyrrolidin-1-yl)-3-azaspiro[5.5]undecane in an analogous manner to stage 9 amine (A1). Yield: 90%

Synthesis of 9-(3-fluorophenyl)-N,N-dimethyl-3-azaspiro[5.5]undecan-9-amine (A3)

Stage 1: 8-(3-Fluorophenyl)-N,N-dimethyl-1,4-dioxaspiro[4.5]decan-8-amine

The reaction was performed starting from 1,4-dioxaspiro[4.5]decan-8-one and 4-fluorophenylmagnesium chloride (1 M in hexane) in an analogous manner to stage 1 amine (A1).

Stage 2: 4-(Dimethylamino)-4-(3-fluorophenyl)cyclohexanone

The reaction was performed starting from 8-(3-fluorophenyl)-N,N-dimethyl-1,4-dioxaspiro[4.5]decan-8-amine in an analogous manner to stage 2 amine (A1).

Stage 3: 9-(Dimethylamino)-9-(3-fluorophenyl)-2,4-dioxo-3-azaspiro[5.5]undecane-1,5-dicarbonitrile The reaction was performed starting from 4-(dimethylamino)-4-(3-fluorophenyl)cyclohexanone in an analogous manner to stage 3 amine (A1).

Stage 4: 2,2'-(4-(Dimethylamino)-4-(3-fluorophenyl)cyclohexane-1,1-diyl)diacetic acid The reaction was performed starting from 9-(dimethylamino)-9-(3-fluorophenyl)-2,4-dioxo-3-azaspiro[5.5]undecane-1,5-dicarbonitrile in an analogous manner to stage 4 amine (A1).

Stage 5: Diethyl 3,3'-(4-(dimethylamino)-4-(3-fluorophenyl)cyclohexane-1,1-diyl)dipropanoate The reaction was performed starting from 2,2'-(4-(dimethylamino)-4-(3-fluorophenyl)cyclohexane-1,1-diyl)diacetic acid in an analogous manner to stage 5 amine (A1). Yield: 30% (after 2 stages)

Stage 6: 2,2'-(4-(Dimethylamino)-4-(3-fluorophenyl)cyclohexane-1,1-diyl)diethanol The reaction was performed starting from diethyl 3,3'-(4-(dimethylamino)-4-(3-fluorophenyl)cyclohexane-1,1-diyl) dipropanoate in an analogous manner to stage 6 amine (A1). Yield: 60%

Stage 7: 2,2'-(4-(Dimethylamino)-4-(3-fluorophenyl)cyclohexane-1,1-diyl)bis(ethane-2,1-diyl)dimethanesulfonate The reaction was performed starting from 2,2'-(4-(dimethylamino)-4-(3-fluorophenyl)cyclohexane-1,1-diyl)diethanol in an analogous manner to stage 7 amine (A1). Yield: quantitative Stage 8: 3-Allyl-9-(3-fluorophenyl)-N,N-dimethyl-3-azaspiro[5.5]undecan-9-amine The reaction was performed starting from 2,2'-(4-(dimethylamino)-4-(3-fluorophenyl)cyclohexane-1,1-diyl)bis (ethane-2,1-diyl) dimethanesulfonate in an analogous manner to stage 8 amine (A1). Yield: 50%

Stage 9: 9-(3-Fluorophenyl)-N,N-dimethyl-3-azaspiro[5.5]undecan-9-amine (A3)

The reaction was performed starting from 3-allyl-9-(3-fluorophenyl)-N,N-dimethyl-3-azaspiro[5.5]undecan-9-amine in an analogous manner to stage 9 amine (A1). Yield: quantitative Synthesis of 9-(Azetidin-1-yl)-9-phenyl-3-azaspiro [5.5]undecane Trifluoroacetate (A4)

Step-1: 1-tert-Butyl 4-methyl piperidine-1,4-dicarboxylate

To a stirred solution of methyl isonipecotate (127.2 mmol, 1 eq) in dichloromethane (200 ml) were added di-tert-butyldicarbonate (190.8 mmol, 1.5 eq) and triethylamine (254.4 mmol, 2.0 eq). The reaction mixture was stirred for 12 h at 25° C. It was then diluted with dichloromethane (100 ml) and washed with water (50 ml) and brine (50 ml). The organic layer was separated, dried over $Na_2SO_4$, concentrated and employed in the next step without further purification. Yield: 98%

Step-2: tert-Butyl 4-(hydroxymethyl)piperidine-1-carboxylate

To a stirred solution of 1-tert-butyl 4-methyl piperidine-1, 4-dicarboxylate (171.3 mmol, 1 eq) in THF (250 ml) was added $LiBH_4$ (342.6 mmol, 2 eq) at 0° C. The reaction mixture was then heated at reflux for 2 h and then cooled to 0° C. Ice-water (100 g) was added and the aqueous layer was extracted with ethyl acetate (200 ml). The organic layer was washed with brine (50 ml), the layers were separated, and the organics dried over $Na_2SO_4$, concentrated and employed in the next step without further purification. Yield: 82%

Step-3: tert-Butyl 4-formylpiperidine-1-carboxylate

To the solution of tert-butyl 4-(hydroxymethyl)piperidine-1-carboxylate (139.5 mmol) in DCM (300 ml) was added PCC (209.3 mmol, 1.5 eq) at 0° C. The reaction mixture was then allowed to stir at 25° C. for 16 h. The mixture was filtered through celite, washed with DCM (2×200 ml), and the organics were concentrated and purified by silica gel column chromatography (10% EtOAc in DCM) to obtain the desired compound. Yield: 42%

Step-4: tert-Butyl 9-oxo-3-azaspiro[5.5]undec-7-ene-3-carboxylate

To the solution of tert-butyl 4-formylpiperidine-1-carboxylate (5.87 mmol, 1 eq) in THF (250 ml) was added methyl vinyl ketone (7.63 mmol, 1.3 eq) at 0° C., followed by slow addition of 3 N KOH in ethanol (7.7 ml). The reaction was then stirred at 25° C. for 16 h. The reaction mixture was concentrated to one-third of the volume of solvent and then acidified with 0.5 N HCl at 0° C. The aqueous layer was extracted with ethyl acetate (2×100 ml), and the organics dried over $Na_2SO_4$ and concentrated. The crude material was used in the next step without further purification. Yield: 91%

Step-5: tert-Butyl 9-oxo-3-azaspiro[5.5]undecane-3-carboxylate tert-Butyl 9-oxo-3-azaspiro[5.5]undec-7-ene-3-carboxylate (6.41 mmol, 1 eq) was taken up in ethanol (500 ml) and to the mixture was added 10% Pd/C (3.4 g). The mixture was hydrogenated at 25° C. for 16 h. The reaction mixture was filtered through celite, concentrated and purified by silica gel column chromatography to yield the desired product. Yield: 38%

Step-6: tert-Butyl 9-(azetidin-1-yl)-9-phenyl-3-azaspiro[5.5]undecane-3-carboxylate Azetidine (29.9 mmol, 10 eq) was added to a solution of tert-butyl 9-oxo-3-azaspiro[5.5]undecane-3-carboxylate (2.99 mmol, 1 eq) in methanol (15 ml) and acetic acid (1.5 ml) at 0° C. Then potassium cyanide (7.47 mmol, 2.5 eq) was added to the reaction mixture and it was stirred for another 16 h. The reaction mixture was slowly quenched with $NH_4OH$ solution (50 g ice+50 ml ammonia liquor) and stirred at 0° C. for another 30 min. The mixture was extracted with ethyl acetate. The organic layer was washed with water (15 ml), saturated ferrous sulfate solution (15 ml) and brine (20 ml) successively, dried over $Na_2SO_4$ and concentrated under reduced pressure to give the crude product. A solution of the crude product (1.1 g) in THF (30 ml) was added to an ice-cold solution of phenyl magnesium bromide (5 eq., 1 M solution in THF) and the resulting reaction mixture was stirred at 25° C. for 16 h under a nitrogen atmosphere. The reaction mixture was quenched with saturated ammonia solution under ice-cold conditions and extracted with ethyl acetate. The organic layer was washed with water (10 ml) and brine (10 ml), dried over anhydrous sodium sulfate and concentrated under reduced pressure to give the crude product. The crude product was purified by silica gel column chromatography (25% EtOH in hexanes) to yield the desired product. Yield: 22%

Step-7: 9-(Azetidin-1-yl)-9-phenyl-3-azaspiro[5.5]undecane Trifluoroacetate (A4)

To a stirred solution of tert-butyl 9-(azetidin-1-yl)-9-phenyl-3-azaspiro[5.5]-undecane-3-carboxylate (0.65 mmol, 1 eq) in dichloromethane (3 ml) was added TFA (2 ml) at 0° C. and the reaction mixture was stirred at 23° C. for h. The reaction was then concentrated to obtain the crude product as its corresponding TFA salt, which was employed in the next step without purification.

Synthesis of 9-(3,3-Difluoroazetidin-1-yl)-9-phenyl-3-azaspiro[5.5]undecane (A5)

Step-1: 9-Benzyl-2,4-dioxo-3,9-diazaspiro[5.5]undecane-1,5-dicarbonitrile

To a mixture of 1-benzylpiperidin-4-one (20 g, 0.105 mol) and cyano-acetic acid ethyl ester (23.9 g, 0.21 mol) was added saturated $NH_3$-ethanol solution at −10° C. and the mixture was stirred for 1 h maintaining the same temperature. The reaction mixture was stored in the refrigerator for 2 d. To the solid product, which had formed, was added DCM and the mixture was then filtered through a sintered funnel and the solid washed with DCM repeatedly. The white solid was dried under reduced pressure to give the desired product which was used in the next step without further purification. Yield: 73%

Step-2: Diethyl 2,2'-(1-benzylpiperidine-4,4-diyl)diacetate

To 9-benzyl-2,4-dioxo-3,9-diazaspiro[5.5]undecane-1,5-dicarbonitrile (25 g, 77.63 mmol) was added 65% $H_2SO_4$ and the resulting mixture was refluxed for 2 h. The reaction mixture was cooled to room temperature and water (35 ml) was added. Again the reaction mixture was refluxed, this time overnight. Then it was cooled to 5-10° C. and basified with 40% NaOH solution to pH~10. It was again acidified with 2 N HCl and the solvent part was removed form reaction mixture under reduced pressure. The residual part was co-distilled with benzene using a Dean-Stark apparatus. Benzene was then removed under reduced pressure and concentrated sulfuric acid was added. The mixture was then refluxed overnight. The reaction mixture was cooled to room temperature and filtered through a sintered funnel. The filtrate was concentrated and water (50 ml) was added. It was basified to pH~7-8 with solid $Na_2CO_3$ and then the organic part was extracted with ethyl acetate. The organic layer was dried over $Na_2SO_4$, concentrated and purified by column chromatography to yield desire product. Yield: 55%

Step 3: 2,2'-(1-Benzylpiperidine-4,4-diyl)diethanol

To a slurry of LAH (656 mg, 17.3 mmol, 3.0 eq) in THF (50 ml) was added dropwise diethyl 2,2'-(1-benzylpiperidine-4,4-diyl)diacetate (2 g, 5.76 mmol) in THF (10 ml) at 0° C. The reaction mixture was stirred at room temperature overnight. The reaction was quenched with THF/water (0.7 ml water in 7 ml THF). Then the mixture was stirred for 1 h at room temperature, filtered through celite and concentrated to dryness to yield the desired compound. The crude product was used directly in next step without further purification. Yield: 80%

Step 4: tert-Butyl 4,4-bis(2-hydroxyethyl)piperidine-1-carboxylate

To a solution of 2,2'-(1-benzylpiperidine-4,4-diyl)diethanol (1.8 g, 6.844 mmol) was added (Boc)$_2$O (1.93 g, 8.89 mmol) and Pd/C (600 mg). The mixture was hydrogenated under Parr shaker at 50 psi overnight. TLC revealed complete conversion and the reaction mixture was filtered though celite and washed with methanol. The filtrate was concentrated and purified by column chromatography (silica (100-200), MeOH/DCM (6%)) to yield the desired product. Yield: 81%

Step-5: tert-Butyl 4,4-bis(2-(methylsulfonyloxy)ethyl)piperidine-1-carboxylate To a stirred solution of tert-butyl 4,4-bis(2-hydroxyethyl)piperidine-1-carboxylate (500 mg, 1.83 mmol) in DCM (10 ml) were added mesyl chloride (0.33 ml, 4.2 mmol) and TEA (1 ml, 7.32 mmol) at −20° C. and the mixture was stirred for 30 min maintaining the same temperature. TLC revealed completion of the reaction and it was quenched with water and extracted with DCM. The organic phase was washed with brine, dried over $Na_2SO_4$ and concentrated to dryness. The crude product was purified by column chromatography (silica (100-200), EtOAc-hexane (30%)) to yield the desired compound. Yield: 70%

Step-6: tert-Butyl 4,4-bis(2-cyanoethyl)piperidine-1-carboxylate tert-Butyl 4,4-bis(2-(methylsulfonyloxy)ethyl)piperidine-1-carboxylate (550 mg, 1.282 mmol) was dissolved in ethanol-water (6 ml, 9:1) and KCN (183.3 mg, 2.82 mmol) was added at room temperature. The reaction mixture was heated to 60° C. overnight. TLC revealed complete consumption of the starting material and the reaction mixture was diluted with ethyl acetate and washed with brine. It was then given FeSO$_4$ solution wash and finally the organic layer was washed with brine. The organics were dried over $Na_2SO_4$, concentrated to dryness and the crude product was purified by column chromatography (silica gel (100-200), ethyl acetate-hexane (30%)) to obtain the desired product. Yield: 46%

Step-7: 3,3'-(Piperidine-4,4-diyl)dipropanoic acid Hydrochloride

To tert-butyl 4,4-bis(2-cyanoethyl)piperidine-1-carboxylate (130 mg, 0.446 mmol) was added HCl—H$_2$O (1 ml, 1:1) at 0° C. and the reaction mixture was refluxed overnight. After completion of the reaction (monitored by LCMS), the solvent was evaporated to dryness. The crude product was azeotroped with toluene (2-3×) and then used directly in the next step.

Step-8: Dimethyl 3,3'-(piperidine-4,4-diyl)dipropanoate Hydrochloride

To the solution of 3,3'-(piperidine-4,4-diyl)dipropanoic acid hydrochloride (0.446 mmol) in MeOH (2 ml) was added dropwise SOCl$_2$ (0.18 ml, 3.0 eq) at 0° C. The reaction mixture was then refluxed overnight. Monitoring by LCMS revealed complete consumption of the starting material and the solvent was concentrated to dryness. The crude product was azeotroped with toluene and then used directly in next step.

Step-9: Dimethyl 3,3'-(1-(tert-butoxycarbonyl)piperidine-4,4-diyl)dipropanoate The a stirred solution of dimethyl 3,3'-(piperidine-4,4-diyl)dipropanoate hydrochloride (0.44 mmol, 1.0 eq) in DCM (2 ml) were added TEA (6.0 eq) and (Boc)$_2$O (1.5 eq) at 0° C. The mixture was then stirred at room temperature overnight. The reaction mixture was diluted with DCM and washed with water and brine. The organic layer was dried over $Na_2SO_4$, concentrated to dryness and purified by column chromatography. Yield: 40%

Step-10: 3-tert-Butyl 8-methyl 9-oxo-3-azaspiro[5.5]undecane-3,8-dicarboxylate Dimethyl 3,3'-(1-(tert-butoxycarbonyl)piperidine-4,4-diyl)dipropanoate (600 mg, 1.68 mmol) was dissolved in dry THF (10 ml) and a solution of t-BuOK (417 mg, 3.6 mmol) in THF was added at ice cold reaction conditions. The reaction mixture was stirred at room temperature for 2 h. TLC revealed completion of the reaction. The solvent was evaporated to dryness, the residue diluted with ethyl acetate and washed with water and brine. The organic layer was dried over $Na_2SO_4$, concentrated to dryness and purified by column chromatography to obtain the desired compound. Yield: 78%

Step-11: 3-Azaspiro[5.5]undecan-9-one Hydrochloride

To 3-tert-butyl 8-methyl 9-oxo-3-azaspiro[5.5]undecane-3,8-dicarboxylate (450 mg, 1.38 mmol) was added HCl—H$_2$O (5 ml, 1:1) at 0° C. and the mixture was refluxed overnight. LCMS revealed complete consumption of the starting material and the mixture was concentrated to dryness. The crude product thus obtained was used directly in next step.

Step-12: tert-Butyl 9-oxo-3-azaspiro[5.5]undecane-3-carboxylate

The crude 3-azaspiro[5.5]undecan-9-one hydrochloride was dissolved in DCM (5 ml). TEA (3.45 mmol, 2.5 eq) and (Boc)$_2$O (0.4 ml, 2.07 mmol, 1.5 eq) were added to the solution and the resulting mixture was stirred at room temperature overnight. The reaction mixture was diluted with DCM and washed with water and brine. The organic layer was dried over $Na_2SO_4$, concentrated to dryness and the crude product was purified by column chromatography to give the desired compound. Yield: 73%

Step-13: tert-Butyl 9-cyano-9-(3,3-difluoroazetidin-1-yl)-3-azaspiro[5.5]undecane-3-carboxylate To a solution of tert-butyl 9-oxo-3-azaspiro[5.5]undecane-3-carboxylate (600 mg, 2.247 mmol) in MeOH:H$_2$O (25 ml, 9:1) was added AcOH (2.5 ml) and 3,3-difluorozetidine hydrochloride (2.1 g, 16.8 mmol) followed by KCN (436 mg, 6.72 mmol) The reaction mixture was then stirred at room temperature overnight. The mixture was quenched with 50% NH₃ solution in ice cold water. The aqueous layer was extracted with ethyl acetate and the organic layer was washed with water several times. The organic layer was given FeSO₄ solution wash and finally a brine wash. The organic phase was dried over Na₂SO₄, concentrated to dryness and the crude product obtained directly carried through to the next step.

Step-14: tert-Butyl 9-(3,3-difluoroazetidin-1-yl)-9-phenyl-3-azaspiro[5.5]undecane-3-carboxylate The crude tert-butyl 9-cyano-9-(3,3-difluoroazetidin-1-yl)-3-azaspiro[5.5]-undecane-3-carboxylate was taken up in THF (20 ml) and PhMgBr (12 ml) was added at 0° C. The reaction mixture was stirred at room temperature overnight. The mixture was quenched with NH₄Cl solution at 0° C. and was then extracted with ethyl acetate. The organic layer was washed with brine, dried over Na₂SO₄, concentrated and purified by column chromatography (silica gel (100-200)) to obtain the desired compound. Yield: 31%

Step-15: 9-(3,3-Difluoroazetidin-1-yl)-9-phenyl-3-azaspiro[5.5]undecane (A5)

tert-Butyl 9-(3,3-difluoroazetidin-1-yl)-9-phenyl-3-azaspiro[5.5]undecane-3-carboxylate (300 mg, 0.714 mmol) was taken up in DCM (24 ml) and TFA (6 ml) was added. The resulting mixture was stirred for 3 h. The TLC revealed completion of the reaction and the solvent was removed under reduced pressure. The compound was azeotroped (2-3x) with DCM and used in the next step.

3.) Synthesis of Example Compounds Having the General Formula (I)

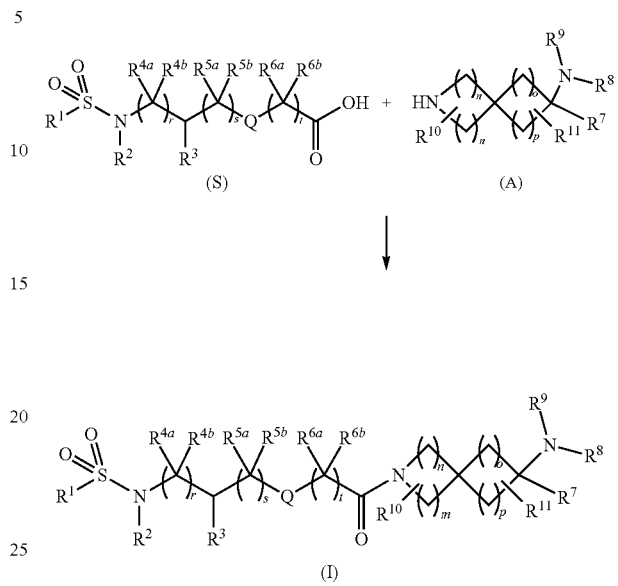

General Procedure:

Diisopropylethylamine (2.5 eq) was added to a solution of the acid structural unit (S) (1. Eq.) in dichloromethane (10 ml/mmol) at 0° C., followed by the addition of HOBT (1 eq) and EDCI (1.5 eq). The cooling bath was removed, the solution stirred for 15 min at 25° C., then cooled to 0° C. again and amine structural unit (A) (1.2 eq) was added. The reaction mixture was stirred for 16 h at 25° C., then diluted with dichloromethane (30 ml) and washed with saturated ammonium chloride solution, saturated sodium chloride solution, saturated sodium carbonate solution and once more with saturated sodium chloride solution. The organic phase was dried over sodium sulfate and concentrated to small volume under vacuum. The crude product was purified by column chromatography, primarily with 1% methanol in dichloromethane over Alox neutral.

The following table shows the amine and acid structural units used for the preparation of example compounds given below.

| Example | Acid structural unit (S) | Amine structural unit (A) | Yield | Analysis (LC/MS) |
|---|---|---|---|---|
| 1 | 2-((1-(4-Methoxy-2,6-dimethyl-phenyl-sulfonyl)piperidin-2-yl)methoxy)acetic acid (S1) | 9-Phenyl-9-(pyrrolidin-1-yl)-3-azaspiro[5.5]undecane (A2) | 18% | $R_t$ = 3.8 min; m/z = 652.4 $[MH]^+$ |

-continued

| Example | Acid structural unit (S) | | Amine structural unit (A) | | Yield | Analysis (LC/MS) |
|---|---|---|---|---|---|---|
| 2 | (S)-2-((1-(4-Methoxy-2,6-dimethyl-phenyl-sulfonyl)piperidin-2-yl)methoxy)acetic acid (S2) | | N,N-Dimethyl-9-phenyl-3-azaspiro[5.5]undecan-9-amine (A1) | | 20% | R$_t$ = 3.7 min; m/z = 626.4 [MH]$^+$ |
| 3 | 2-(2-(N-Cyclopropyl-4-methoxy-2,6-dimethyl-phenyl-sulfonamido)ethoxy)acetic acid (S3) | | N,N-Dimethyl-9-phenyl-3-azaspiro[5.5]undecan-9-amine (A1) | | 15% | R$_t$ = 3.6 min; m/z = 612.5 [MH]$^+$ |
| 4 | (S)-2-((1-(4-Methoxy-2,6-dimethyl-phenyl-sulfonyl)indolin-2-yl)methoxy)acetic acid (S4) | | N,N-Dimethyl-9-phenyl-3-azaspiro[5.5]undecan-9-amine (A1) | | 20% | R$_t$ = 3.9 min; m/z = 660.5 [MH]$^+$ |
| 5 | (3R)-(Naphthalene-2-sulfonamido)-3-phenyl-propionic acid (S5) | | N,N-Dimethyl-9-phenyl-3-azaspiro[5.5]undecan-9-amine (A1) | | 15% | R$_t$ = 3.7 min; m/z = 610.5 [MH]$^+$ |
| 6 | (S)-2-((1-(2-Chloro-6-methyl-phenyl-sulfonyl)piperidin-2-yl)methoxy)acetic acid (S6) | | N,N-Dimethyl-9-phenyl-3-azaspiro[5.5]undecan-9-amine (A1) | | 18% | R$_t$ = 3.7 min; m/z = 616.4 [MH]$^+$ |

-continued

| Example | Acid structural unit (S) | | Amine structural unit (A) | | Yield | Analysis (LC/MS) |
|---|---|---|---|---|---|---|
| 7 | 3-(1-(4-Chloro-2,5-dimethyl-phenyl-sulfonyl)piperidin-2-yl)propionic acid (S7) | | N,N-Dimethyl-9-phenyl-3-azaspiro[5.5]undecan-9-amine (A1) | | 15% | $R_t$ = 4.0 min; m/z = 614.5 [MH]$^+$ |
| 8 | 4-(1-(4-Methoxy-2,6-dimethyl-phenyl-sulfonyl)piperidin-2-yl)butanoic acid (S8) | | N,N-Dimethyl-9-phenyl-3-azaspiro[5.5]undecan-9-amine (A1) | | 7% | $R_t$ = 3.9 min; m/z = 624.6 [MH]$^+$ |
| 9 | 2-(1-(3-(Trifluoromethyl)phenyl-sulfonyl)piperidin-2-yl)acetic acid (S9) | | N,N-Dimethyl-9-phenyl-3-azaspiro[5.5]undecan-9-amine (A1) | | 10% | $R_t$ = 3.7 min; m/z = 606.5 [MH]$^+$ |
| 10 | (R)-2-(1-(4-Methoxy-2,6-dimethyl-phenyl-sulfonyl)-3-oxo-1,2,3,4-tetrahydro-pyrazin-2-yl)acetic acid (S10) | | N,N-Dimethyl-9-phenyl-3-azaspiro[55]undecan-9-amine (A1) | | | $R_t$ = 3.2 min; m/z = 609.5 [MH]$^+$ |
| 11 | (S)-2-((1-(4-Methoxy-2,6-dimethyl-phenyl-sulfonyl)piperidin-2-yl)methoxy)acetic acid (S2) | | 9-(3-Fluorophenyl)-N,N-dimethyl-3-azaspiro[5.5]undecan-9-amine (A3) | | 27% | $R_t$ = 4.0 min; m/z = 644.5 [MH]$^+$ |

| Example | Acid structural unit (S) | Amine structural unit (A) | Yield | Analysis (LC/MS) |
|---|---|---|---|---|
| 12* | (S)-2-((1-(4-Methoxy-2,6-dimethyl-phenyl-sulfonyl)piperidin-2-yl)methoxy)acetic acid (S2) | 9-(Azetidin-1-yl)-9-phenyl-3-azaspiro[5.5]undecane Trifluoroacetate (A4) | 31% | $R_t$ = 3.8 min; m/z = 638.5 [MH]$^+$ |
| 13** | (S)-2-((1-(4-Methoxy-2,6-dimethyl-phenyl-sulfonyl)piperidin-2-yl)methoxy)acetic acid (S2) | 9-(3,3-Difluoroazetidin-1-yl)-9-phenyl-3-azaspiro[5.5]undecane (A5) | 31% | $R_t$ = 4.8 min; m/z = 674.4 [MH]$^+$ |

*The Synthesis of Example 12 Did not Follow the Described General Procedure:

To a stirred solution of acid structural unit (S2) (0.65 mmol, 1 eq) in THF (5 ml) was added HATU (0.716 mmol, 1.1 eq) and the reaction mixture was cooled to 0° C. DIPEA (1.6 mmol, 2.5 eq) was added to the mixture and it was stirred for 10 min. A solution of amine structural unit (A4) in THF (3 ml) was added dropwise and the reaction mixture was stirred for 16 h. Water (10 ml) was added to the mixture and it extracted with DCM (3×25 ml). The combined organic layers were washed with water (25 ml) and brine (25 ml), and were then dried over sodium sulfate. Upon concentration in vacuo the crude compound was obtained and subsequently purified by column chromatography (5% DCM in MeOH) to obtain the desired compound.

**The Synthesis of Example 13 Did not Follow the Described General Procedure:

To a cooled (0° C.) solution of acid structural unit (S2) (265 mg, 0.714 mmol, 1.0 eq) in THF (5 ml) were added DIPEA (4 eq) and HATU (1.5 eq) and the resulting mixture was stirred at room temperature for 15 min. It was again cooled to 0° C. and a solution of amine structural unit (A5) (0.714 mmol, 1.0 eq) in THF (2 ml) was added and the mixture stirred at room temperature overnight. The reaction mixture was concentrated to dryness, diluted with ethyl acetate and washed with $Na_2CO_3$ solution, water and brine. The organic layer was dried over $Na_2SO_4$, concentrated and purified by column chromatography (silica gel (100-200)) to yield the desired compound.

B) Library Compound Syntheses

In the library compound synthesis acid structural unit (S) are referred to as acid building blocks ACI-CC and amine structural units (A) are referred to as amine building blocks AMN-CC.

1) Synthesis of the Amine Building Blocks

Overview:

| AMN-CC building block no. | Structure | AMN-CC Name |
|---|---|---|
| AMN-CC-01 | 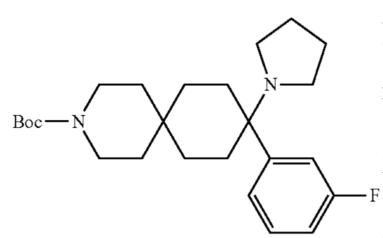 | tert-Butyl 9-(3-fluoro-phenyl)-9-(pyrrolidin-1-yl)-3-azaspiro[5.5]undecane-3-Fcarboxylate (AMN-CC-01) |
| AMN-CC-02 | 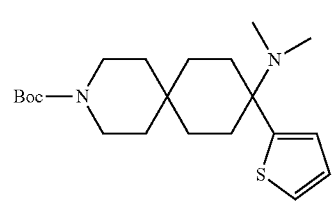 | tert-Butyl 9-(dimethyl-amino)-9-(thiophen-2-yl)-3-aza-spiro[5.5]undecane-3-carboxylate (AMN-CC-02) |

Synthesis of amine AMN-CC-01: tert-Butyl 9-(3-fluorophenyl)-9-(pyrrolidin-1-yl)-3-azaspiro[5.5]undecane-3-carboxylate (AMN-CC-01)

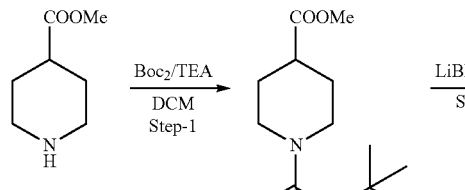

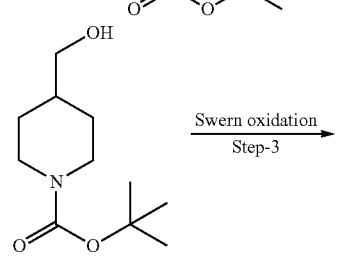

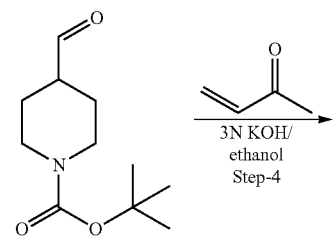

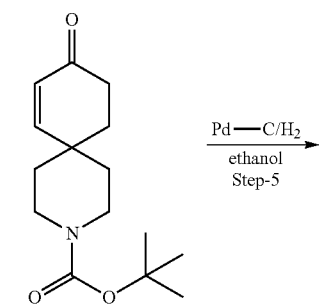

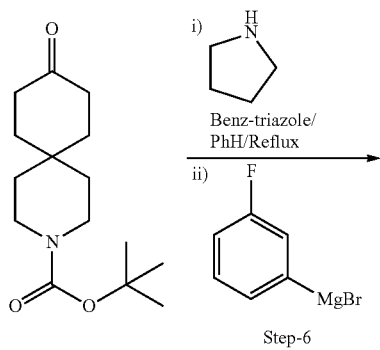

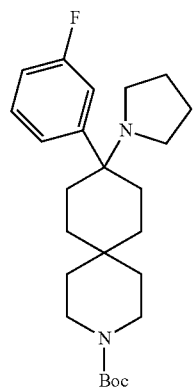

Step 1: To a stirred solution of methyl piperidine-4-carboxylate (20 g, 127.2 mmol) in dichloromethane (200 ml), boc-anhydride (41.6 ml, 190.8 mmol) and triethylamine (35.3 ml, 254.4 mmol) was added and stirred for 12 h at room temperature. The reaction mixture was diluted with dichloromethane and washed with water and brine. The organic layer was separated out, dried over $Na_2SO_4$, concentrated and used for next step without further any purification. Yield: 98%

Step 2: To the solution of step 1 product (44 g, 171.3 mmol) in THF (250 ml) was added $LiBH_4$ (7.4 g, 342.4 mmol) at 0° C. The reaction mixture was then refluxed for 2 h. The reaction mixture was cooled to 0° C. and ice water was added. The aqueous layer was then extracted using ethyl acetate and was finally given a brine wash. The organic layer was separated out, dried over $Na_2SO_4$, concentrated and used for next step without further any purification. Yield: 82%.

Step 3: To the solution of step 2 product (30 g, 139.5 mmol) in dichloromethane (300 ml) was added PCC (45 g, 209.3 mmol) at 0° C. The reaction mixture was stirred at room temperature overnight. The reaction mixture was filtered through cilite bed and washed with dichloromethane. The organic layer was concentrated and purified by silica gel column chromatography. Yield: 42%

Step 4: To the solution of step 3 product (12.5 g, 5.8 mmol) in THF (250 ml) was added methyl vinyl ketone (6.2 ml, 7.6 mmol) at 0° C., followed by the slow addition of 3N KOH in ethanol (7.7 ml). The reaction was then allowed to stir at room temperature overnight. TLC revealed the complete consumption of starting material. The reaction mixture was concentrated to one-third of the volume of solvent and was acidified with 0.5N HCl at 0° C. The aqueous layer was extracted using ethyl acetate. The organic layer was dried over $Na_2SO_4$ and concentrated. The crude material was used for next step without any further purification. Yield: 91%.

Step 5: To the step 4 product (12.5 g, 6.4 mmol) in ethanol (500 ml) and was added 10% Pd/C (3.4 g). The mixture was hydrogenated at room temperature overnight. The reaction mixture was filtered through a cilite bed, concentrated and purified using silica gel column chromatography. Yield: 38%

Step-6: A mixture of step 5 product (5.69 g, 20.9 mmol), benzotriazole (2.49 g, 20.9 mmol) and pyrrolidine (1.75 ml, 20.9 mmol) in anhydrous benzene (140 ml) was heated to reflux for 18 h under argon atmosphere and dean-stark conditions. The reaction mixture was brought to 25° C. and concentrated to dryness under reduced pressure and argon atmosphere. The crude material was dissolved in dry THF (100 ml) and cooled to 0° C. A 0.5M solution of 3-fluorophenyl magnesium bromide in THF (168 ml) was added drop wise under argon atmosphere. The reaction was slowly brought to 25° C. and allowed to stir for 18 h. The reaction mixture was again cooled to 0° C., quenched with sat. ammonium chloride solution and extracted with ethyl acetate (3×300 ml). The combined organic layers were washed with brine, dried over sodium sulphate, filtered and concentrated under reduced pressure. The crude material was purified by column chromatography (100-200 mesh silica gel, 5% methanol in dichloromethane) to obtain the desired product. Yield: 4.5%

Synthesis of amine AMN-CC-02: tert-Butyl 9-(dimethylamino)-9-(thiophen-2-yl)-3-azaspiro[5.5]undecane-3-carboxylate (AMN-CC-02)

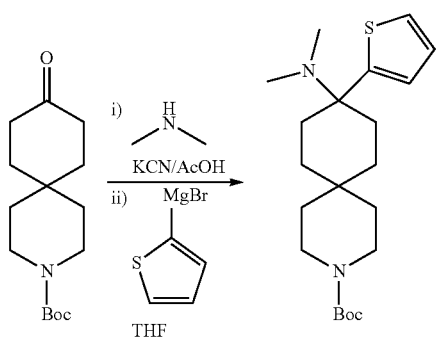

Step 1: Dimethylamine (40% aq. solution, 6 ml, 10 eq.) was, at 0° C., added to a solution of spiro-ketone (1 g, 3.7 mmol) in methanol (3 ml) and acetic acid (1 ml). Then potassium cyanide (2. eq.) was added to the reaction mixture through a solid addition funnel and stirred for 16 h. The reaction mixture was slowly quenched with $NH_4OH$ solution (50 g ice+50 ml ammonia) and stirred at 0° C. for 30 min. The reaction mixture was extracted with ethylacetate. The organic layer was washed with water, sat. $FeSO_4$ and brine. Dried over anh. sodium sulfate and concentrated under reduced pressure to give the crude intermediate. A solution of this crude intermediate (1.1 g, crude) in THF (5 ml) was added to an ice-cold solution of thiophene-2-magnesium bromide (5 eq., freshly prepared from 2-bromothiophene, Mg and catalytic amount of $I_2$ in 37 ml THF) and the reaction mixture was stirred at it for 16 h under nitrogen atmosphere. The reaction mixture was quenched with sat. ammonia under ice-cold conditions and extracted with ethylacetate. The organic layer was washed with water and brine, dried over anh. sodium sulfate and concentrated under reduced pressure to give the crude product. The crude product was purified by silica gel column chromatography (EtOH/Hexane) to give the desired product. Yield: 18%

2) Synthesis of the Acid Building Blocks

Overview:

| ACI-CC building block no. | Structure | ACI-CC Name |
|---|---|---|
| ACI-CC-01 | 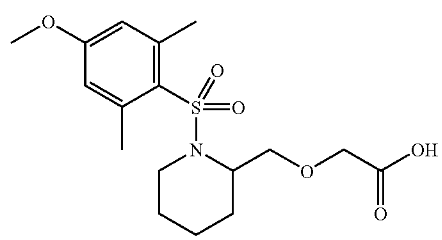 | 2-[[1-[(4-Methoxy-2,6-dimethylphenyl)sulfonyl]-piperidin-2-yl]-methoxy]-acetic acid (ACI-CC-01) |
| ACI-CC-02 | 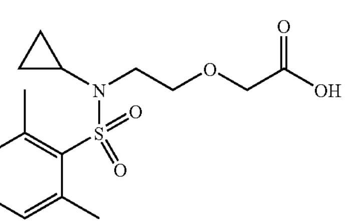 | 2-[2-[Cyclopropyl-[(4-methoxy-2,6-dimethyl-phenyl)sulfonyl]-amino]-ethoxy] -acetic acid (ACI-CC-02) |
| ACI-CC-03 | 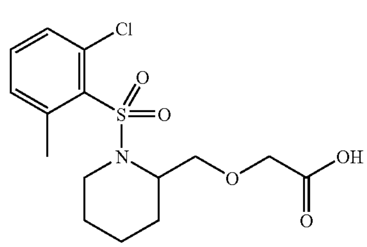 | 2-[[1-[(2-Chloro-6-methylphenyl)sulfonyl]-piperidin-2-yl]-methoxy]-acetic acid (ACI-CC-03) |

-continued

| ACI-CC building block no. | Structure | ACI-CC Name |
|---|---|---|
| ACI-CC-04 | 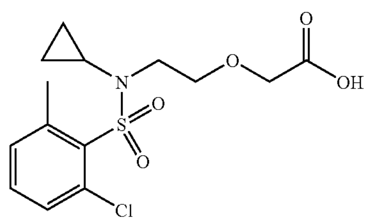 | 2-[2-[[(2-Chloro-6-methyl-phenyl)sulfonyl]-cyclopropyl-amino]-ethoxy]-acetic acid (ACI-CC-04) |
| ACI-CC-05 | 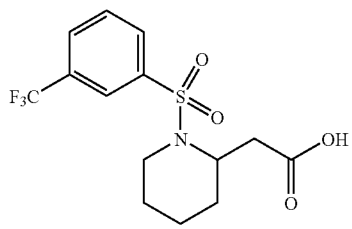 | 2-[1-[[ 3-(Trifluoromethyl)phenyl]sulfonyl] -piperidin-2-yl]-acetic acid (ACI-CC-05) |
| ACI-CC-06 | 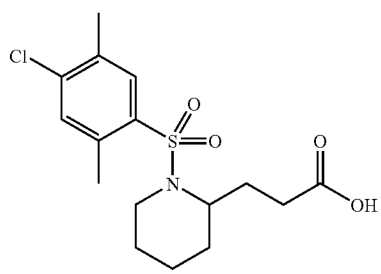 | 3-[1-[ (4-Chloro-2,5-dimethyl-phenyl)sulfonyl]-piperidin-2-yl]-propionic acid (ACI-CC-06) |
| ACI-CC-07 | 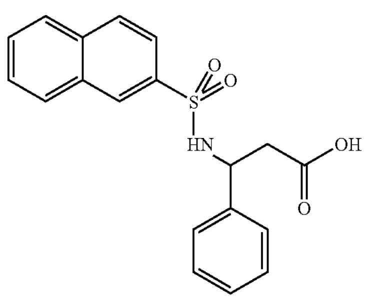 | 3-[(Naphthalen-2-ylsulfonyl)amino]-3-phenyl-propionic acid (ACI-CC-07) |
| ACI-CC-08 | 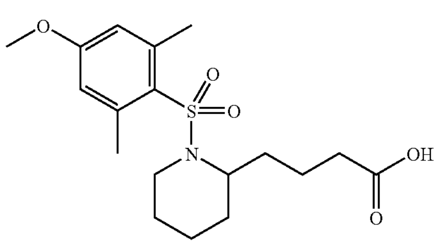 | 4-[1-[(4-Methoxy-2,6-dimethyl-phenyl)sulfonyl]-piperidin-2-yl]-butyric acid (ACI-CC-08) |

Synthesis of acid ACI-CC-01: 2-((1-(4-Methoxy-2,6-dimethylphenylsulfonyl)piperidin-2-yl)methoxy) acetic acid (ACI-CC-01)

Parallel synthesis acid building block ACI-CC-01 is identical to acid structural unit (S1) employed in single compound syntheses.

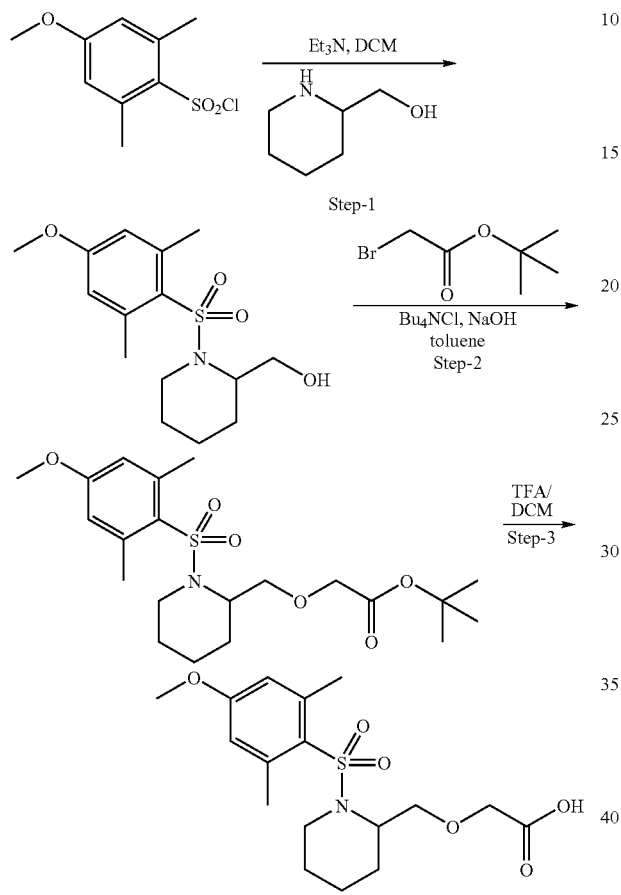

Step-1: To a cold (0° C.) solution of 2-piperidine methanol (40 mmol, 1.1 eq.) in dichloromethane (160 ml) and triethylamine (2.5 eq.), a solution of 4-methoxy-2,6-dimethylbenzenesulfonyl chloride (1 eq.) in dichloromethane (65 ml) was added drop wise maintaining temperature at 0° C. After complete addition, reaction mixture was stirred at rt for 90 mins by which time reaction was completed (TLC). 75 ml of 0.5M HCl was added into the reaction mixture and stirred for 15 mins. The organic layer was separated, washed with water, dried over sodium sulfate and evaporated to dryness to obtain the pure product. Yield: 90%

Step-2: To a cold solution of the above-prepared sulfonamide (17.16 mmol) in toluene (100 ml) was added tetrabutylammonium chloride (0.33 eq.) and 35% sodium hydroxide solution (100 ml) at 0° C. To this cold reaction mixture, tert-butyl bromoacetate (1.5 eq.) was added drop wise maintaining same temperature. After complete addition, reaction mixture was stirred at it for 90 mins by which time reaction was completed (TLC). Organic layer was then separated, washed with water until neutral pH, dried over sodium sulfate and evaporated to dryness to get the pure product. Yield: 90%

Step-3: To a dichloromethane solution (10 ml/mmol) of the required tert-butyl ester (1 eq) was added TFA (13 eq) at 0° C. and the resulting reaction mixture was stirred at ambient temperature for 2 h. Solvent was evaporated off and dried under vacuum to remove traces of TFA. The crude acid was used directly in the library synthesis without any further purification.

Synthesis of acid ACI-CC-02: 2-(2-(N-Cyclopropyl-4-methoxy-2,6-dimethylphenylsulfonamido)ethoxy) acetic acid (ACI-CC-02)

Parallel synthesis acid building block ACI-CC-02 is identical to acid structural unit (S2) employed in single compound syntheses.

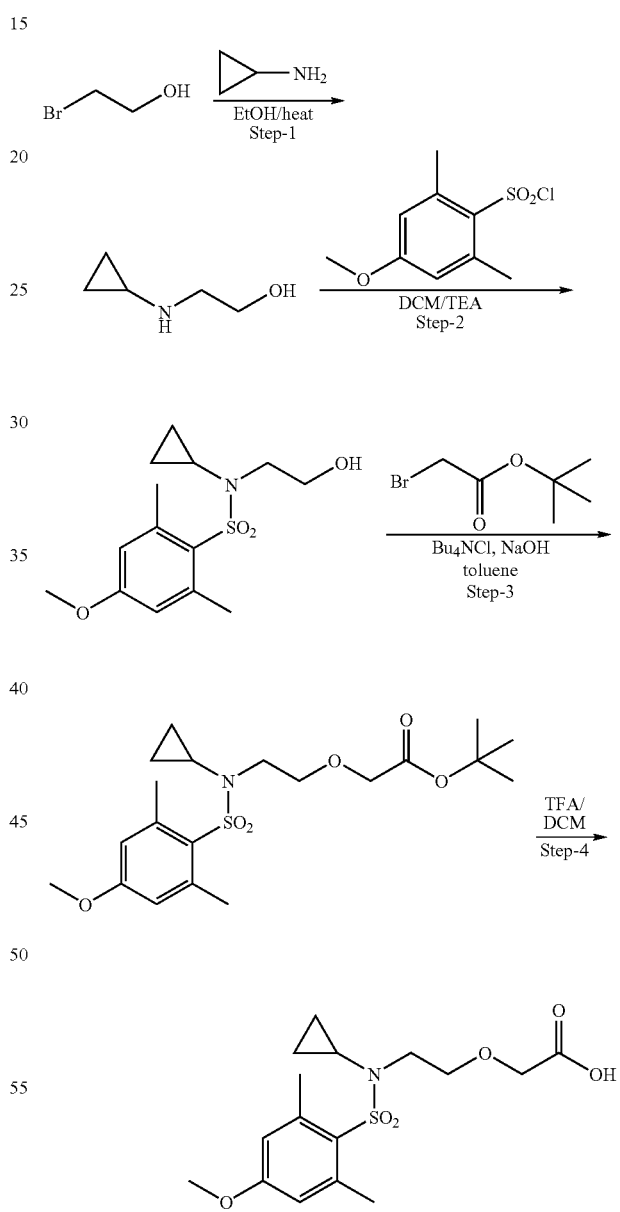

Step-1: Cyclopropyl amine (5 g, 1 eq.) was taken in ethanol (60 ml) and to it was added 2-bromo ethanol (0.5 eq.). The resulting reaction mixture was heated at 60° C. for 16 h. Reaction mixture was evaporated under reduced pressure and used directly in the next step without any further purification. Yield: 70%

Step-2, step-3 and step-4: The synthesis of ACI-CC-02 was conducted in analogy to the previously described synthesis of ACI-CC-01 (step-2, step-3 & step-4).

Synthesis of acid ACI-CC-03: 2-((1-(2-Chloro-6-methylphenylsulfonyl)piperidin-2-yl)methoxy)acetic acid (ACI-CC-03)

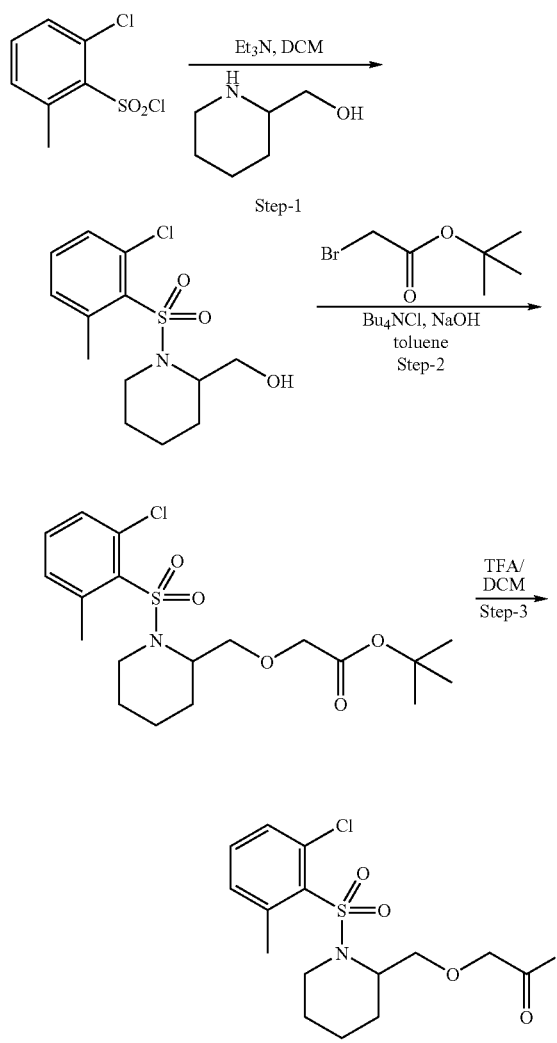

The synthesis of ACI-CC-03 was conducted in analogy to the previously described synthesis of ACI-CC-01 (step-1, step-2 & step-3).

Synthesis of acid ACI-CC-04: 2-(2-(2-Chloro-N-cyclopropyl-6-methylphenylsulfonamido)ethoxy)acetic acid (ACI-CC-04)

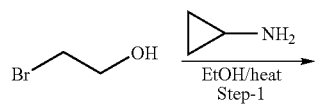

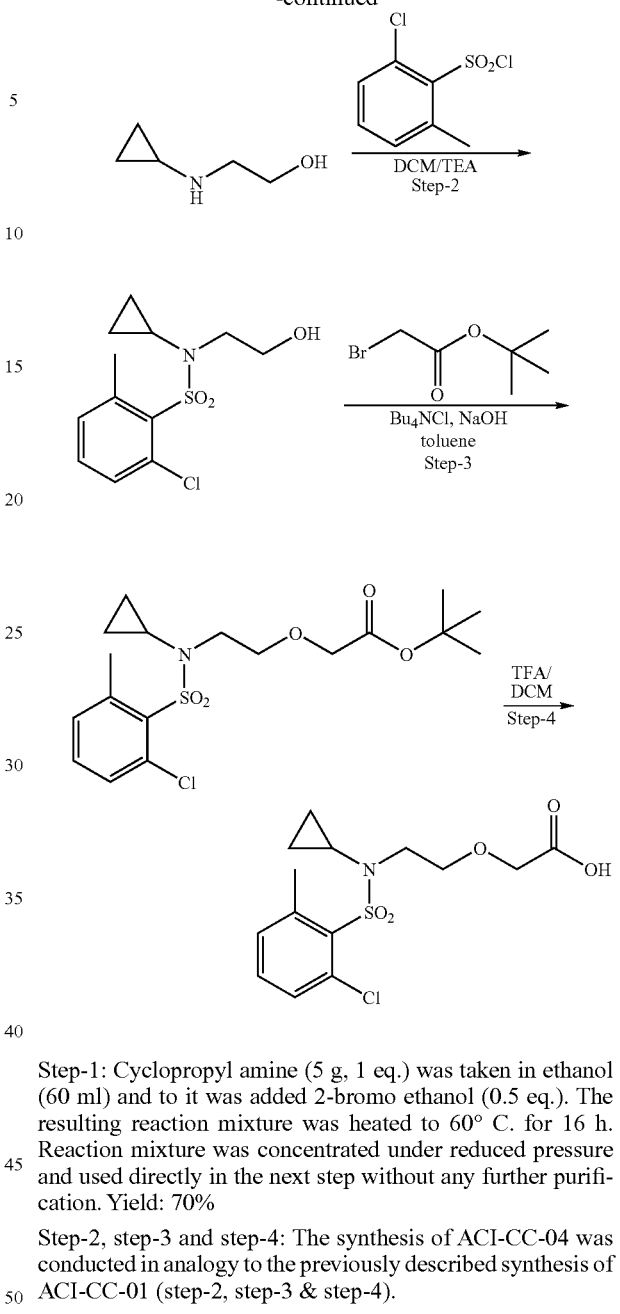

Step-1: Cyclopropyl amine (5 g, 1 eq.) was taken in ethanol (60 ml) and to it was added 2-bromo ethanol (0.5 eq.). The resulting reaction mixture was heated to 60° C. for 16 h. Reaction mixture was concentrated under reduced pressure and used directly in the next step without any further purification. Yield: 70%

Step-2, step-3 and step-4: The synthesis of ACI-CC-04 was conducted in analogy to the previously described synthesis of ACI-CC-01 (step-2, step-3 & step-4).

Synthesis of acid ACI-CC-05: 2-(1-(3-(Trifluoromethyl)-phenylsulfonyl)piperidin-2-yl)acetic acid (ACI-CC-05)

Parallel synthesis acid building block ACI-CC-05 is identical to acid structural unit (S9) employed in single compound syntheses.

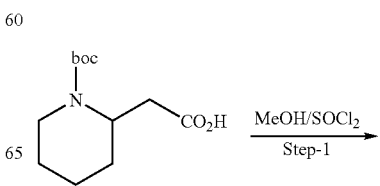

-continued

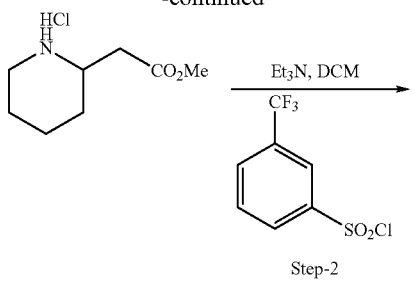

Step-2

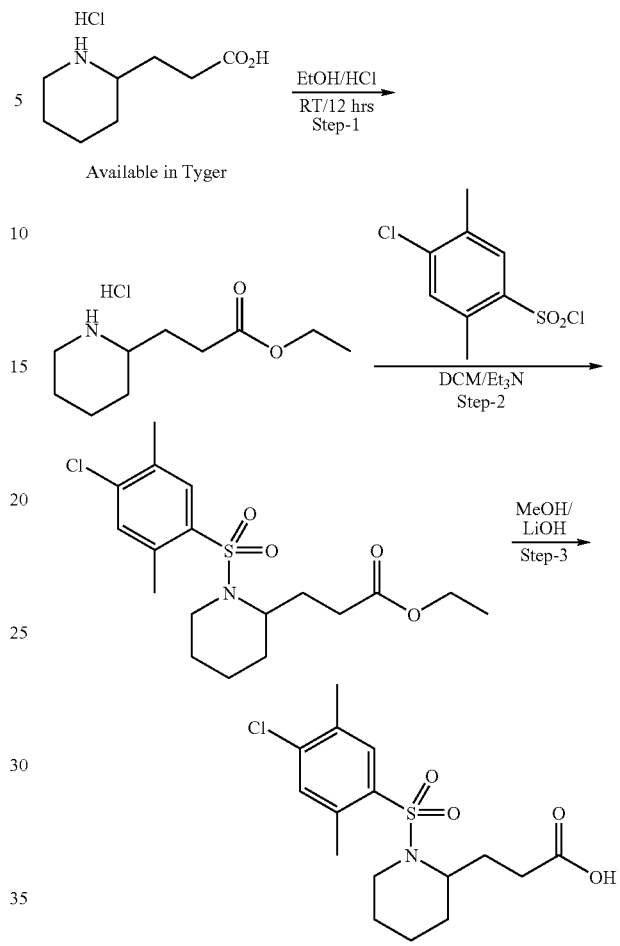

Step-1: To a cold (0° C.) methanolic solution (60 ml) of 2-(1-(tert-butoxycarbonyl)piperidin-2-yl)acetic acid (25 mmol) was added thionyl chloride (3 eq.) and the resulting reaction mixture was refluxed for 16 h. The solvent was completely evaporated and crude solid was used directly in the next step. Yield: 90%

Step-2: A solution of the 3-trifluoromethylbenzene sulfonyl chloride (1 eq.) in dichloromethane (70 ml) was added dropwise to a cold (0° C.) solution of the ester prepared in step-1 (12 mmol, 1 eq.) in dichloromethane (100 ml) and triethylamine (2.5 eq.), maintaining the temperature at 0° C. After complete addition, reaction mixture was stirred at rt for 90 mins. Organic layer was separated, washed with water and brine, dried over sodium sulfate and evaporated under reduced pressure to get the crude product which was pure enough to use in the next step. Yield: 80%

Step-3: To the ester (12 mmol) obtained in step-2 was added a mixture of THF—H$_2$O (8:2, 220 ml) at rt and the reaction mixture was cooled to 0° C. To this cold reaction mixture was added LiOH (2 eq.) and the resulting solution was stirred at ambient temperature for 16 h. Solvent was completely evaporated under reduced pressure, residue dissolved in water, washed with dichloromethane and the aqueous layer was acidified carefully with 1(N)HCl. It was extracted with ethyl acetate, washed successively with water and brine and finally dried over sodium sulfate. Evaporation of the organic layer gave the pure acid. Yield: 90%

Synthesis of acid ACI-CC-06: 3-(1-(4-Chloro-2,5-dimethylphenylsulfonyl)piperidin-2-yl)propanoic acid (ACI-CC-06)

Parallel synthesis acid building block ACI-CC-06 is identical to acid structural unit (S7) employed in single compound syntheses.

Step-1: 3-Piperidin-2-yl-propionic acid hydrochloride (5 g) was treated with ethanol (200 ml) saturated with HCl gas at 0° C. and the resulting reaction mixture was stirred at ambient temperature for 16 h (monitored by LCMS). Solvent was completely evaporated under reduced pressure and the crude material was used directly in the next step without any further purification. Yield: 90%

Step-2: To a dichloromethane solution (60 ml) of the ester obtained in step-1 (20 mmol) was added 4-chloro-2,5-dimethyl benzenesulfonyl chloride (25 mmol) and the resulting reaction mixture was cooled to 0° C. To this cold reaction mixture was added triethylamine (60 mmol) dropwise over a period of 15 minutes. The reaction was stirred at this temperature for 4 h (monitored by TLC). After the starting material was completely consumed, the reaction mixture was diluted with dichloromethane, washed successively with water and brine and finally dried over sodium sulfate. Evaporation of the organic layer under reduced pressure gave the crude sulfonamide which was purified by column chromatography (9:1 Ethyl acetate in hexane) Yield: 80%

Step-3: To the ester (9 mmol) obtained from step-2 was added a mixture of methanol-H$_2$O (3:1, 90 ml) at it and the reaction mixture was cooled to 0° C. To this cold reaction mixture was added LiOH (2 eq.) and the resulting solution was stirred at ambient temperature for 16 h. Solvent was completely evaporated under reduced pressure, residue dissolved in water, washed with dichloromethane and the aqueous layer was acidified carefully with 1(N)HCl. It was extracted with ethyl acetate, washed successively with water and brine and finally dried over sodium sulfate. Evaporation of the organic layer gave the pure acid. Yield: 80%

Synthesis of acid ACI-CC-07: 3-(Naphthalene-2-sulfonamido)-3-phenylpropanoic acid (ACI-CC-07)

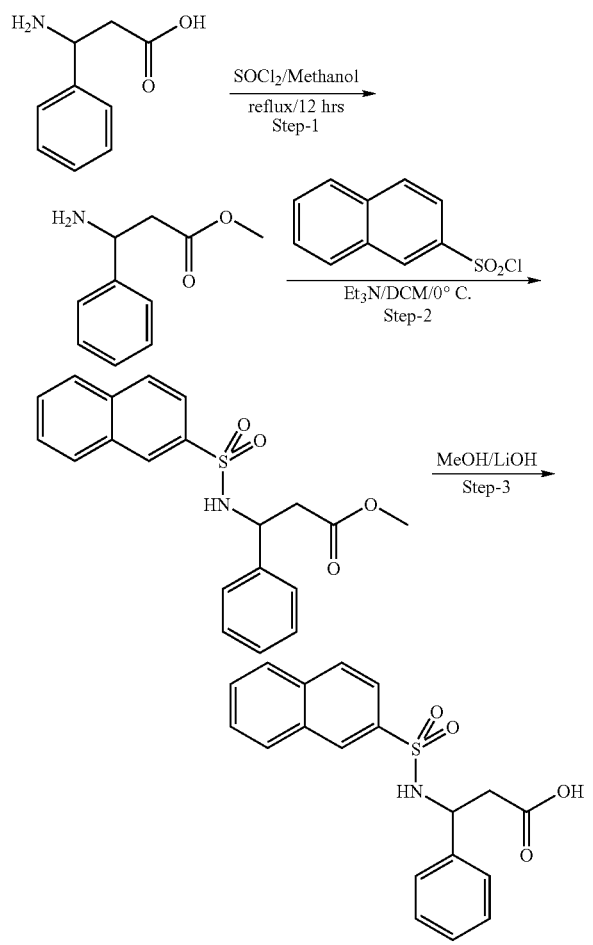

Step-1: To a cold (0° C.) solution of 3-amino-3-phenylpropionic acid (54 mmol) in methanol (3 ml/mmol) was added thionyl chloride (3 eq.) dropwise and the resulting reaction mixture was refluxed for 12 h (monitored by LCMS). Solvent was completely evaporated and the residue was dried under vacuum. It was directly used in the next step without any further purification. Yield: 90%

Step-2: To a cold (0° C.) suspension of the ester (32 mmol) obtained from step-1 in dichloromethane (200 ml) was added triethylamine (3 eq.) and the resulting reaction mixture was treated with a solution of naphthalene-2-sulfonyl chloride (1.2 eq.) in dichloromethane (50 ml). The resulting reaction mixture was stirred at rt for 3 h (monitored by TLC). It was diluted with dichloromethane, washed with water and brine and finally dried over sodium sulfate. Evaporation of the organic layer gave the crude product which was purified by column chromatography (3:7 ethyl acetate in hexane). Yield: 80%

Step-3: To the ester (9 mmol) obtained from step-2 was added a mixture of methanol-H$_2$O (3:1, 90 ml) at rt and the reaction mixture was cooled to 0° C. To this cold reaction mixture was added LiOH.H$_2$O (2 eq) and the resulting solution was stirred at ambient temperature for 16 h. Solvent was completely evaporated under reduced pressure, residue dissolved in water, washed with dichlormethane and the aqueous layer was acidified carefully with 1(N)HCl. It was extracted with ethyl acetate, washed successively with water and brine and finally dried over sodium sulfate. Evaporation of the organic layer gave the pure acid. Yield: 80%

Synthesis of acid ACI-CC-08: 4-(1-(4-Methoxy-2,6-dimethylphenylsulfonyl)piperidin-2-yl)butanoic acid (ACI-CC-08)

Parallel synthesis acid building block ACI-CC-08 is identical to acid structural unit (S8) employed in single compound syntheses.

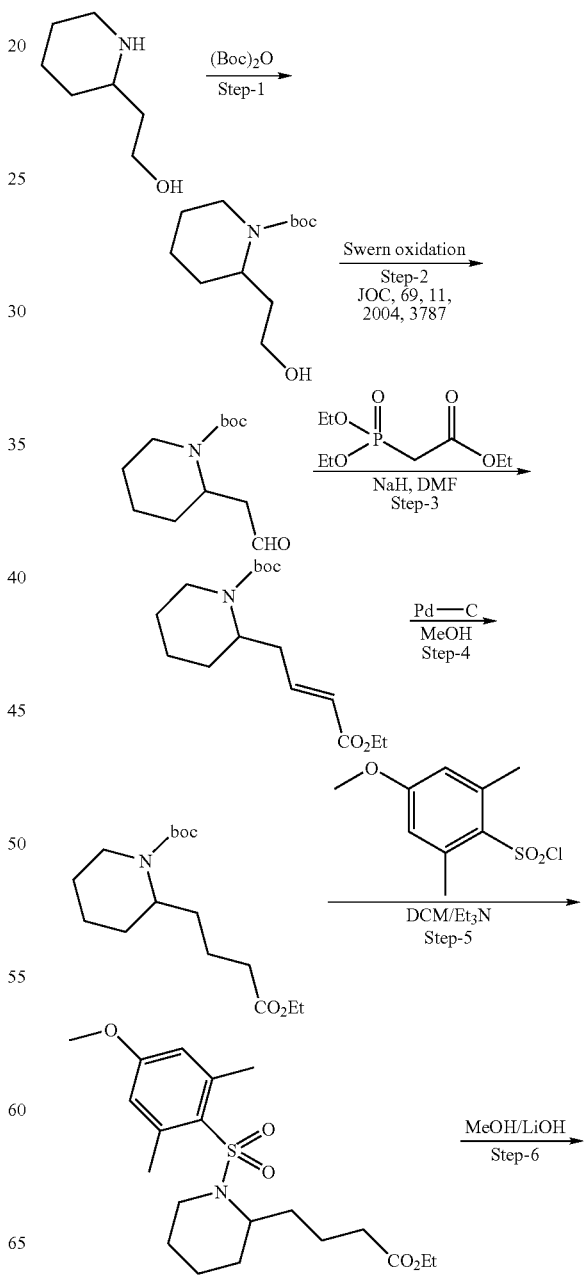

-continued

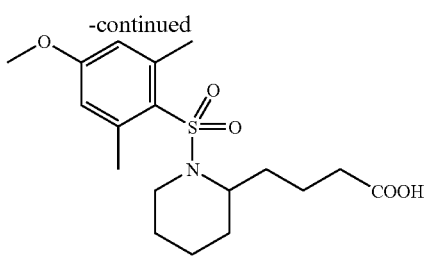

Step-1: To a dichloromethane solution (5 ml/mmol) of piperidine-2-ethanol (1 eq.) was added DIPEA (1.5 eq.) and boc-anhydride (1.2 eq.) at 0° C. and the resulting reaction mixture was stirred at 25° C. for 12 h. Reaction mixture was diluted with dichloromethane; organic layer was washed successively with water and brine and finally dried over sodium sulfate. Organic layer was evaporated under reduced pressure to get the crude product that was purified by column chromatography. Yield: 78%

Step-2: To a dichloromethane solution (3 ml/mmol) of oxalyl chloride (1.1 eq.) was added DMSO (2 eq.) at ±78° C. under argon atmosphere and the resulting reaction mixture was stirred at this temperature for 15 minutes. To this cold reaction mixture was added boc-protected alcohol (1 eq.) obtained from step-1 in dichloromethane (3 ml/mmol) drop wise and it was stirred at this temperature for 1 h. Triethylamine (5 eq.) was added to the reaction, it was slowly brought to ambient temperature and was stirred at this temperature for 1 h. Reaction mixture was diluted with dichloromethane, organic layer was washed successively with saturated aqueous ammonium chloride, water, brine and finally dried over sodium sulfate. Evaporation of organic layer under reduced pressure gave the crude product that was used directly in the next step without any further purification. Yield: 80% (crude)

Step-3: To a cold (0° C.) suspension of 60% NaH (1.1 eq.) in dry THF (5 ml/mmol) was added slowly a solution of triethyl phosphonoacetate (1.1 eq.) in THF (5 ml/mmol) and the resulting reaction mixture was stirred at 25° C. for 30 minutes. It was then cooled to 0° C. and the aldehyde obtained from step-2 (1 eq.) in dry THF (5 ml/mmol) was added dropwise maintaining the same temperature. The reaction mixture was stirred at 25° C. for 16 h by which time starting material was completely consumed. It was quenched with ice and brine solution, aqueous layer was extracted with ethyl acetate and the organic layer was washed successively with water and brine. It was dried over sodium sulfate and evaporated under reduced pressure to get the crude product, which was purified by column chromatography (50% ethyl acetate in hexane). Yield: 59%

Step-4: A solution of the ester (1 eq) obtained from step-3 in MeOH (5 ml/mmol) was deoxygenated with argon for 15 minutes followed by the addition of 10% Pd/C (50% by weight) and the resulting reaction mixture was hydrogenated under atmospheric pressure for 1 hr (monitored by LCMS). It was filtered through celite bed; residue washed with methanol and the combined organic layer were evaporated completely to get the crude product that was used directly in the next step without any further purification. Yield: 90% (crude)

Step-5: To a dichloromethane solution of Boc-protected ester (1 eq.) obtained from step-4 was added 20% TFA in dichloromethane (5 ml/mol) at 0° C. and the resulting reaction mixture was stirred at 25° C. for 3 h (monitored by TLC). Solvent was completely evaporated, dried properly to remove traces of TFA and the crude material was again taken in dichloromethane and cooled to 0° C. To this cold reaction mixture was added TEA (4 eq.), 4-Methoxy-2,6-dimethylbenzenesulfonyl chloride and the resulting reaction mixture was stirred at 25° C. for 3 h (monitored by TLC). It was diluted with dichloromethane; organic layer was successively washed with water and brine and finally dried over sodium sulfate. Evaporation of organic layer under reduced pressure gave the crude product, which was purified by column chromatography. Yield: 74% (crude)

Step-6: To the ester (12 mmol) obtained from step-5 was added a mixture of THF—H$_2$O (8:2, 220 ml) at rt and the reaction mixture was cooled to 0° C. To this cold reaction mixture was added LiOH (2 eq.) and the resulting solution was stirred at ambient temperature for 16 h. Solvent was completely evaporated under reduced pressure, residue dissolved in water, washed with dichloromethane and the aqueous layer was acidified carefully with 1(N)HCl. It was extracted with ethyl acetate, washed successively with water and brine and finally dried over sodium sulfate. Evaporation of the organic layer gave the desired acid compound. Yield: 93%

3) Parallel Synthesis of Example Compounds (I) (Referred to as CC Amides)

Parallel Synthesis Method for the Preparation of Cc Amides

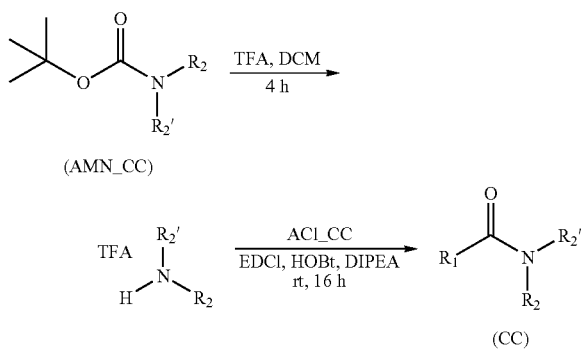

Parallel synthesis of CC amides

Acid building blocks ACI_CC were converted with amines AMN_CC to amides CC in a two step parallel approach. The correlation between product and reagent, building block and method can be taken from the synthesis matrix.

The crude products from the parallel synthesis were analyzed by HPLC_MS and afterwards purified. The identity of the products was demonstrated by analytical HPLC-MS measurements.

Parallelsynthesis: Protocol for the Synthesis of CC Amides

Step-1: Boc-protected amine AMN_CC (1 eq.) was treated with 20% TFA in dichloromethane (10 ml/mol) at 0° C. and the resulting reaction mixture was stirred at 25° C. for 4 h (monitored by TLC). Solvent was completely evaporated, dried properly to remove traces of TFA and the residue was directly used in library synthesis. Yield: Quantitative Step-2: To a dichloromethane solution (3 ml/mmol) of ACI_CC (1 eq.) was added EDCI (1.5 eq), HOBT (1 eq), DIPEA (2.5 eq) and the resulting reaction mixture was stirred for 15 minutes at 25° C. In another flask, the Boc deprotected amine BB (1.5 eq.) in dichloromethane (1 ml/mmol) was cooled in ice bath, treated with DIPEA (4 eq.) and it was added to the reaction mixture. Reaction mixture was stirred at 25° C. for 16 h and diluted with dichloromethane. Organic layer was successively washed with aqueous ammonium chloride, sodium bicarbonate and brine and finally dried over sodium sulfate. Evaporation of organic layer under reduced pressure gave the crude product, which was purified by Biotage parallel purification system. Yield: 20-50%.

Synthesis Matrix and Analytical Data of Parallel Synthesis Examples

| Example No. | Name | Acid (ACI_CC) | Amine (AMN_CC) | Analytical data LC/MS [M+] found |
|---|---|---|---|---|
| CC-01 | 1-[3-(3-Fluorophenyl)-3-pyrrolidin-1-yl-9-azaspiro[5.5]undecan-9-yl]-2-[1-[[3-(trifluoromethyl)phenyl]sulfonyl]-piperidin-2-yl]-ethanone (CC-01) | 2-[1-[[3-(Trifluoromethyl)phenyl]sulfonyl]-piperidin-2-yl]-acetic acid (ACI_CC-05) | 9-(3-Fluorophenyl)-9-pyrrolidin-1-yl-3-azaspiro[5.5]undecane-3-carboxylic acid tert-butyl ester (AMN_CC-01) | 650.2 |
| CC-02 | 1-[3-(3-Fluorophenyl)-3-pyrrolidin-1-yl-9-azaspiro[5.5]undecan-9-yl]-4-[1-[(4-methoxy-2,6-dimethyl-phenyl)sulfonyl]-piperidin-2-yl]-butan-1-one (CC-02) | 4-[1-[(4-Methoxy-2,6-dimethyl-phenyl)sulfonyl]-piperidin-2-yl]-butyric acid (ACI_CC-08) | 9-(3-Fluorophenyl)-9-pyrrolidin-1-yl-3-azaspiro[5.5]undecane-3-carboxylic acid tert-butyl ester (AMN_CC-01) | 668.4 |
| CC-03 | 1-[3-(3-Fluorophenyl)-3-pyrrolidin-1-yl-9-azaspiro[5.5]undecan-9-yl]-2-[[1-[(4-methoxy-2,6-dimethyl-phenyl)sulfonyl]-piperidin-2-yl]-methoxy]-ethanone (CC-03) | 2-[[1-[(4-Methoxy-2,6-dimethyl-phenyl)sulfonyl]-piperidin-2-yl]-methoxy]-acetic acid (ACI_CC-01) | 9-(3-Fluorophenyl)-9-pyrrolidin-1-yl-3-azaspiro[5.5]undecane-3-carboxylic acid tert-butyl ester (AMN_CC-01) | 670.4 |
| CC-04 | N-Cyclopropyl-N-[2-[2-[3-(3-fluorophenyl)-3-pyrrolidin-1-yl-9-azaspiro[5.5]undecan-9-yl]-2-oxo-ethoxy]-ethyl]-4-methoxy-2,6-dimethyl-benzenesulfonic acid amide (CC-04) | 2-[2-[Cyclopropyl-[(4-methoxy-2,6-dimethyl-phenyl)sulfonyl]-amino]-ethoxy]-acetic acid (ACI_CC-02) | 9-(3-Fluorophenyl)-9-pyrrolidin-1-yl-3-azaspiro[5.5]undecane-3-carboxylic acid tert-butyl ester (AMN_CC-01) | 656.2 |
| CC-05 | 2-[[1-[(2-Chloro-6-methyl-phenyl)sulfonyl]-piperidin-2-yl]-methoxy]-1-[3-(3-fluorophenyl)-3-pyrrolidin-1-yl-9-azaspiro[5.5]undecan-9-yl]-ethanone (CC-05) | 2-[[1-[(2-Chloro-6-methyl-phenyl)sulfonyl]-piperidin-2-yl]-methoxy]-acetic acid (ACI_CC-03) | 9-(3-Fluorophenyl)-9-pyrrolidin-1-yl-3-azaspiro[5.5]undecane-3-carboxylic acid tert-butyl ester (AMN_CC-01) | 660.3 |
| CC-06 | 2-Chloro-N-cyclopropyl-N-[2-[2-[3-(3-fluorophenyl)-3-pyrrolidin-1-yl-9-azaspiro[5.5]undecan-9-yl]-2-oxo-ethoxy]-ethyl]-6-methyl-benzenesulfonic acid amide (CC-06) | 2-[2-[[(2-Chloro-6-methyl-phenyl)sulfonyl]-cyclopropyl-amino]-ethoxy]-acetic acid (ACI_CC-04) | 9-(3-Fluorophenyl)-9-pyrrolidin-1-yl-3-azaspiro[5.5]undecane-3-carboxylic acid tert-butyl ester (AMN_CC-01) | 646.4 |
| CC-07 | 3-[1-[(4-Chloro-2,5-dimethyl-phenyl)sulfonyl]-piperidin-2-yl]-1-[3-(3-fluorophenyl)-3-pyrrolidin-1-yl-9-azaspiro[5.5]undecan-9-yl]-propan-1-one (CC-07) | 3-[1-[(4-Chloro-2,5-dimethyl-phenyl)sulfonyl]-piperidin-2-yl]-propionic acid (ACI_CC-06) | 9-(3-Fluorophenyl)-9-pyrrolidin-1-yl-3-azaspiro[5.5]undecane-3-carboxylic acid tert-butyl ester (AMN_CC-01) | 658.3 |
| CC-08 | N-[3-[3-(3-Fluorophenyl)-3-pyrrolidin-1-yl-9-azaspiro[5.5]undecan-9-yl]-3-oxo-1-phenyl-propyl]-naphthalene-2-sulfonic acid amide (CC-08) | 3-[(Naphthalen-2-ylsulfonyl)amino]-3-phenyl-propionic acid (ACI_CC-07) | 9-(3-Fluorophenyl)-9-pyrrolidin-1-yl-3-azaspiro[5.5]undecane-3-carboxylic acid tert-butyl ester (AMN_CC-01) | 654.5 |
| CC-09 | 2-Chloro-N-cyclopropyl-N-[2-[2-(3-dimethylamino-3-thiophen-2-yl-9-azaspiro[5.5]undecan-9-yl)-2-oxo-ethoxy]-ethyl]-6-methyl-benzenesulfonic acid amide (CC-09) | 2-[2-[[(2-Chloro-6-methyl-phenyl)sulfonyl]-cyclopropyl-amino]-ethoxy]-acetic acid (ACI_CC-04) | 9-Dimethylamino-9-thiophen-2-yl-3-azaspiro[5.5]undecane-3-carboxylic acid tert-butyl ester (AMN_CC-02) | 608.3 |
| CC-10 | 1-(3-Dimethylamino-3-thiophen-2-yl-9-azaspiro[5.5]undecan-9-yl)-2-[1-[[3-(trifluoromethyl)phenyl]sulfonyl]-piperidin-2-yl]-ethanone (CC-10) | 2-[1-[[3-(Trifluoromethyl)phenyl]sulfonyl]-piperidin-2-yl]-acetic acid (ACI_CC-05) | 9-Dimethylamino-9-thiophen-2-yl-3-azaspiro[5.5]undecane-3-carboxylic acid tert-butyl ester (AMN_CC-02) | 612.2 |
| CC-11 | 1-(3-Dimethylamino-3-thiophen-2-yl-9-azaspiro[5.5]undecan-9-yl)-2-[[1-[(4-methoxy-2,6-dimethyl-phenyl)sulfonyl]-piperidin-2-yl]-methoxy]-ethanone (CC-11) | 2-[[1-[(4-Methoxy-2,6-dimethyl-phenyl)sulfonyl]-piperidin-2-yl]-methoxy]-acetic acid (ACI_CC-01) | 9-Dimethylamino-9-thiophen-2-yl-3-azaspiro[5.5]undecane-3-carboxylic acid tert-butyl ester (AMN_CC-02) | 632.4 |
| CC-12 | N-Cyclopropyl-N-[2-[2-(3-dimethylamino-3-thiophen-2-yl-9-azaspiro[5.5]undecan-9-yl)-2-oxo-ethoxy]-ethyl]-4-methoxy-2,6-dimethyl-benzenesulfonic acid amide (CC-12) | 2-[2-[Cyclopropyl-[(4-methoxy-2,6-dimethyl-phenyl)sulfonyl]-amino]-ethoxy]-acetic acid (ACI_CC-02) | 9-Dimethylamino-9-thiophen-2-yl-3-azaspiro[5.5]undecane-3-carboxylic acid tert-butyl ester (AMN_CC-02) | 618.4 |
| CC-13 | 2-[[1-[(2-Chloro-6-methyl-phenyl)sulfonyl]-piperidin-2-yl]-methoxy]-1-(3-dimethylamino-3-thiophen-2-yl-9-azaspiro[5.5]undecan-9-yl)-ethanone (CC-13) | 2-[[1-[(2-Chloro-6-methyl-phenyl)sulfonyl]-piperidin-2-yl]-methoxy]-acetic acid (ACI_CC-03) | 9-Dimethylamino-9-thiophen-2-yl-3-azaspiro[5.5]undecane-3-carboxylic acid tert-butyl ester (AMN_CC-02) | 622.3 |
| CC-14 | 3-[1-[(4-Chloro-2,5-dimethyl-phenyl)sulfonyl]-piperidin-2-yl]-1-(3-dimethylamino-3-thiophen-2-yl-9-azaspiro[5.5]undecan-9-yl)-propan-1-one (CC-14) | 3-[1-[(4-Chloro-2,5-dimethyl-phenyl)sulfonyl]-piperidin-2-yl]-propionic acid (ACI_CC-06) | 9-Dimethylamino-9-thiophen-2-yl-3-azaspiro[5.5]undecane-3-carboxylic acid tert-butyl ester (AMN_CC-02) | 620.4 |
| CC-15 | N-[3-(3-Dimethylamino-3-thiophen-2-yl-9-azaspiro[5.5]undecan-9-yl)-3-oxo-1-phenyl-propyl]-naphthalene-2-sulfonic acid amide (CC-15) | 3-[(Naphthalen-2-ylsulfonyl)amino]-3-phenyl-propionic acid (ACI_CC-07) | 9-Dimethylamino-9-thiophen-2-yl-3-azaspiro[5.5]undecane-3-carboxylic acid tert-butyl ester (AMN_CC-02) | 616.4 |
| CC-16 | 1-(3-Dimethylamino-3-thiophen-2-yl-9-azaspiro[5.5]undecan-9-yl)-4-[1-[(4-methoxy-2,6-dimethyl-phenyl)sulfonyl]-piperidin-2-yl]-butan-1-one (CC-16) | 4-[1-[(4-Methoxy-2,6-dimethyl-phenyl)sulfonyl]-piperidin-2-yl]-butyric acid (ACI_CC-08) | 9-Dimethylamino-9-thiophen-2-yl-3-azaspiro[5.5]undecane-3-carboxylic acid tert-butyl ester (AMN_CC-02) | 630.5 |

Pharmacological Data

The following pharmacological data was determined using the methods described above.

| Compound | % Inh. (rat B1R) 10 μM | % Inh. (hum. B1R) 10 μM | μ-Opioid receptor [1 μM] % Inhibition |
|---|---|---|---|
| 1 | 92 | 100 | 85 |
| 2 | 94 | 100 | 102 |
| 3 | 102 | 100 | 100 |
| 4 | 102 | 98 | 99 |
| 5 | 99 | 77 | 99 |
| 6 | 97 | 100 | 98 |
| 7 | 97 | 98 | 101 |
| 8 | 98 | 98 | 103 |
| 9 | 38 | 92 | 103 |
| 10 | 92 | 100 | 96 |
| 11 | 104 | 100 | 106 |
| 12 | 102 | 100 | 84 |
| 13 | 104 | 86 | 2 |
| CC-01 | 75 | 73 | 12 |
| CC-02 | 98 | 100 | 47 |
| CC-03 | 99 | 100 | 37 |
| CC-04 | 98 | 100 | 78 |
| CC-05 | 98 | 100 | 54 |
| CC-06 | 97 | 100 | 77 |
| CC-07 | 86 | 99 | 26 |
| CC-08 | 96 | 81 | 86 |
| CC-09 | 97 | 100 | 102 |
| CC-10 | 79 | 84 | 102 |
| CC-11 | 98 | 100 | 103 |
| CC-12 | 97 | 100 | 100 |
| CC-13 | 98 | 100 | 97 |
| CC-14 | 101 | 99 | 99 |
| CC-15 | 100 | 69 | 105 |
| CC-16 | 102 | 99 | 95 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A substituted spiroamine compound corresponding to formula (I):

(I)

wherein
r, s and t each independently represent 0, 1 or 2;
m, n, o and p each represent 2;
Q denotes a single bond, —O— or —CH$_2$—;
R$^1$ denotes CH(aryl)$_2$, aryl, heteroaryl or an aryl or heteroaryl group bonded via a C$_{1-3}$ alkylene group;
R$^2$ and R$^3$ are as defined under (i) or (ii):
(i) R$^2$ denotes H, C$_{1-6}$ alkyl, C$_{3-8}$ cycloalkyl, bicyclic 8-12-membered carbocyclyl, CH(aryl)$_2$, aryl or heteroaryl, or R$^2$ denotes a C$_{3-8}$ cycloalkyl, bicyclic 8-12-membered carbocyclyl, CH(aryl)$_2$, aryl or heteroaryl group bonded via a C$_{1-6}$ alkylene group or C$_{2-6}$ alkenylene group; and R$^3$ denotes H, F, Cl, Br, I, —CF$_3$, —OCF$_3$, OH, COOR$^{16}$, CONR$^{17}$R$^{18}$, O—C$_{1-6}$ alkyl,
C$_{1-6}$ alkyl, C$_{3-8}$ cycloalkyl, aryl or heteroaryl wherein R$^{16}$ denotes C$_{1-6}$ alkyl;
R$^{17}$ and R$^{18}$ are as defined under (v) or (vi):
(v) R$^{17}$ and R$^{18}$ each independently denote H or C$_{1-6}$ alkyl; or
(vi) R$^{17}$ and R$^{18}$ together with the nitrogen atom linking them form a heterocycle which optionally may be substituted at one or more of its carbon ring members with one or more substituents each independently selected from the group consisting of F, Cl, Br, I, —NH$_2$, —CF$_3$, =O, —O—CF$_3$, —OH, —SH, —O—C$_{1-6}$ alkyl, C$_{1-6}$ alkyl, C$_{3-8}$ cycloalkyl, aryl and heteroaryl and/or anellated with a saturated, mono- or polyunsaturated or aromatic ring system which optionally may be substituted at one or more of its carbon ring members with one or more substituents each independently selected from the group consisting of F, Cl, Br, I, —NH$_2$, —CF$_3$, =O, —O—CF$_3$, —OH, —SH, —O—C$_{1-6}$ alkyl, C$_{1-6}$ alkyl, C$_{3-8}$ cycloalkyl, aryl and heteroaryl,
wherein said heterocycle may be saturated, mono- or polyunsaturated but not aromatic, is 4-,5-,6- or 7-membered, in addition to the N-heteroatom to which R$^8$ and R$^9$ are bound optionally may also contain one or more further heteroatoms or a heteroatom group selected from the group consisting of N, NR$^{19}$, O, S, S=O and S(=O)$_2$, the ring system is 4-,5-,6- or 7-membered, can contain at least one heteroatom or a heteroatom group selected from the group consisting of N, NR$^{20}$, O, S, S=O and S(=O)$_2$, wherein
R$^{19}$ denotes H, or a C$_{1-6}$ alkyl, C$_{3-8}$ cycloalkyl, aryl or heteroaryl group or an aryl, heteroaryl or C$_{3-8}$ cycloalkyl group bonded via a C$_{1-3}$ alkylene group, and
R$^{20}$ denotes H, or a C$_{1-6}$ alkyl, C$_{3-8}$ cycloalkyl, aryl or heteroaryl group, or an aryl, heteroaryl or C$_{3-8}$ cycloalkyl group bonded via a C$_{1-3}$ alkylene group; or
R$^3$ denotes a C$_{3-8}$ cycloalkyl, aryl or heteroaryl group bonded via a C$_{1-6}$ alkylene group or C$_{2-6}$ alkenylene group; or
(ii) R$^2$ and R$^3$ together with the —N—(CR$^{4a}$R$^{4b}$)$_r$—CH— group linking them form a heterocycle which optionally may be substituted at one or more of its carbon ring members with one or more substituents each independently selected from the group consisting of F, Cl, Br, I, —NH$_2$, —CF$_3$, =O, —O—CF$_3$, —OH, —SH, —O—C$_{1-6}$ alkyl, C$_{1-6}$ alkyl, C$_{3-8}$ cycloalkyl, aryl and heteroaryl and/or anellated with at least one optionally substituted aryl or heteroaryl,
wherein said heterocycle may be saturated or mono- or polyunsaturated, but is not aromatic, is 4-, 5-, 6- or 7-membered, and in addition to the N-heteroatom to which R$^2$ is bound optionally may also contain one or more heteroatoms or heteroatom groups independently selected from the group consisting of N, NR$^{12}$, O, S, S=O or S(=O)$_2$; wherein
R$^{12}$ denotes H, C$_{1-6}$ alkyl, —C(=O)—R$^{13}$, C$_{3-8}$ cycloalkyl, aryl, heteroaryl or a C$_{3-8}$ cycloalkyl, aryl or heteroaryl group bonded via a C$_{1-3}$ alkylene group, and R$^{13}$ denotes C$_{1-6}$ alkyl, C$_{3-8}$ cycloalkyl, aryl, heteroaryl or a C$_{3-8}$ cycloalkyl, aryl or heteroaryl group bonded via a C$_{1-3}$ alkylene group;

R$^{4a}$, R$^{4b}$, R$^{5a}$, R$^{5b}$, R$^{6a}$ and R$^{6b}$ each independently represent H, F, Cl, Br, I, —CF$_3$, —OCF$_3$, OH, SH, O—C$_{1-6}$ alkyl, C$_{1-6}$ alkyl, C$_{3-8}$ cycloalkyl, aryl or heteroaryl; or a C$_{3-8}$ cycloalkyl, aryl or heteroaryl group bonded via a C$_{1-6}$ alkylene group or C$_{2-6}$ alkenylene group;

R$^7$ denotes aryl, heteroaryl or for an aryl or heteroaryl group bonded via a C$_{1-3}$ alkylene group;

R$^8$ and R$^9$ are as defined under (iii) or (iv):

(iii) R$^8$ and R$^9$ each independently denote H, C$_{1-6}$ alkyl, C$_{2-6}$ alkenyl, C$_{3-8}$ cycloalkyl, 3- to 8-membered heterocycloalkyl, aryl or heteroaryl or a C$_{3-8}$ cycloalkyl, 3- to 8-membered heterocycloalkyl, aryl or heteroaryl group bonded via a C$_{1-3}$ alkylene group; or (iv) R$^8$ and R$^9$ together with the nitrogen atom linking them form a heterocycle which optionally may be substituted at one or more of its carbon ring members with one or more substituents each independently selected from the group consisting of F, Cl, Br, I, —NH$_2$, —CF$_3$, =O, —O—CF$_3$, —OH, —SH, —O—C$_{1-6}$ alkyl, C$_{1-6}$ alkyl, C$_{3-8}$ cycloalkyl, aryl, heteroaryl, C$_{1-3}$ alkylene-C$_{3-8}$ cycloalkyl, C$_{1-3}$ alkylene-aryl and C$_{1-3}$ alkylene-heteroaryl and/or anellated with a saturated, mono- or poly-unsaturated or aromatic ring system which optionally may be substituted at one or more of its carbon ring members with one or more substituents each independently selected from the group consisting of F, Cl, Br, I, —NH$_2$, —CF$_3$, =O, —O—CF$_3$, —OH, —SH, —O—C$_{1-6}$ alkyl, C$_{1-6}$ alkyl, C$_{3-8}$ cycloalkyl, aryl, heteroaryl, C$_{1-3}$ alkylene-C$_{3-8}$-cycloalkyl, C$_{1-3}$ alkylene-aryl and C$_{1-3}$ alkylene-heteroaryl, wherein said heterocycle may be saturated, mono- or polyunsaturated but not aromatic, is 4-, 5-, 6- or 7-membered, in addition to the N-heteroatom to which R$^8$ and R$^9$ are bound optionally may also contain at least one further heteroatom or a heteroatom group selected from the group consisting of N, NR$^{14}$, O, S, S=O and S(=O)$_2$, the ring system is 4-, 5-, 6- or 7-membered, can contain at least one heteroatom or a heteroatom group selected from the group consisting of N, NR$^{15}$, O, S, S=O and S(=O)$_2$; wherein R$^{14}$ denotes a group selected from the group consisting of H, C$_{1-6}$ alkyl, C$_{3-8}$ cycloalkyl, aryl, heteroaryl or for an aryl, heteroaryl or C$_{3-8}$ cycloalkyl bonded via a C$_{1-3}$ alkylene group, and R$^{15}$ denotes a group selected from the group consisting of H, C$_{1-6}$ alkyl, C$_{3-8}$ cycloalkyl, aryl, heteroaryl or for an aryl, heteroaryl or C$_{3-8}$ cycloalkyl bonded via a C$_{1-3}$ alkylene group; and R$^{10}$ and R$^{11}$ each independently represent 0 to 4 substituents each independently selected from the group consisting of F, OH, C$_{1-6}$ alkyl, C$_{3-8}$ cycloalkyl, aryl, heteroaryl and C$_{3-8}$ cycloalkyl, aryl or heteroaryl group bonded via a C$_{1-6}$ alkylene group;

wherein said C$_{1-6}$ alkyl, C$_{2-6}$ alkenyl, C$_{1-3}$ alkylene, C$_{1-6}$ alkylene, C$_{2-6}$ alkenylene, carbocyclyl, 3- to 8-membered heterocycloalkyl, C$_{3-8}$ cycloalkyl, aryl and heteroaryl groups may each be unsubstituted or mono- or polysubstituted with identical or different substituents, and said C$_{1-6}$ alkyl, C$_{2-6}$ alkenyl, C$_{1-3}$ alkylene, C$_{1-6}$ alkylene and C$_{2-8}$ alkenylene groups may each be branched or unbranched;

or a physiologically compatible salt thereof.

2. A compound as claimed in claim 1, wherein said compound is in the form of an isolated stereoisomer.

3. A compound as claimed in claim 1, wherein said compound is in the form of a mixture of stereoisomers in any mixing ratio.

4. A compound as claimed in claim 3, wherein said mixture is a racemic mixture.

5. A compound as claimed in claim 1, wherein R$^1$ denotes a phenyl, naphthyl, indolyl, benzofuranyl, benzothiophenyl, benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl, quinolinyl, isoquinolinyl or CH(phenyl)$_2$ group, or a phenyl or naphthyl group bonded via a C$_{1-3}$ alkylene group; wherein said groups may each be unsubstituted or mono- or polysubstituted, equally or differently, with substituents independently selected from the group consisting of —O—C$_{1-3}$ alkyl, C$_{1-6}$ alkyl, C$_{3-6}$ cycloalkyl, F, Cl, Br, CF$_3$, OCF$_3$, OH, phenyl, phenoxy, naphthyl, thiazolyl, thienyl and pyridinyl.

6. A compound as claimed in claim 5, wherein R$^1$ denotes a phenyl, naphthyl, benzothiophenyl, benzooxadiazolyl, quinolinyl, isoquinolinyl or thienyl group or a phenyl group bonded via a C$_{1-3}$ alkylene group; wherein said groups may be unsubstituted or mono- or polysubstituted.

7. A compound as claimed in claim 1, wherein in formula (I) the substructure (Ac I)

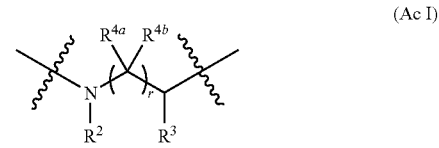

denotes one of the following groups:

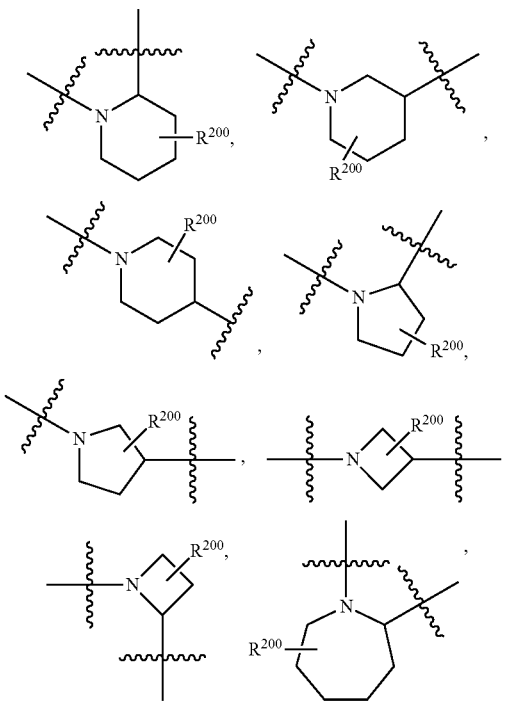

-continued

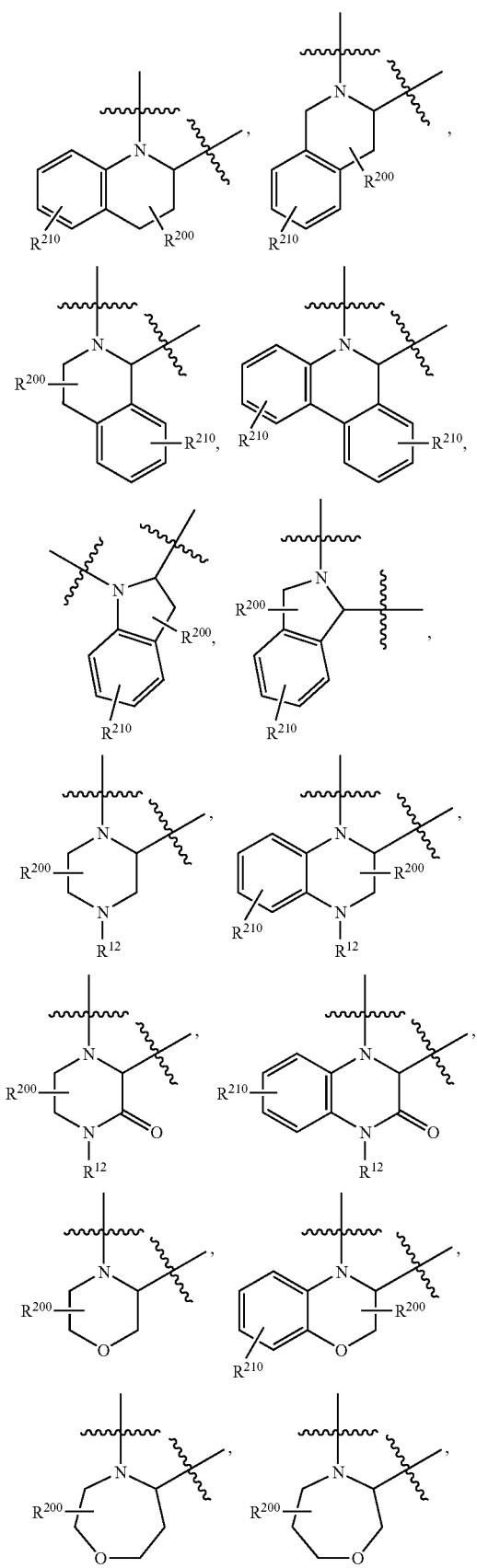

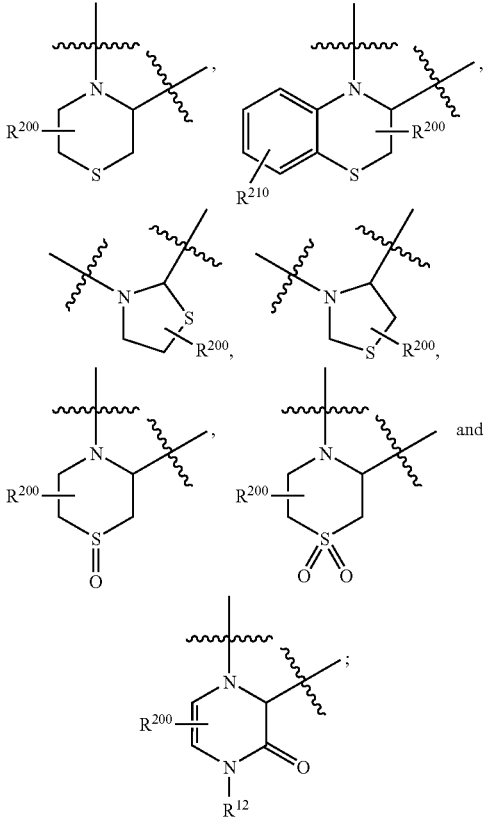

wherein
R²⁰⁰ denotes 0 to 4 substituents each independently selected from the group consisting of F, Cl, —CF₃, =O, —O—CF₃, —OH, —O—C₁₋₆ alkyl and C₁₋₆ alkyl or two adjacent R²⁰⁰ groups together form an anellated aryl or heteroaryl ring;

R²¹⁰ denotes 0 to 4 substituents each independently selected from the group consisting of —O—C₁₋₃ alkyl, C₁₋₆ alkyl, F, Cl, Br, I, CF₃, OCF₃, OH, SH, phenyl, naphthyl, furyl, thienyl and pyridinyl;

R¹² denotes H, C₁₋₆ alkyl, —C(=O)—R¹³, C₃₋₈ cycloalkyl, aryl or heteroaryl or a C₃₋₈ cycloalkyl, aryl or heteroaryl group bonded via a C₁₋₃ alkylene group, and R¹³ denotes C₁₋₆ alkyl, C₃₋₈ cycloalkyl, aryl or heteroaryl or a C₃₋₈ cycloalkyl, aryl or heteroaryl group bonded via a C₁₋₃ alkylene group.

8. A compound as claimed in claim 1, wherein
R² denotes H, C₁₋₆ alkyl, C₃₋₆ cycloalkyl, aryl, heteroaryl or a C₃₋₆ cycloalkyl, aryl or heteroaryl group bonded via a C₁₋₃ alkylene group, in each case unsubstituted or mono- or polysubstituted with identical or different substituents; and R³ denotes H, F, Cl, —CF₃, —OH, —O—C₁₋₆ alkyl, C₁₋₆ alkyl, aryl or heteroaryl; or an aryl or heteroaryl group bonded via a C₁₋₃ alkylene group, in each case unsubstituted or mono- or polysubstituted with identical or different substituents.

9. A compound as claimed in claim 8, wherein
R² denotes H, methyl, ethyl, n-propyl, isopropyl, n-butyl, isobutyl, sec-butyl, tert-butyl, cyclopropyl, phenyl, pyridinyl or a phenyl or pyridinyl group bonded via a C₁₋₃ alkylene group; and $R^3$ denotes H, methyl, ethyl, n-propyl, isopropyl, n-butyl, isobutyl, sec-butyl, tert-butyl, phenyl or pyridinyl.

10. A compound as claimed in claim 1, wherein in formula (I) the following substructure:

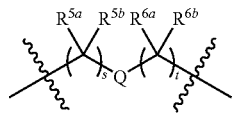

denotes a —$CH_2$—, —$(CH_2)_2$—, —$(CH_2)_3$—, —$(CH_2)_4$— or —$CH_2$—O—$CH_2$ group.

11. A compound as claimed in claim 1, wherein $R^{4a}$, $R^{4b}$, $R^{5a}$, $R^{5b}$, $R^{6a}$ and $R^{6b}$ are each independently selected from the group consisting of H, F, Cl, $CF_3$, OH, $OCF_3$ and $OCH_3$.

12. A compound as claimed in claim 1, wherein $R^7$ denotes a phenyl, naphthyl, thienyl, thiazolyl, pyridinyl or benzyl group which may be unsubstituted or mono- or polysubstituted with substituents independently selected from the group consisting of $C_{1-4}$ alkyl, O—$C_{1-4}$ alkyl, F, Cl, $CF_3$, $OCF_3$ and —CN.

13. A compound as claimed in claim 1, wherein $R^8$ and $R^9$ each independently denote H or unsubstituted or mono- or polysubstituted $C_{1-6}$ alkyl.

14. A compound as claimed in claim 1, wherein $R^8$ and $R^9$ together with the nitrogen atom linking them form a heterocycle corresponding to formula (II)

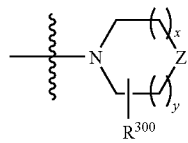

(II)

wherein

Z denotes O, S, $NR^{15a}$, $CH_2$ or C(halogen)$_2$, wherein $R^{15a}$ denotes H; $C_{1-6}$ alkyl; aryl, heteroaryl, or an aryl or heteroaryl group bonded via a $C_{1-3}$ alkylene group;

x and y each independently represent 0, 1 or 2, with the proviso that x+y=0, 1, 2 or 3, and $R^{300}$ denotes 0 to 4 substituents each independently selected from the group consisting of $C_{1-6}$ alkyl, —O—$C_{1-6}$ alkyl, OH, $CF_3$, F, aryl, heteroaryl, $C_{1-3}$ alkylene-aryl and $C_{1-3}$ alkylene-heteroaryl;

wherein said $C_{1-6}$ alkyl, $C_{1-3}$ alkylene, aryl and heteroaryl groups may be unsubstituted or mono- or polysubstituted with identical or different substituents.

15. A compound as claimed in claim 1, wherein $R^{10}$ and $R^{11}$ each independently represent 0 to 4 substituents each independently selected from the group consisting of $C_{1-6}$ alkyl, —O—$C_{1-6}$ alkyl, OH, $CF_3$, F, aryl, heteroaryl, $C_{1-3}$ alkylene-aryl and $C_{1-3}$ alkylene-heteroaryl.

16. A compound as claimed in claim 1, wherein the substructure

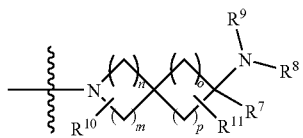

denotes one of the following groups:

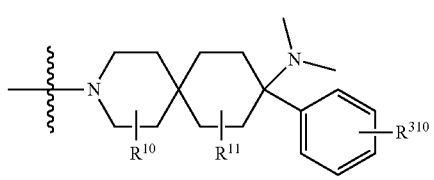

A1

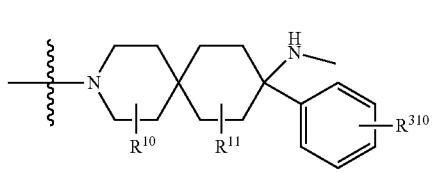

A2

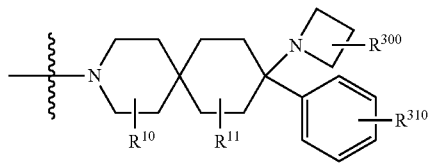

A3

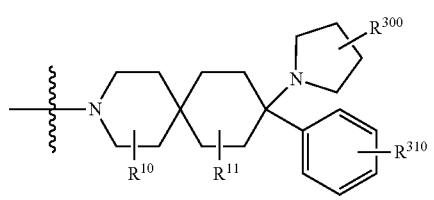

A4

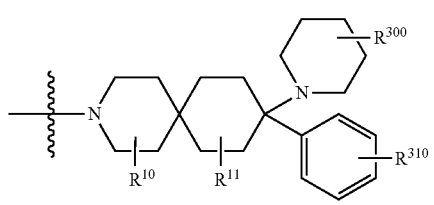

A5

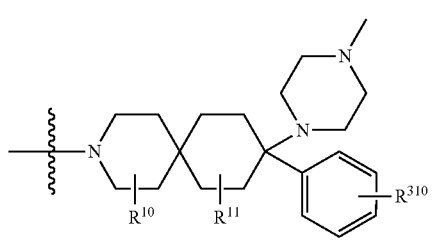

A6

| | |
|---|---|
| 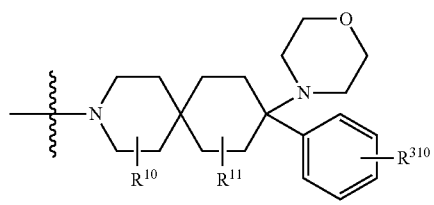 A7 | 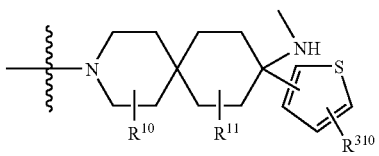 A15 |
| 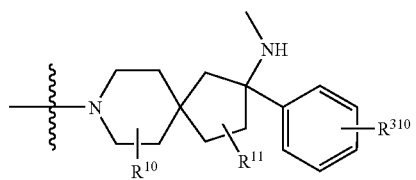 A8 | 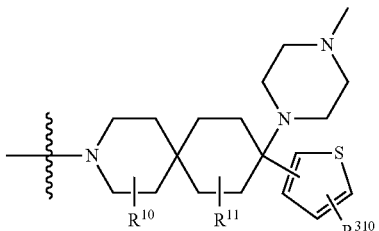 A20 |
| 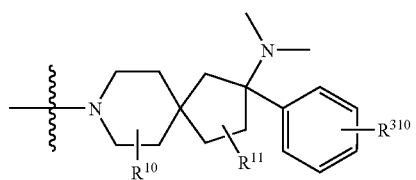 A9 | 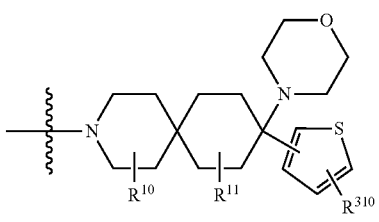 A21 |
| 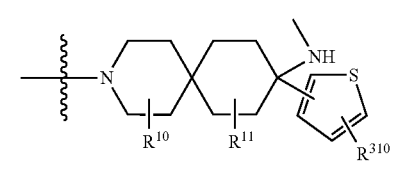 A15 | 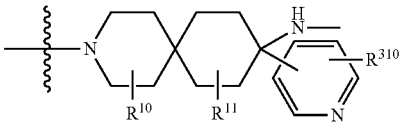 A22 |
| 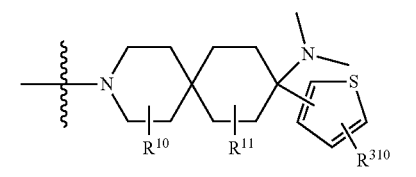 A16 | 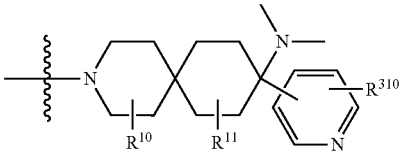 A23 |
| 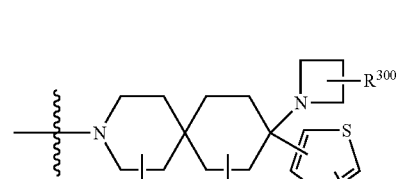 A17 | 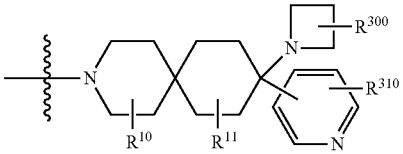 A24 |
| 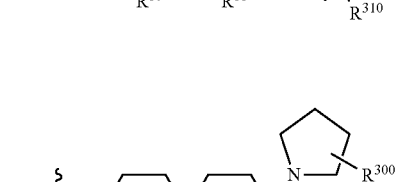 A18 | 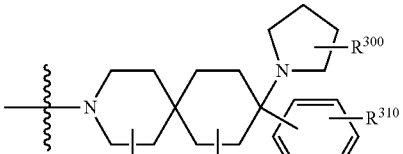 A25 |
| 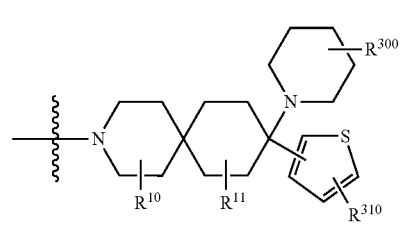 A19 | A26 |

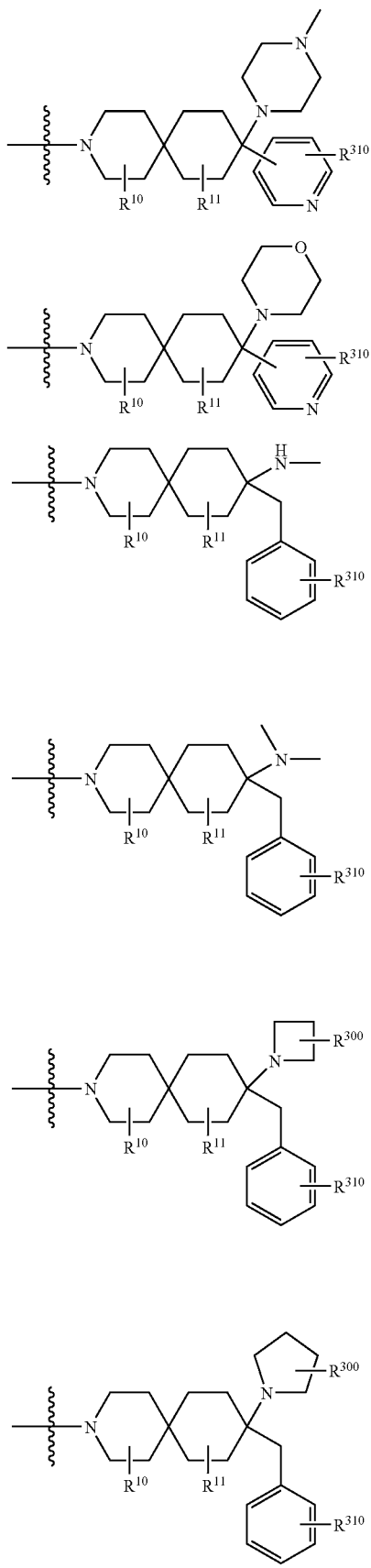

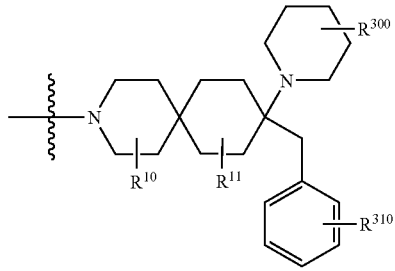

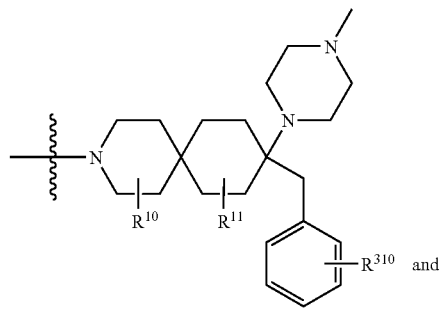

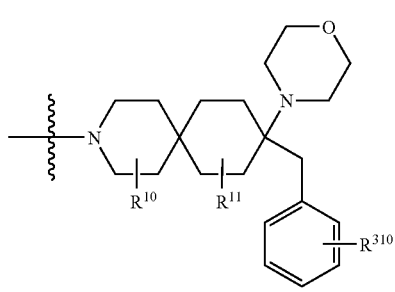

wherein
R$^{10}$ and R$^{11}$ each independently represent 0 to 4 substituents independently selected from the group consisting of C$_{1-6}$ alkyl, —O—C$_{1-6}$ alkyl, OH, CF$_3$, F, aryl, heteroaryl, C$_{1-3}$ alkylene-aryl and C$_{1-3}$ alkylene-heteroaryl;
R$^{300}$ denotes 0 to 4 substituents independently selected from the group consisting of C$_{1-6}$ alkyl, —O—C$_{1-6}$ alkyl, OH, CF$_3$, F, aryl, heteroaryl, C$_{1-3}$ alkylene-aryl and C$_{1-3}$ alkylene-heteroaryl; and
R$^{310}$ denotes 0 to 4 substituents independently selected from the group consisting of F, Cl, Br, C$_{1-6}$ alkyl, O—C$_{1-6}$ alkyl, CF$_3$, OCF$_3$ and CN.

17. A compound as claimed in claim 1, corresponding to formula (Ia)

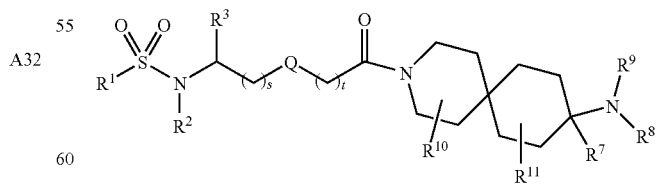

(Ia)

wherein
s and t each independently represent 0, 1 or 2;
Q denotes a single bond, —O— or —CH$_2$—;
R$^1$ denotes phenyl or naphthyl, each unsubstituted or mono- or polysubstituted, identically or differently with substituents each independently selected from the group consisting of —O—$C_{1-3}$ alkyl, $C_{1-6}$ alkyl, F, Cl, Br, $CF_3$, $OCF_3$ and OH;

$R^2$ and $R^3$ are as defined under (i) or (ii):

(i) $R^2$ denotes H, methyl, ethyl, n-propyl, isopropyl, n-butyl, isobutyl, sec-butyl, tert-butyl, cyclopropyl, aryl, heteroaryl, or $R^2$ denotes an aryl or heteroaryl group bonded via a $C_{1-3}$ alkylene group, and $R^3$ denotes H or phenyl, wherein the phenyl may be unsubstituted or mono- or polysubstituted with substituents selected from the group consisting of F, Cl, —$CF_3$, —$OCF_3$, OH, methyl and methoxy; or (ii) $R^2$ and $R^3$ together with the —N—CH— group linking them form a heterocycle which optionally may be substituted at one or more of its carbon ring members with one or more substituents each independently selected from the group consisting of F, Cl, Br, I, —$NH_2$, —$CF_3$, =O, —O—$CF_3$, —OH, —SH, —O—$C_{1-6}$ alkyl, $C_{1-6}$ alkyl, $C_{3-8}$ cycloalkyl, aryl and heteroaryl and/or anellated with at least one optionally substituted aryl or heteroaryl group, wherein said heterocycle may be saturated or mono- or polyunsaturated, but is not aromatic, is 4-, 5-, 6- or 7-membered, and in addition to the N-heteroatom to which $R^2$ is bound optionally may also contain one or more heteroatoms or heteroatom groups independently selected from the group consisting of N, $NR^{12}$, O, S, S=O or S(=O)$_2$; wherein $R^{12}$ denotes H, $C_{1-6}$ alkyl, —C(=O)—$R^{13}$, $C_{3-8}$ cycloalkyl, aryl, heteroaryl or a $C_{3-8}$ cycloalkyl, aryl or heteroaryl group bonded via a $C_{1-3}$ alkylene group, and $R^{13}$ denotes $C_{1-6}$ alkyl, $C_{3-8}$ cycloalkyl, aryl, heteroaryl or a $C_{3-8}$ cycloalkyl, aryl or heteroaryl group bonded via a $C_{1-3}$ alkylene group;

$R^7$ denotes a phenyl, naphthyl, thienyl, thiazolyl, pyridinyl or benzyl group, wherein said group may be unsubstituted or mono- or polysubstituted with substituents each independently selected from the group consisting of $C_{1-4}$ alkyl, O—$C_{1-4}$ alkyl, F, Cl, $CF_3$, $OCF_3$ and —CN;

$R^8$ and $R^9$ are as defined under (iii) or (iv):

(iii) $R^8$ and $R^9$ are each independently selected from the group consisting of H, methyl, ethyl, n-propyl, isopropyl, n-butyl, isobutyl, sec-butyl and tert-butyl; or (iv) $R^8$ and $R^9$ together with the nitrogen atom linking them form a heterocycle corresponding to formula (II)

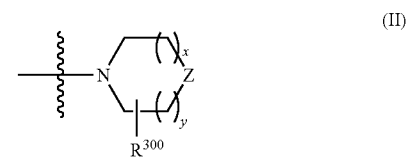

(II)

wherein

Z denotes O, S, $NR^{15a}$, $CH_2$ or $CF_2$, wherein $R^{15a}$ denotes H; methyl, ethyl, n-propyl, isopropyl, n-butyl, isobutyl, sec-butyl, tert-butyl, phenyl, naphthyl or pyridinyl or $R^{15a}$ represents a phenyl, naphthyl or pyridinyl group bonded via a $C_{1-3}$ alkylene group;

x and y each independently represent 0, 1 or 2, with the proviso that x+y=0, 1, 2 or 3, and $R^{300}$ denotes 0 to 4 substituents each independently selected from the group consisting of $C_{1-6}$ alkyl, —O—$C_{1-6}$ alkyl, OH, $CF_3$, F, aryl, heteroaryl, $C_{1-3}$ alkylene-aryl and $C_{1-3}$ alkylene-heteroaryl.

18. A compound as claimed in claim 1, selected from the group consisting of:

| | | |
|---|---|---|
| 1 | 2-((1-(4-Methoxy-2,6-dimethylphenylsulfonyl)piperidin-2-yl)methoxy)-1-(9-phenyl-9-(pyrrolidin-1-yl)-3-azaspiro[5.5]undecan-3-yl)ethanone | 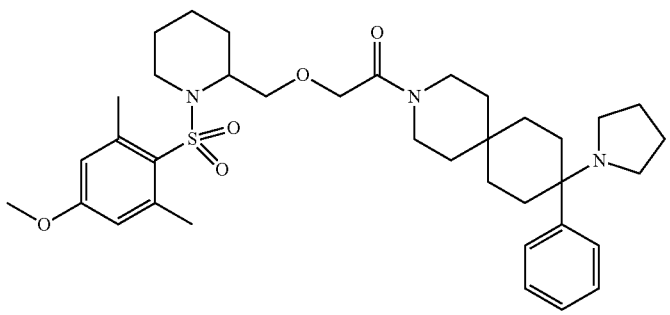 |
| 2 | 1-(9-(Dimethylamino)-9-phenyl-3-azaspiro[5.5]undecan-3-yl)-2-(((S)-1-(4-methoxy-2,6-dimethylphenylsulfonyl)piperidin-2-yl)methoxy)ethanone | 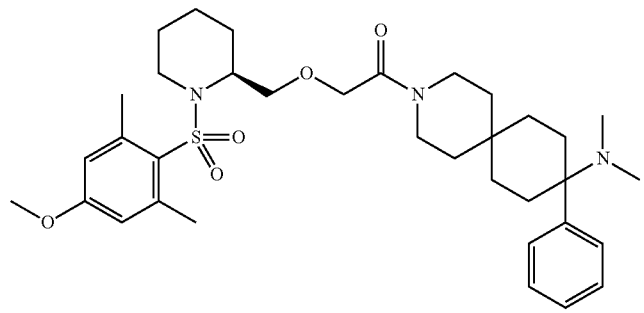 |

| | | |
|---|---|---|
| 3 | N-Cyclopropyl-N-(2-(2-(9-(dimethylamino)-9-phenyl-3-azaspiro[5.5]undecan-3-yl)-2-oxoethoxy)ethyl)-4-methoxy-2,6-dimethylbenzolsulfonamide | 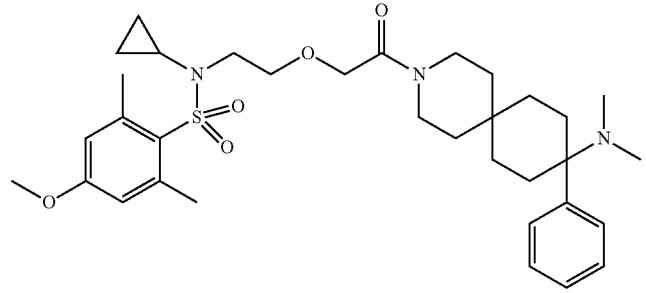 |
| 4 | 1-(9-(Dimethylamino)-9-phenyl-3-azaspiro[5.5]undecan-3-yl)-2-(((S)-1-(4-methoxy-2,6-dimethylphenylsulfonyl)-indolin-2-yl)methoxy)ethanone | 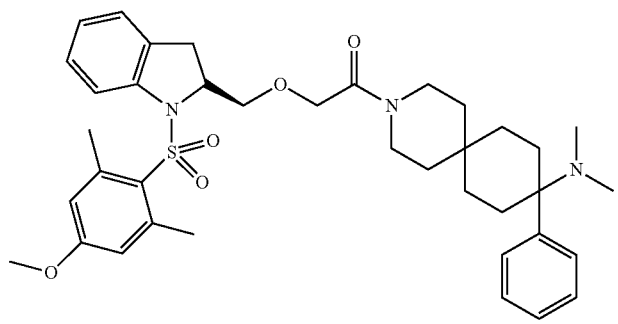 |
| 5 | N-((1R)-3-(9-(Dimethylamino)-9-phenyl-3-azaspiro[5.5]undecan-3-yl)-3-oxo-1-phenylpropyl)naphthalene-2-sulfonamide | 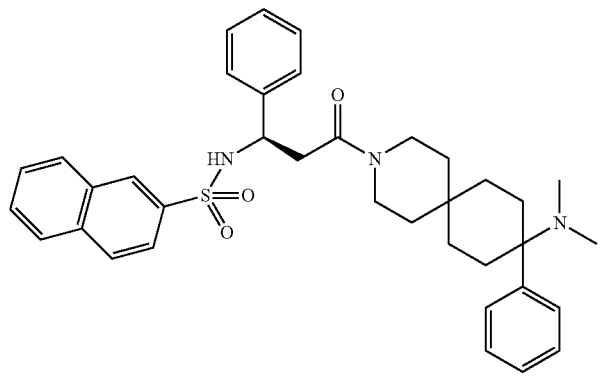 |
| 6 | 2-(((S)-1-(2-Chloro-6-methylphenylsulfonyl)piperidin-2-yl)methoxy)-1-(9-(dimethylamino)-9-phenyl-3-azaspiro[5.5]undecan-3-yl)ethanone | 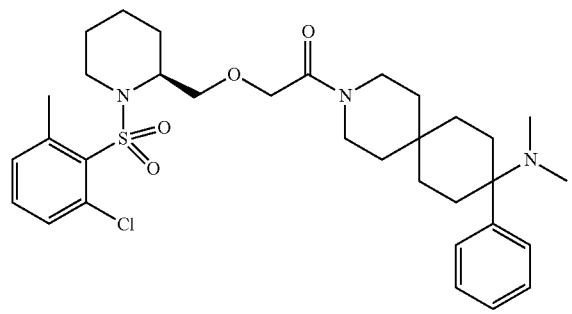 |

-continued

| 7 | 3-(1-(4-Chloro-2,5-dimethylphenylsulfonyl)piperidin-2-yl)-1-(9-(dimethylamino)-9-phenyl-3-azaspiro[5.5]undecan-3-yl)propan-1-one | 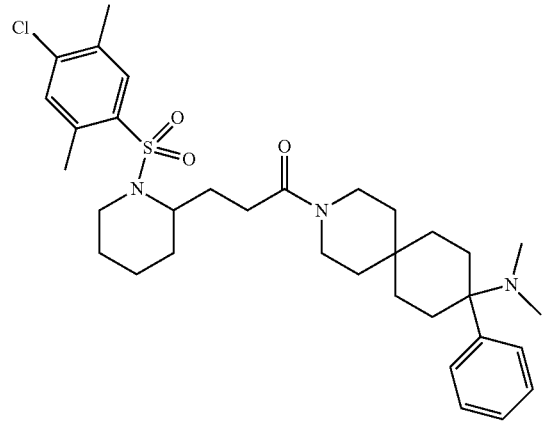 |
| 8 | 1-(9-(Dimethylamino)-9-phenyl-3-azaspiro[5.5]undecan-3-yl)-4-(1-(4-methoxy-2,6-dimethylphenylsulfonyl)piperidin-2-yl)butan-1-one | 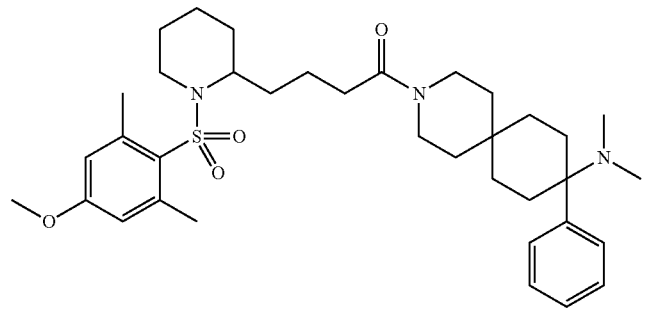 |
| 9 | 1-(9-(Dimethylamino)-9-phenyl-3-azaspiro[5.5]undecan-3-yl)-2-(1-(3-(trifluoromethyl)phenylsulfonyl)piperidin-2-yl)ethan-1-one | 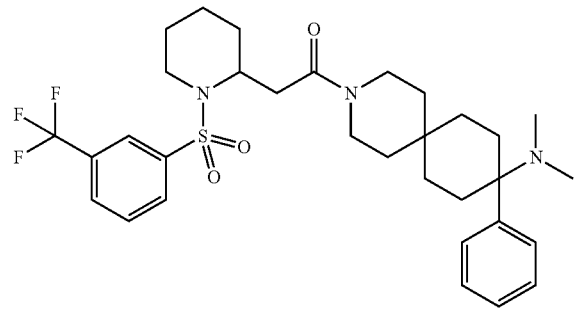 |
| 10 | (3R)-3-(2-(9-(Dimethylamino)-9-phenyl-3-azaspiro[5.5]undecan-3-yl)-2-oxoethyl)-4-(4-methoxy-2,6-dimethylphenylsulfonyl)-3,4-dihydropyrazin-2(1H)-one | 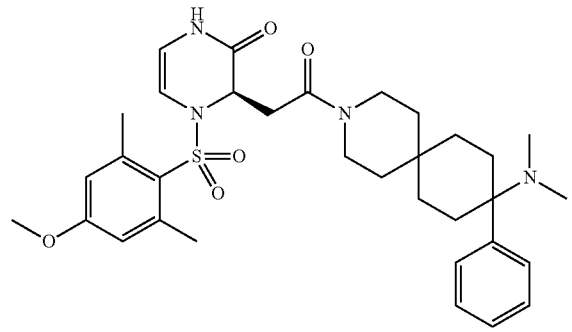 |

| | | |
|---|---|---|
| 11 | 1-(9-(Dimethylamino)-9-(3-fluorophenyl)-3-azaspiro[5.5]undecan-3-yl)-2-(((S)-1-(4-methoxy-2,6-dimethylphenylsulfonyl)piperidin-2-yl)methoxy)ethanone | 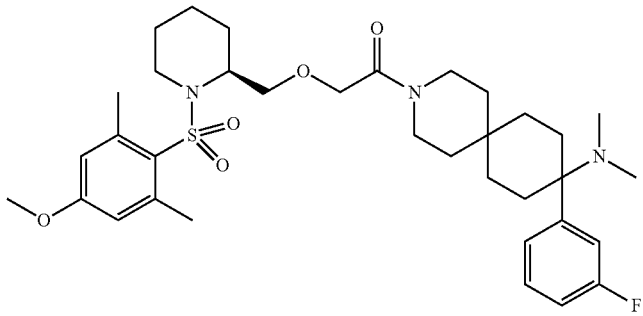 |
| 12 | 1-(9-(Azetidin-1-yl)-9-phenyl-3-azaspiro[5.5]undecan-3-yl)-2-(((S)-1-(4-methoxy-2,6-dimethylphenylsulfonyl)piperidin-2-yl)methoxy)ethanone | 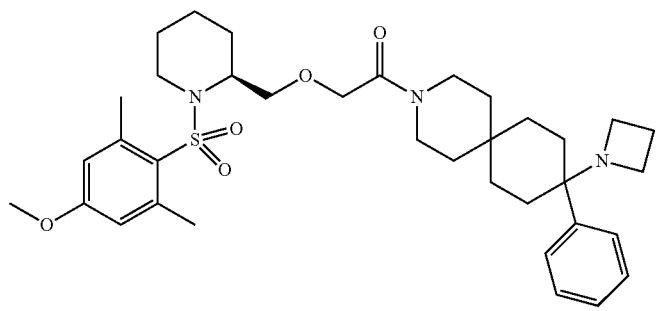 |
| 13 | 1-(9-(3,3-Difluoroazetidin-1-yl)-9-phenyl-3-azaspiro[5.5]undecan-3-yl)-2-(((S)-1-(4-methoxy-2,6-dimethylphenylsulfonyl)piperidin-2-yl)methoxy)ethanone | 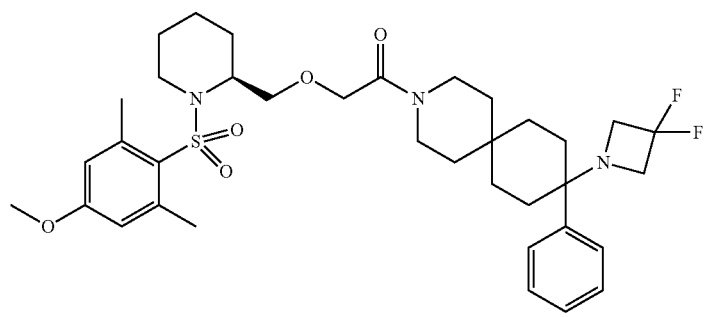 |
| CC-01 | 1-[3-(3-Fluorophenyl)-3-pyrrolidin-1-yl-9-azaspiro[5.5]undecan-9-yl]-2-[1-[[3-(trifluoromethyl)phenyl]sulfonyl]-piperidin-2-yl]-ethanone | 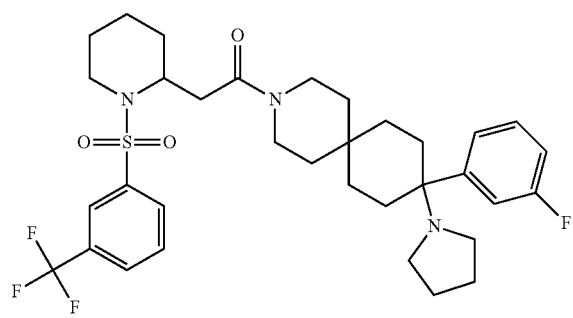 |
| CC-02 | 1-[3-(3-Fluorophenyl)-3-pyrrolidin-1-yl-9-azaspiro[5.5]undecan-9-yl]-4-[1-[(4-methoxy-2,6-dimethyl-phenyl)sulfonyl]-piperidin-2-yl]-butan-1-one | 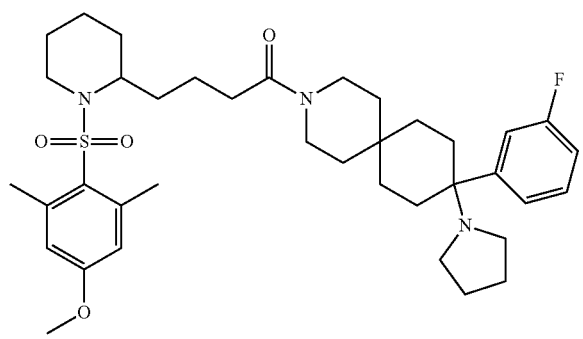 |

| | | |
|---|---|---|
| CC-03 | 1-[3-(3-Fluorophenyl)-3-pyrrolidin-1-yl-9-azaspiro[5.5]undecan-9-yl]-2-[[1-[(4-methoxy-2,6-dimethyl-phenyl)sulfonyl]-piperidin-2-yl]-methoxy]-ethanone | 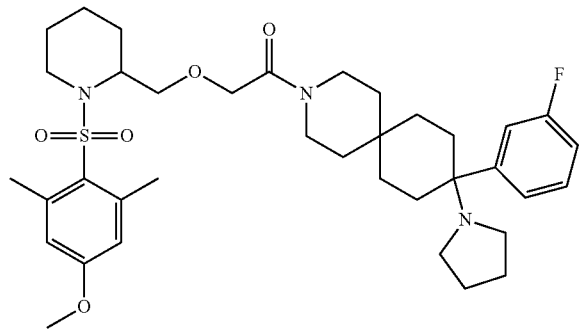 |
| CC-04 | N-Cyclopropyl-N-[2-[2-[3-(3-fluorophenyl)-3-pyrrolidin-1-yl-9-azaspiro[5.5]undecan-9-yl]-2-oxo-ethoxy]-ethyl]-4-methoxy-2,6-dimethyl-benzenesulfonic acid amide | 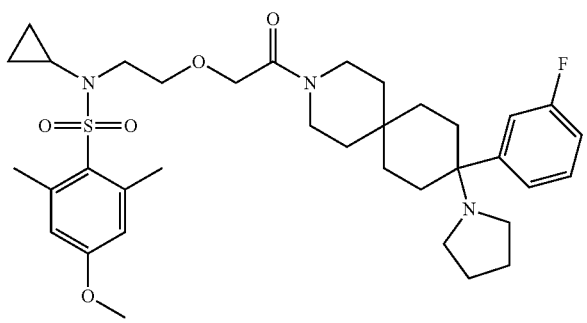 |
| CC-05 | 2-[[1-[(2-Chloro-6-methyl-phenyl)sulfonyl]-piperidin-2-yl]-methoxy]-1-[3-(3-fluorophenyl)-3-pyrrolidin-1-yl-9-azaspiro[5.5]undecan-9-yl]ethanone | 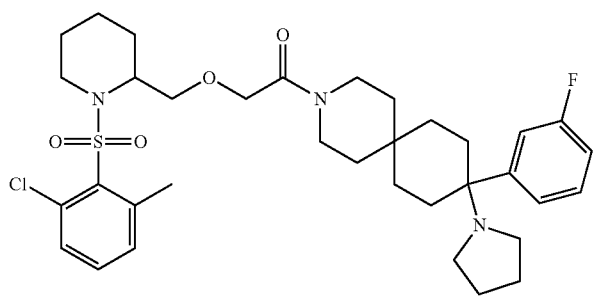 |
| CC-06 | 2-Chloro-N-cyclopropyl-N-[2-[2-[3-(3-fluorophenyl)-3-pyrrolidin-1-yl-9-azaspiro[5.5]undecan-9-yl]-2-oxo-ethoxy]-ethyl]-6-methyl-benzenesulfonic acid amide | 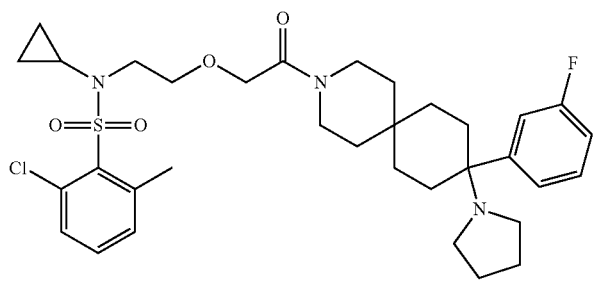 |

-continued

| | | |
|---|---|---|
| CC-07 | 3-[1-[(4-Chloro-2,5-dimethyl-phenyl)sulfonyl]-piperidin-2-yl]-1-[3-(3-fluorophenyl)-3-pyrrolidin-1-yl-9-azaspiro[5.5]undecan-9-yl]-propan-1-one | 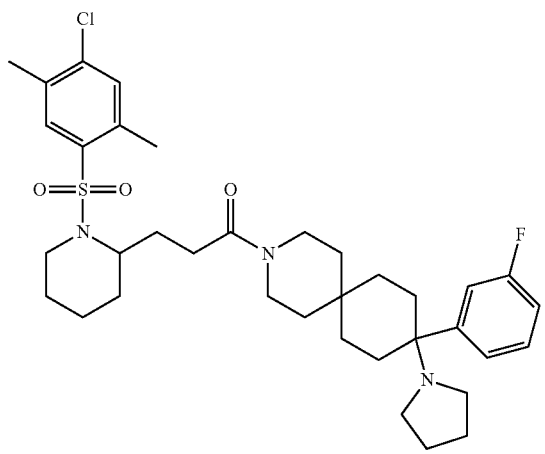 |
| CC-08 | N-[3-[3-(3-Fluorophenyl)-3-pyrrolidin-1-yl-9-azaspiro[5.5]undecan-9-yl]-3-oxo-1-phenyl-propyl]-naphthalene-2-sulfonic acid amide | 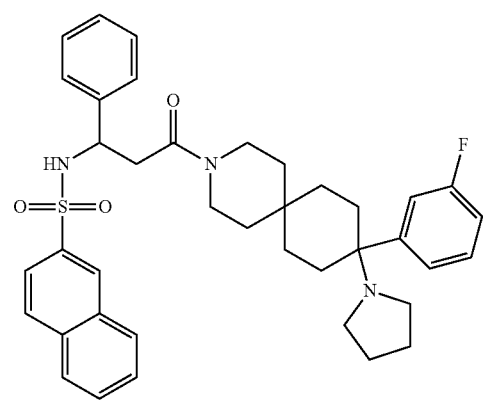 |
| CC-09 | 2-Chloro-N-cyclopropyl-N-[2-[2-(3-dimethylamino-3-thiophen-2-yl-9-azaspiro[5.5]undecan-9-yl)-2-oxo-ethoxy]-ethyl]-6-methyl-benzenesulfonic acid amide | 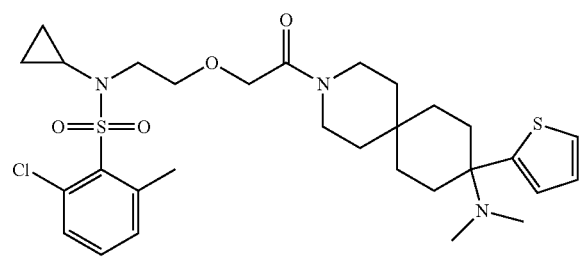 |
| CC-10 | 1-(3-Dimethylamino-3-thiophen-2-yl-9-azaspiro[5.5]undecan-9-yl)-2-[1-[[3-(trifluoromethyl)phenyl]sulfonyl]-piperidin-2-yl]-ethanone | 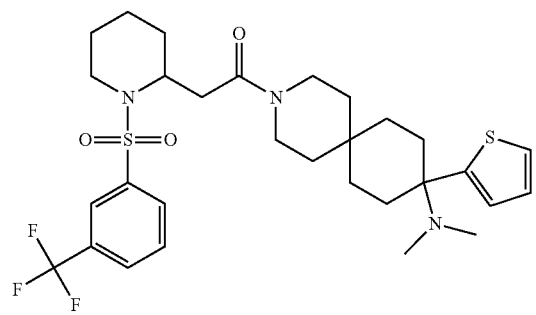 |

| | | |
|---|---|---|
| CC-11 | 1-(3-Dimethylamino-3-thiophen-2-yl-9-azaspiro[5.5]undecan-9-yl)-2-[[1-[(4-methoxy-2,6-dimethyl-phenyl)sulfonyl]-piperidin-2-yl]-methoxy]-ethanone | 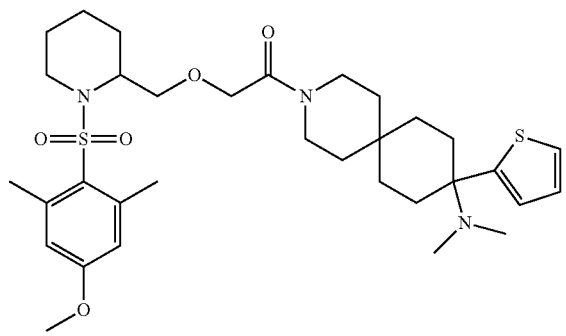 |
| CC-12 | N-Cyclopropyl-N-[2-[2-(3-dimethylamino-3-thiophen-2-yl-9-azaspiro[5.5]undecan-9-yl)-2-oxo-ethoxy]-ethyl]-4-methoxy-2,6-dimethyl-benzenesulfonic acid amide | 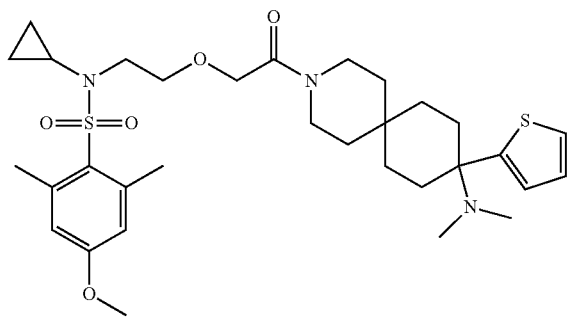 |
| CC-13 | 2-[[1-[(2-Chloro-6-methyl-phenyl)sulfonyl]-piperidin-2-yl]-methoxy]-1-(3-dimethylamino-3-thiophen-2-yl-9-azaspiro[5.5]undecan-9-yl)-ethanone | 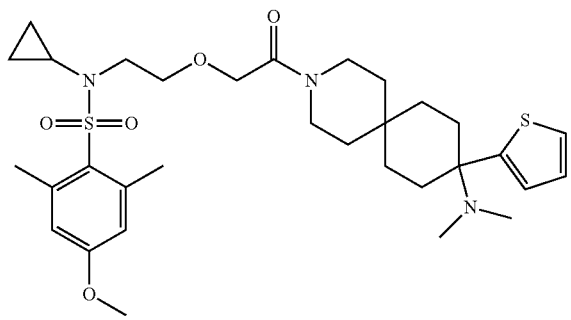 |
| CC-14 | 3-[1-[(4-Chloro-2,5-dimethyl-phenyl)sulfonyl]-piperidin-2-yl]-1-(3-dimethylamino-3-thiophen-2-yl-9-azaspiro[5.5]undecan-9-yl)-propan-1-one | 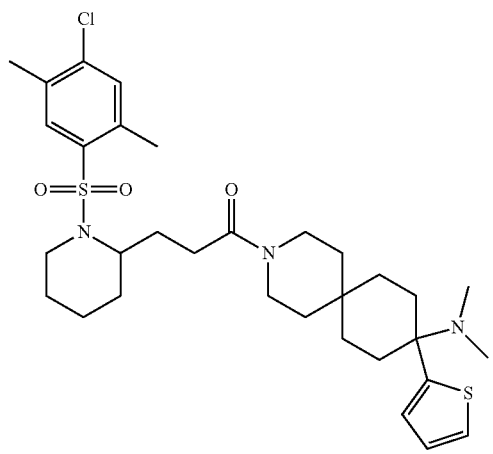 |

| | | |
|---|---|---|
| CC-15 | N-[3-(3-Dimethylamino-3-thiophen-2-yl-9-azaspiro[5.5]undecan-9-yl)-3-oxo-1-phenyl-propyl]-naphthalene-2-sulfonic acid amide | 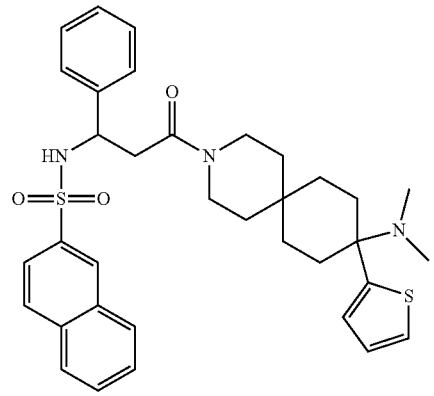 |
| CC-16 | 1-(3-Dimethylamino-3-thiophen-2-yl-9-azaspiro[5.5]undecan-9-yl)-4-[1-[(4-methoxy-2,6-dimethyl-phenyl)sulfonyl]-piperidin-2-yl]-butan-1-one | 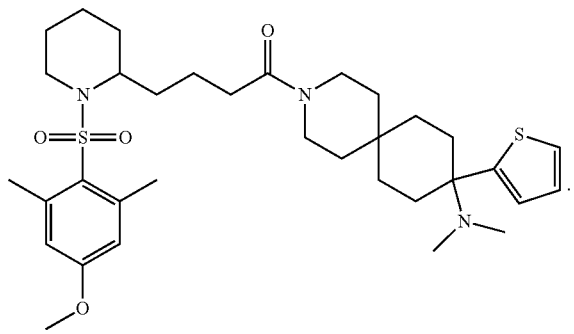 |

19. A pharmaceutical composition comprising a compound as claimed in claim 1 and at least one pharmaceutically acceptable carrier or auxiliary substance.

* * * * *